United States Patent
Torigoshi et al.

(10) Patent No.: US 7,329,245 B2
(45) Date of Patent: Feb. 12, 2008

(54) DISPOSABLE PAPER DIAPER AND METHOD OF ATTACHING EXPANSIBLE MEMBERS OF THE DISPOSABLE PAPER DIAPER

(75) Inventors: Keiji Torigoshi, Iyomishima (JP); Sadanao Manabe, Iyomishima (JP); Yosuke Mori, Iyomishima (JP)

(73) Assignees: Daio Paper Corporation (JP); Daio Paper Converting Co., Ltd. (JP)

( * ) Notice: Subject to any disclaimer, the term of this patent is extended or adjusted under 35 U.S.C. 154(b) by 489 days.

(21) Appl. No.: 10/333,530

(22) PCT Filed: Jul. 19, 2001

(86) PCT No.: PCT/JP01/06306

§ 371 (c)(1), (2), (4) Date: Jul. 14, 2003

(87) PCT Pub. No.: WO02/05738

PCT Pub. Date: Jan. 24, 2002

(65) Prior Publication Data

US 2004/0015146 A1    Jan. 22, 2004

(30) Foreign Application Priority Data

Jul. 19, 2000  (JP) .............................. 2000-218559
Dec. 8, 2000  (JP) .............................. 2000-374190

(51) Int. Cl.
A61F 13/20 (2006.01)

(52) U.S. Cl. ........................ 604/385.27; 604/385.24; 604/385.25; 604/385.26; 604/385.28

(58) Field of Classification Search ............ 604/385.27, 604/385.28, 385.24, 385.25, 385.26

See application file for complete search history.

(56) References Cited

U.S. PATENT DOCUMENTS

| 5,415,649 | A | * | 5/1995 | Watanabe et al. | 604/385.29 |
| 5,858,012 | A | * | 1/1999 | Yamaki et al. | 604/385.27 |
| 6,369,291 | B1 | * | 4/2002 | Uchimoto et al. | 604/367 |
| 6,554,815 | B1 | * | 4/2003 | Umebayashi | 604/385.27 |
| 6,620,146 | B2 | * | 9/2003 | Gibbs | 604/385.3 |

FOREIGN PATENT DOCUMENTS

| JP | 63-112714 | 5/1988 |
| JP | 4-161152 | 6/1992 |
| JP | 7-117125 | 5/1995 |
| JP | 8-215245 | 8/1996 |
| JP | 11-253489 | 9/1999 |
| JP | 2001-000478 | 1/2001 |
| JP | 2001-145666 | 5/2001 |

* cited by examiner

Primary Examiner—Tatyana Zalukaeva
Assistant Examiner—Ginger Chapman
(74) Attorney, Agent, or Firm—Andrus, Sceales, Starke & Sawall, LLP

(57) ABSTRACT

A disposable diaper having an absorbent, a waist opening and right and left leg openings which are formed when the diaper is in use, and many stretchable members which are provided along the peripheral direction of the diaper at least in a girth area having a lengthwise range extending from said waist opening's edge to said leg openings' start ends and which are spaced at intervals in the lengthwise direction of the diaper. In at least a front body, said stretchable members are provided discontinuously in part of or in the whole of a lengthwise range where said absorbent is located, in an area extending from a joint on one side to a joint on the other side of the diaper.

6 Claims, 51 Drawing Sheets

DISPOSABLE PAPER DIAPER AND METHOD OF ATTACHING EXPANSIBLE MEMBERS OF THE DISPOSABLE PAPER DIAPER

CROSS REFERENCE TO RELATED APPLICATION

The present application is the U.S. national stage application of International Application PCT/JP01/06306, filed Jul. 19, 2001, which international application was published on Jan. 24, 2002 as International Publication WO 02/05738. The International Application claims priority of Japanese Patent Application 1000-218559, filed Jul. 19, 2000 and Japanese Patent Application 2000-374190, filed Dec. 8, 2000.

FIELD OF THE INVENTION

The present invention relates to disposable diapers such as those of pants-type, of tape-type, and the like, as well as a method for attaching stretchable members in producing such disposable diaper.

BACKGROUND OF THE INVENTION

In a disposable diaper of pants-type, the right and left side edges of front body and the right and left side edges of back body are jointed, a pair of right and left side leg openings and a waist opening are formed on an overall sheet, and an absorbent element, which includes a flexible absorbent disposed between a liquid-pervious top sheet and a liquid-impervious back sheet, is attached to the inner surface of overall sheet, and the absorbent element is placed longitudinally from the front body to the back body within the central portion of overall sheet in the crosswise direction of diaper. Such disposable diapers are used universally.

In general, a disposable diaper of this kind is provided with waist stretchable members comprising rubber threads within a waist area in the front and back bodies along the waist opening's edge. An absorbent core is not located in the waist area. The waist stretchable members are spaced each other in the lengthwise direction so as to be parallel to the waist opening's edges. Another disposable diaper is available in the market, which is provided with girth stretchable members comprising rubber threads and fixed to the girth area which covers from the pair of leg openings to the crotch. An absorbent core is located in the girth area. The girth stretchable members are spaced each other in the lengthwise direction so as to be parallel to the waist opening's edges and placed so as to extend across the absorbent core. The girth stretchable member serves, together with the waist stretchable member, to prevent the diaper from slipping down. In addition, the girth stretchable member serves per se to improve tight contact between the diaper and the wearer's skin.

Particularly, in the disposable diaper of pants-type, the girth stretchable member is constituted of one or more under-waist stretchable members fixed to an underbelly corresponding area in the front body and one or more buttock stretchable members fixed to a buttock area in the back body. This buttock area is correlating to that under-waist area in configuration under-waist area. The under-waist stretchable members and buttock stretchable members are extended continuously from one side edge to the other side edge along the waist circumference fastening direction.

On the other hand, in a disposable diaper with tape-tab fastening means, so-called a disposable diaper of tape-type, the right and left side edges of front body and the right and left side edges of back body are not jointed until the diaper is used (worn) and in general, the above girth stretchable member is not provided.

It has been considered that by fixing the girth stretchable member to the diaper in the conventional way, since the gap formed between an absorbent main body and the wearer's body can be small, the garment fit of diaper to the wearer's skin should be improved so that efficient protection against the leakage can be obtained. However, it is found that since this girth stretchable member is placed so as to extend across the absorbent, the absorbent main body is shirred so as to form longitudinal creases along the direction of the front-back of the product. Then, liquid body exudates like urine is introduced through these creases toward the waist area before being absorbed, resulting in the fear of increased leakage from the front and back areas. Particularly, an infant often takes a pose of getting on all fours and the urine is discharged towards the front side of diaper. Accordingly, a far larger amount of body exudates is introduced to the waist area and leaked in the front body than in the back body.

The conventional girth stretchable member is placed so as to extend continuously along the girth in the front body and along the girth in the back body, respectively. Accordingly, the diaper is shirred so as to form a large number of creases on the whole of girth area, which results in a bad appearance of diaper. Particularly, it is found that since the conventional stretchable member is fixed to the whole of girth area including the area where the absorbent is located, the diaper may have an extremely bad appearance.

Additionally, if visible design such as pattern of animation character is provided on the front and back bodies of diaper, it may not show clearly due to the creases.

In order to solve these problems, it is easiest and effective not to provide girth stretchable members. However, by doing so, the diaper may not exhibit the above effects attained by the girth stretchable member. That is to say, the diaper may slip down and the tight contact between the diaper and the wearer's skin may not be kept sufficiently.

SUMMARY OF THE INVENTION

Therefore it is the first object of the present invention is to provide a disposable diaper, which is not shirred at its absorbent so as not to obstruct its absorbency, which has a neat appearance, and which has sufficient effect for preventing it from slipping down and for keeping the tight contact between itself and the wearer's skin.

It is the second object to provide a disposable diaper, which can prevent visible design such as pattern of animation character provided on its front and back bodies from being unclear due to creases formed thereon.

It is the third object to provide a disposable diaper with a neat appearance, which has a smooth outer surface due to few creases thereon. Even if they could be seen, they are fine creases and as a whole the diaper has a flat outer surface.

Another subject of the present disposable diaper is that, when the diaper is worn, a pressure is applied by the diaper to the wearer's skin not in spots but in planes so that there is no trace of diaper's rubber threads on the wearer's skin and so that friction formed between the inner surface of diaper and the wearer's skin is applied totally, whereby the tight contact between them can be kept and good garment fit can be obtained, thus the diaper can be prevented from slipping down.

It is the fourth object to provide the method by which this disposable diaper can be produced.

Now, the present invention, by which the above problems can be solved and by which the above objects can be attained, will be stated.

<The Invention of Disposable Diaper>

A disposable diaper in accordance with the present invention has an absorbent, a waist opening, right and left leg openings which are formed when the diaper is in use, and many stretchable members which are provided along the peripheral direction of the diaper at least in a girth area having the lengthwise range extending from the above waist opening's edge to the above leg openings' start ends and which are spaced at intervals in the lengthwise direction of diaper.

According to an embodiment of the present invention, at least in a front body, the stretchable members are provided at least in side portions, and the stretchable members in the girth area, particularly under-waist stretchable members, are not provided in part of or in the whole of the area where the above absorbent is located.

This form can be incorporated in a disposable diaper of tape-type as well as a disposable diaper of pants-type where the right and left side edges of the front body and those of the back body are jointed.

The above stretchable members may be provided also in the back body continuously all over the body.

The above stretchable members may be provided also again in the back body discontinuously in part of or in the whole of the area where the above absorbent is located.

The above stretchable members are provided between any two of plural overall sheets, preferably between two overall sheets, and an absorbent element having the above absorbent may be arranged on the side to be used of the overall sheet.

According to an embodiment of the present invention, visible design is provided on the outer surface of the diaper where the absorbent is located on the reverse. Since there are substantially no stretchable members in such area, the design shows clearly.

In the front body, under-waist stretchable members are discontinuous over the absorbent, which decreases a constriction force caused by the stretchable members along the waist circumference fastening direction against the absorbent. On the contrary, in a conventional diaper, since under-waist stretchable members are extended so as to be continuous over an absorbent, the constriction force caused by the stretchable members is applied there, and the diaper is shirred there so as to form longitudinal creases along the waist circumference fastening direction. These creases lift up the absorbent above the wearer's skin, which causes leak from the girth area. In this respect, according to the present invention, such problem can be prevented.

In the back body, the buttock stretchable members are extended without any discontinuous part from the joint on one side to the joint on the other side. Accordingly, the present diaper has sufficient effect for preventing it from slipping down and for keeping the tight contact between itself and the wearer's skin. Further, since there are very few creases at the part where the under-waist stretchable members are discontinuous, when clothes such as pants are put on over the diaper, good garment fit between the clothes and the diaper and a neat appearance can be obtained.

On the other hand, it is preferable that in at least the front body, the stretchable members of 620 dtex or less are fixed to a sheet defining an outer surface of the diaper, the members being disposed at the intervals of 7.0 mm or less in at least 60% lengthwise range of the girth area.

In this embodiment of the present invention, as shown schematically in FIG. 39, creases are formed narrowly in the peripheral direction and short in the lengthwise direction (this direction is perpendicular to the peripheral direction), and they continue in the substantially lengthwise direction. Each of the creases is almost even, and its constriction by rubber threads g is so small that it is difficult to distinguish the existence of the rubber threads on the diaper if the rubber threads have the same color as that of sheet defining the outer surface of diaper.

Consequently, the creases are inconspicuous, and very thin though visible, so that the disposable diaper has a totally flat outer surface and a neat and good appearance. Additionally, when the diaper is worn, the pressure is applied by the diaper to the wearer's skin not in spots but in planes so that there is no trace of rubber threads on the wearer's skin and so that friction formed between the inner surface of the diaper and the wearer's skin is applied totally, whereby the tight contact between them can be kept and good garment fit can be obtained, thus the diaper can be prevented from slipping down.

In at least the front body, the stretchable members of 620 dtex or less are fixed to a sheet defining an outer surface of the diaper, the members being disposed at the intervals of 7.0 mm or less in at least 60% lengthwise range of the girth area, and existing only at the right and left side portions except central portion of the girth area. When you see a diaper it is the central portion (circumferentially central portion) thereof that tends to be conspicuous. So the diaper of this configuration has a good appearance since the stretchable members are provided only at the right and left side portions and not at the central portion.

A semi-stiff absorbent core is arranged on the lengthwise direction of the diaper and the stretchable members are provided at not the central portion but the right and left side portions of the girth area. Since the sheet defining the outer surface of the diaper is flexible and the absorbent core is semi-stiff compared to the flexible sheet, deformation and crease due to the constriction force by the stretchable members are seldom caused in the absorbent core. This means that deformation and crease are seldom caused in the conspicuous central portion, resulting in the diaper having a good appearance. Additionally, when the central portion of the diaper is provided with visible design such as pattern of animation character, since the deformation and crease are seldom caused in the central portion, visible design shows clearly. The constriction force along the peripheral direction applies mainly to the side portions of the girth area. Then, due to the friction force between the diaper and the wearer's skin, the constriction force is decreased toward the center of the absorbent core. Accordingly, in the substantial whole area of the absorbent core, the constriction force along the peripheral direction is small, resulting in low pressure applied to the wearer's belly.

To provide stretchable members not in the central portion but in the right and left side portions of the crotch area prevents the flapping of both side portions of the sheet defining the outer surface of the diaper, which results in good garment fit and neat appearance of the diaper.

In every embodiment of the present invention, it is preferable that the stretchable member has an extensibility of 150 to 350% and a stretching stress of 4 to 17 g under the extensibility of 150%. By limiting to this, the effect of the present invention is further ensured.

The above stretchable members are arranged on the inner surface of a nonwoven fabric inside sheet. This nonwoven fabric inside sheet has preferably the opacity of 50% or more defined by JIS P 8138.

When the opacity of the nonwoven fabric inside sheet is 50% or more defined by JIS P 8138, it is impossible or difficult to distinguish the existence of stretchable members. Accordingly, the user does not need to worry about too strong fastening and trace of diaper's rubber threads on his skin. Further, since the stretchable members are not seen through the nonwoven fabric sheet, the diaper gives an impression of high quality and good finish.

According to an embodiment of the present invention, the nonwoven fabric inside sheet has the opacity of 40% or more defined by JIS P 8138 and the stretchable members of 925 dtex or less. In spite of low level of opacity, it is difficult to see the stretchable members from a distance, since they are of 925 dtex or less. And the user does not need to worry about too strong fastening and trace of diaper's rubber threads on his skin.

It is particularly preferable that the stretchable members are spaced each other at the intervals of 7.0 mm or less. Due to such intervals, the diaper exhibits the effect of present invention more clearly, namely, the diaper has a smooth outer surface due to few creases thereon. Even if they could be seen, they are fine creases and as a whole the diaper has a flat outer surface, resulting in a neat appearance.

It is more preferable that the nonwoven inside fabric sheet has the weight of 40 g/m$^2$ or less, the thickness of 0.1 mm or more and the stiffness of 10 mm or more defined by JIS 8143. Due to the thickness of 0.1 mm or more, the stretchable member can easily be concealed. Further, due to the weight of 40 g/m$^2$ or less and the stiffness of 10 mm or more, its stretchability is increased and feeling is improved.

<Method for Attaching Stretchable Members to Disposable Diaper>

As stated in Background of the Invention, there is known the following method for continuously attaching under-waist stretchable members and buttock stretchable members. In this conventional method, stretchable members made of rubber threads are supplied continuously to a base member to which the stretchable members are attached, e.g. an overall sheet, while the stretchable members are arranged and fixed in their elastically stretched state.

On the other hand, in a case of the disposable diaper stated above, a plurality of stretchable members are attached discontinuously at the predetermined intervals along the crosswise direction of the diaper. So, it is impossible to attach the stretchable members to the base member by means of the conventional attaching method. That is to say, it is required that the stretchable members are attached intermittently to the base member. In this situation, the stretchable members must be cut into pieces of predetermined length, before being attached to the base member (particularly when the base member is such as an overall sheet, to which the stretchable members are already attached and could not be cut afterward).

But there is a problem with this case. Different from the case of the continuous attachment, even if the cut stretchable members are attached as they are, with an adhesive in their stretched state, they immediately constrict and return to their original state. It is because there exists only an adhesive force to keep their stretching and the adhesive force is not sufficient due to a small contact area formed between the two members to be adhered of different kinds of materials.

In order to solve this problem, is provided a method for attaching stretchable members in producing such disposable diaper. First, on a belt-shaped support sheet, stretchable members are arranged and fixed along its lengthwise direction. Next, the support sheet is cut at the predetermined interval along its lengthwise direction into a plurality of stretchable sheet members. Then, these stretchable sheet members are attached discontinuously to the base member at the predetermined interval on the crosswise direction of diaper.

Alternatively, another method is provided. First, on a belt-shaped support sheet, stretchable members are arranged and fixed along its lengthwise direction. Next, the support sheet is cut at the predetermined interval along its lengthwise direction into a plurality of stretchable sheet members. Then these stretchable sheet members are adhesive-bonded to the base member in a stretched state of the stretchable members excluding the adjacent side portions of each stretchable sheet member. After that, the non-bonded adjacent side portions are constricted so that the stretchable sheet members are apart from each other to be discontinuous.

In further another method, an adhesive is applied on a belt-shaped support sheet at the predetermined interval on its lengthwise direction, the support sheet is cut to make an opening at the central portion of each adhesive-applied area on the support sheet, and the above stretchable sheet members are arranged and fixed so as to surround the edge of opening of each adhesive-applied area on the support sheet, whereby the stretchable sheet members can be attached to the belt-shaped support sheet discontinuously at the predetermined interval on its lengthwise direction.

Additionally, in another available method, stretchable members are arranged and fixed on a belt-shaped support sheet along its lengthwise direction, then, the support sheet is cut into two members with wavelike cutting line across the stretchable members, one of the cut members is attached to a base member in the under-waist area and the other is attached to a base member at the buttock area while the lengthwise direction of cut members goes along the crosswise direction of diaper.

Further, in another possible method, stretchable members are arranged and fixed on a belt-shaped support sheet along its lengthwise direction, then, retaining members are fixed on the support sheet at the predetermined interval, through the fixed retaining members the resultant support sheet can be cut.

As stated above, in the methods of the present invention, the stretchable sheet members, which are arranged and fixed on the support sheet, are attached to a base member discontinuously at the predetermined interval on the crosswise direction of diaper. Accordingly, an operation for attaching stretchable members to the support sheet can be carried out sequentially. Further, since each stretchable member to be attached to the base member is sheet-shaped, the contact area formed between the stretchable sheet member and the base member is increased remarkably, which leads to high adhesive force. As a result, a plurality of stretchable members can be more surely and more easily attached to the base member, discontinuously and in their stretched state along the stretching direction.

BEST MODE FOR CARRYING OUT THE INVENTION

Now, the disposable diaper of pants-type in accordance with the present invention is described closely, referring to several embodiments. However, the present invention can be applied to also a disposable diaper of tape-type, each of which is used (worn) by jointing the right and left side edges of its front body and the right and left side edges of its back body with fastening tapes each coated with an adhesive.

Now, the present invention is described more closely, referring to the embodiments of disposable diaper of pants-type.

<The Explanation of Terms of the Present Invention>

Referring to mainly FIG. 40, terms are explained below, which are related to the parts and directions of diaper in accordance with the present invention.

Figure 1:
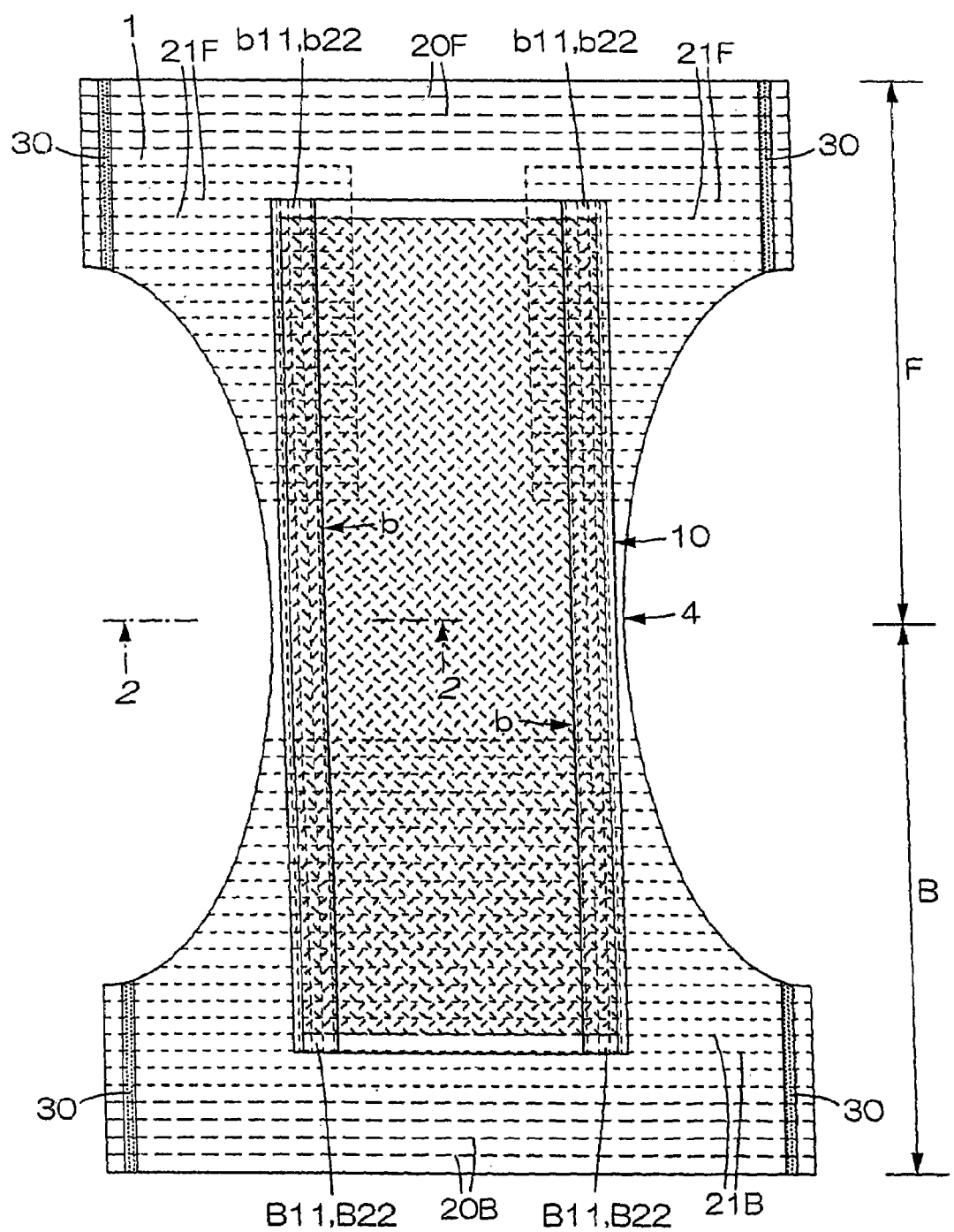
FIG. 1 is a plan view of the disposable diaper of pants-type in accordance with an embodiment of the present invention when the diaper is in its flat-out state.
Figure 2:
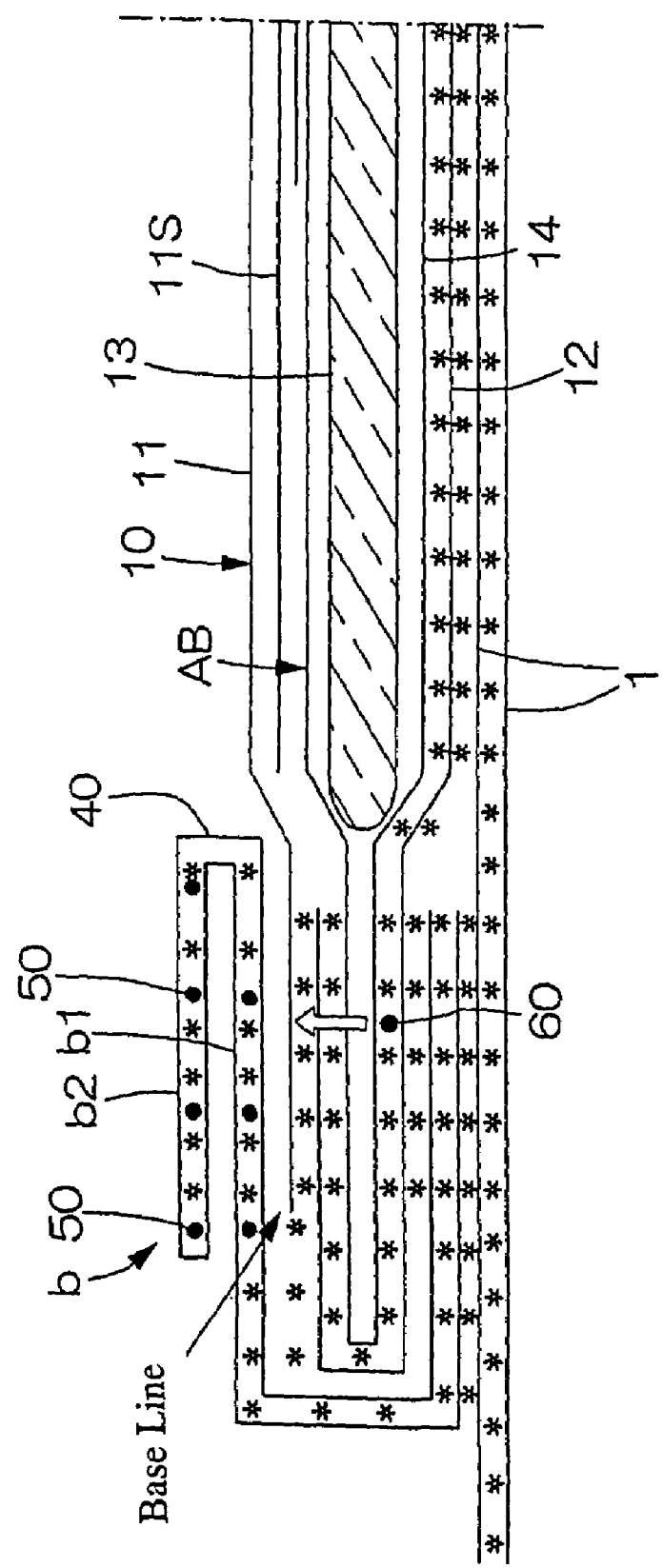
FIG. 2 is a sectional view taken in the direction of arrows along the line 2-2 of FIG. 1.

As shown in FIGS. 1 and 2, a disposable diaper of pants-type in accordance with the present invention comprises, as main parts thereof, a flexible overall sheet 1 and an absorbent main body 10. This absorbent main body 10 is provided on the inner surface (facing a wearer) of overall sheet 1 so as to extend toward the front side (upward in FIG. 1) and toward the back side (downward in FIG. 1) from a diaper bottom 4.

The overall sheet 1 is manufactured by laminating and fixing two or more than three breathable and water repellant nonwoven fabrics. Then, in the production process of this diaper, after superposing step of overall sheet 1 and the absorbent main body 10, the final step is carried out. In this final step, the longitudinal opposite side edges of front body F and the longitudinal opposite side edges of back body B are totally jointed with jointing means such as ultrasonic sealing or hot melt adhesive (the joint is designated by reference numeral 30) to thereby form a waist opening WO and a pair of right and left leg openings LO.

Figure 40:
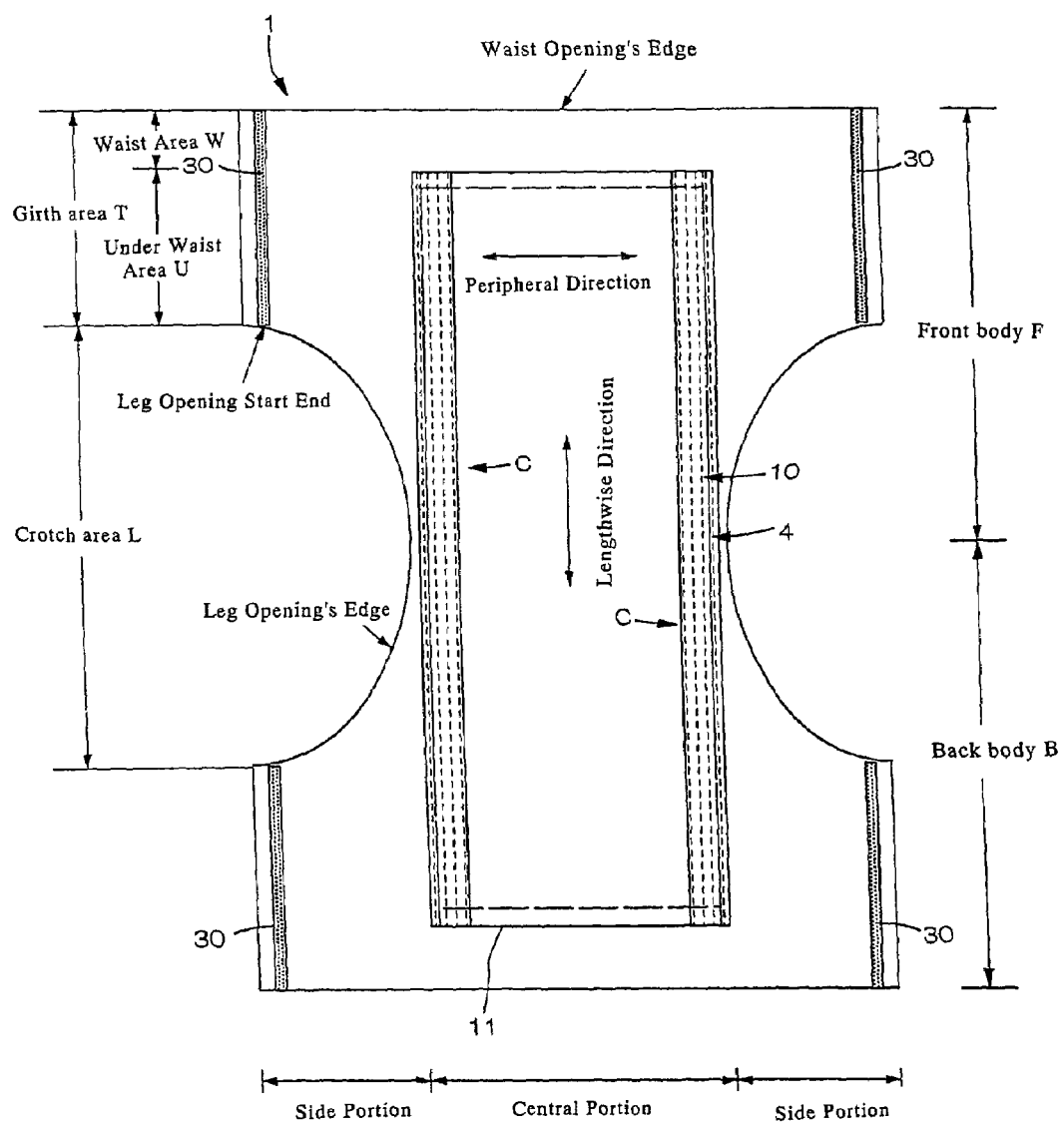
FIG. 40 is a plan view from the wearer's side showing the inner surface of the disposable diaper when the diaper is in its flat-out state, for explaining the terms of the present invention.
Figure 41:
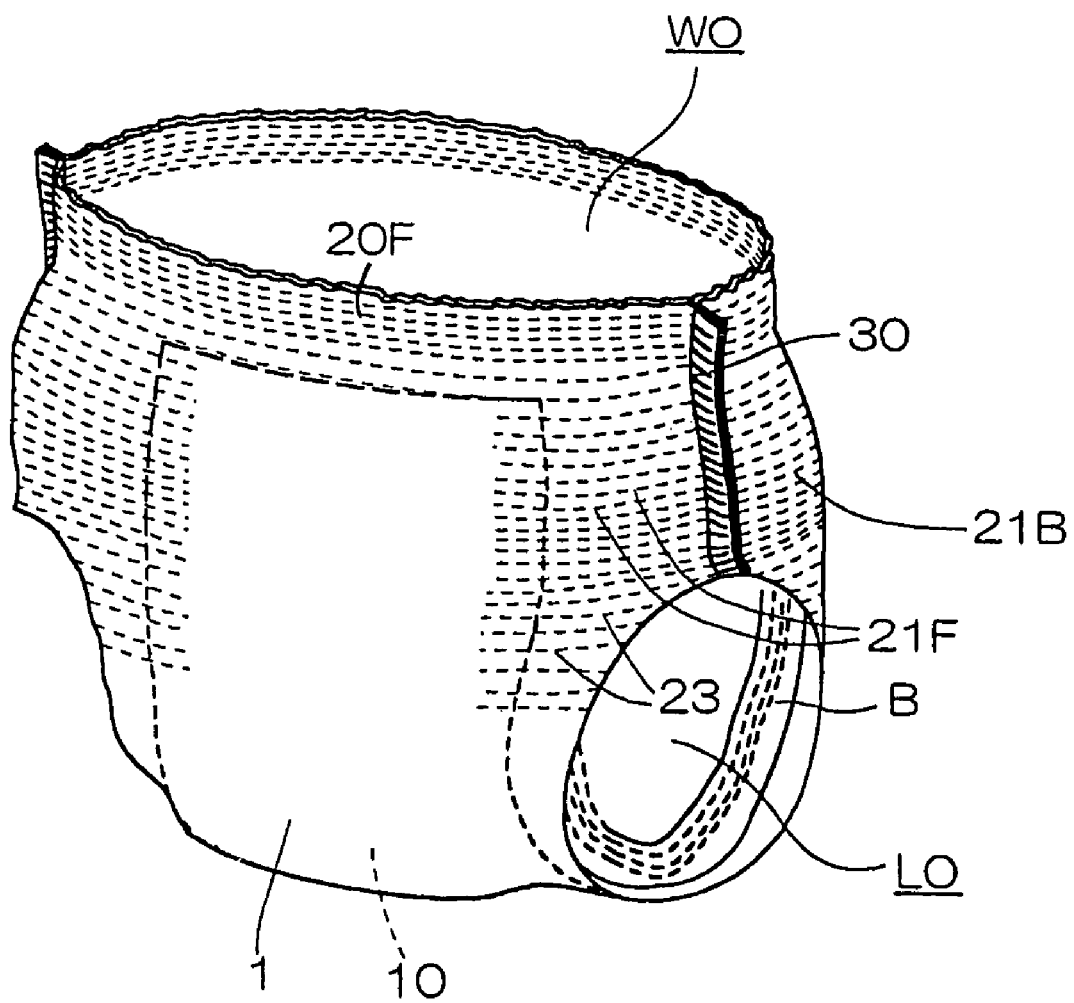
FIG. 41 is a perspective view showing one embodiment of the disposable diaper of pants-type.

Terms shown in FIG. 40 are explained below. First, the term "Lengthwise Direction" means the direction from the front side to the back side or from the back side to the front side in the diaper. On the other hand, the term "Peripheral Direction" means the direction being perpendicular to the above term "Lengthwise Direction". Next, the term "Leg Opening's Edge" means the edge of leg opening LO. The term "Leg Opening's Start End" means the position where the leg opening's edge and the joint 30 are crossed each other and also means the start of leg opening's edge. The term "Girth area" T means a whole area of the girth having the lengthwise range extending from the waist opening's edge to the leg openings' start ends. This girth area T can be divided conceptually into "Waist Area" W and "Under-Waist Area" U. Although the length of these areas differs depending on the size of diaper, the length of waist area W is 15 to 40 mm and the length of under-waist area U is 65 to 120 mm. Then, the term "Crotch area" L means a whole area having the lengthwise range forming the leg opening LO. On the other hand, the term "Central Portion" means a portion, which is central on the crosswise direction of diaper. Then, the longitudinal centerline of diaper is included in this central portion while opposite side portions are not. Finally, the term "Side Portion" means the right or left side portion of girth area T.

<Embodiments of Disposable Diaper>

As shown in FIG. 1, a disposable diaper of pants-type in accordance with the first embodiment of the present invention comprises, as main parts thereof, a flexible overall sheet 1 and an absorbent main body 10. This absorbent main body 10 is fixed on the inner surface of overall sheet 1 and placed so as to extend from a diaper bottom 4 toward the front end (upward in FIG. 1) and toward the back end (downward in FIG. 1).

The overall sheet 1 is manufactured by laminating and fixing two sheets of breathable and water repellant nonwoven fabrics. Then, in the production process of this diaper, after the superposing step of overall sheet 1 and absorbent main body 10, the last step is carried out. In this last step, the longitudinal opposite side edges of front body F and the longitudinal opposite side edges of back body B are totally jointed with jointing means such as ultrasonic sealing or hot melt adhesive (the joint is designated by reference numeral 30) to thereby form a waist opening and a pair of right and left leg openings.

The absorbent main body 10 comprises, as shown in FIG. 2, a liquid pervious top sheet 11, an absorbent AB, and a liquid impervious back sheet 12, which are adhesive-bonded integrally with hot melt adhesive (As shown in FIG. 2, fixed portions are represented by symbols *). The top sheet 11 is manufactured from e.g. nonwoven fabric and brought into contact with the wearer's skin directly, and has the shape of rectangle. The absorbent AB comprises a rectangle shaped absorbent core 13 and a rectangle shaped crepe paper 14. The absorbent core 13 is manufactured mainly from flocculent pulp and has stiffness to some degree. The crepe paper 14 wraps the whole of upper and under surfaces of absorbent core 13 and laterally extends beyond the side edge of absorbent core 13 to thereby form an extended side portion of absorbent AB. The back sheet 12 is manufactured from e.g. polyethylene plastic film and which has the shape of rectangle. The back sheet 12 wraps around the absorbent AB from its under surface to the opposite side portions of its upper surface If required, as shown in FIG. 2, a liquid pervious second sheet 11S may be disposed between the liquid pervious top sheet 11 and the crepe paper 14.

Almost all the back of the absorbent main body 10 is adhesive-bonded to the overall sheet 1 with hot melt adhesive so as to be integrated each other, leaving small opposite side portions of the liquid impervious back sheet 12 unfixed to the overall sheet 1.

Standing cuffs b, b are formed at the opposite side portions of absorbent main body 10 so as to stand around the wearer's legs by standing out toward the wearer. Each standing cuff b comprises a standing sheet 40, which is continuous in the substantially crosswise direction, and one stretchable member or, as shown in FIG. 2, a plurality of stretchable members 50, 50 . . . . The stretchable member comprises, for example, rubber thread.

Further, the standing cuff b comprises a double portion formed with the standing sheet 40. The stretchable members 50, 50 . . . are included and fixed in the double portion with e.g. hot melt adhesive. It is preferable that the standing sheets 40, which form the standing cuffs b, b, are not liquid pervious but liquid impervious or hydrophobic. Alternatively, it is also preferably that the standing sheet is treated with e.g. silicone so as to have water repellency.

The inner surface (absorbent-side surface) of the double portion of standing sheet 40 is fixed, with e.g. hot melt adhesive, to the outer surface (double portion-side surface) of liquid impervious back sheet 12 at its wraparound portion over the side portion of absorbent AB. The proximal edge where the inner surface of the double standing sheet 40 is fixed to the liquid pervious sheet 12, defines the base line from which the standing cuff b stands.

The laterally inboard portion with respect to this base line is not fixed to the diaper body but free therefrom. Further, this free inboard portion folds back halfway so as to be divided functionally and conceptually into two portions, a standing portion b1 which stands toward the longitudinal centerline of the diaper and a surface-contacting portion b2 which bends outwardly.

In the front and back ends of the standing cuff b in its longitudinal direction the portion corresponding to the above-said standing portion b11 (the extension of the standing portion b1) is fixed to the diaper, concretely to the outer surface of the liquid pervious top sheet 11, by laying the portion b11 toward the longitudinal centerline of the diaper, while the portion corresponding to the above-said surface-contacting portion b22 (the extension of the surface-contacting portion b2) being folded back and inverted is fixed to the portion corresponding to the standing portion b11.

In a basic aspect, at least one stretchable member 50 extends on the surface-contacting portion b2. Preferably, the stretchable member 50 extends along the side edge of the surface-contacting portion b2. Further, it is preferable that the stretchable member 50 extends also on the standing portion b1.

In the more preferable aspect, the stretchable members 50, 50 . . . extend in the vicinity of the base line for the standing portion b1, in the vicinity of the distal edge of the double standing sheet, and in the vicinity of the side edge of the surface-contacting portion b2. In addition, a plurality of stretchable members 50, 50 . . . preferably extend in the vicinity of the side edge of the surface-contacting portion b2 as shown. Additionally, in order to improve the standing ability of the standing portion b1, a plurality of stretchable members 50, 50 . . . may further extend on the standing portion b1. In this Figure, are shown seven stretchable members in total, three stretchable members in its standing portion b1 and four stretchable members in its surface-contacting portion b2.

Figure 3:
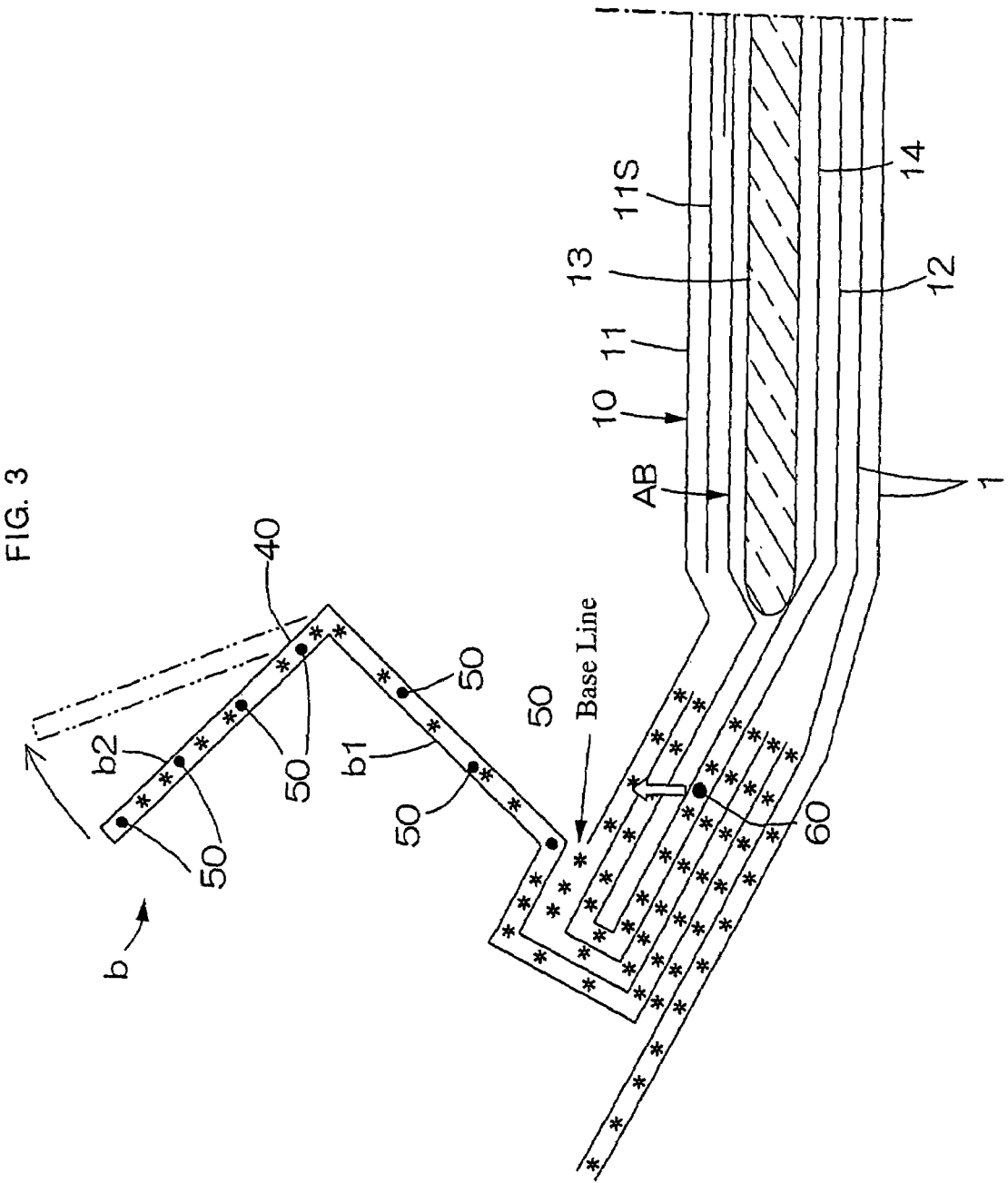
FIG. 3 is a sectional view taken on line 2-2 of FIG. 1 when the diaper is in its product state.
Figure 4:
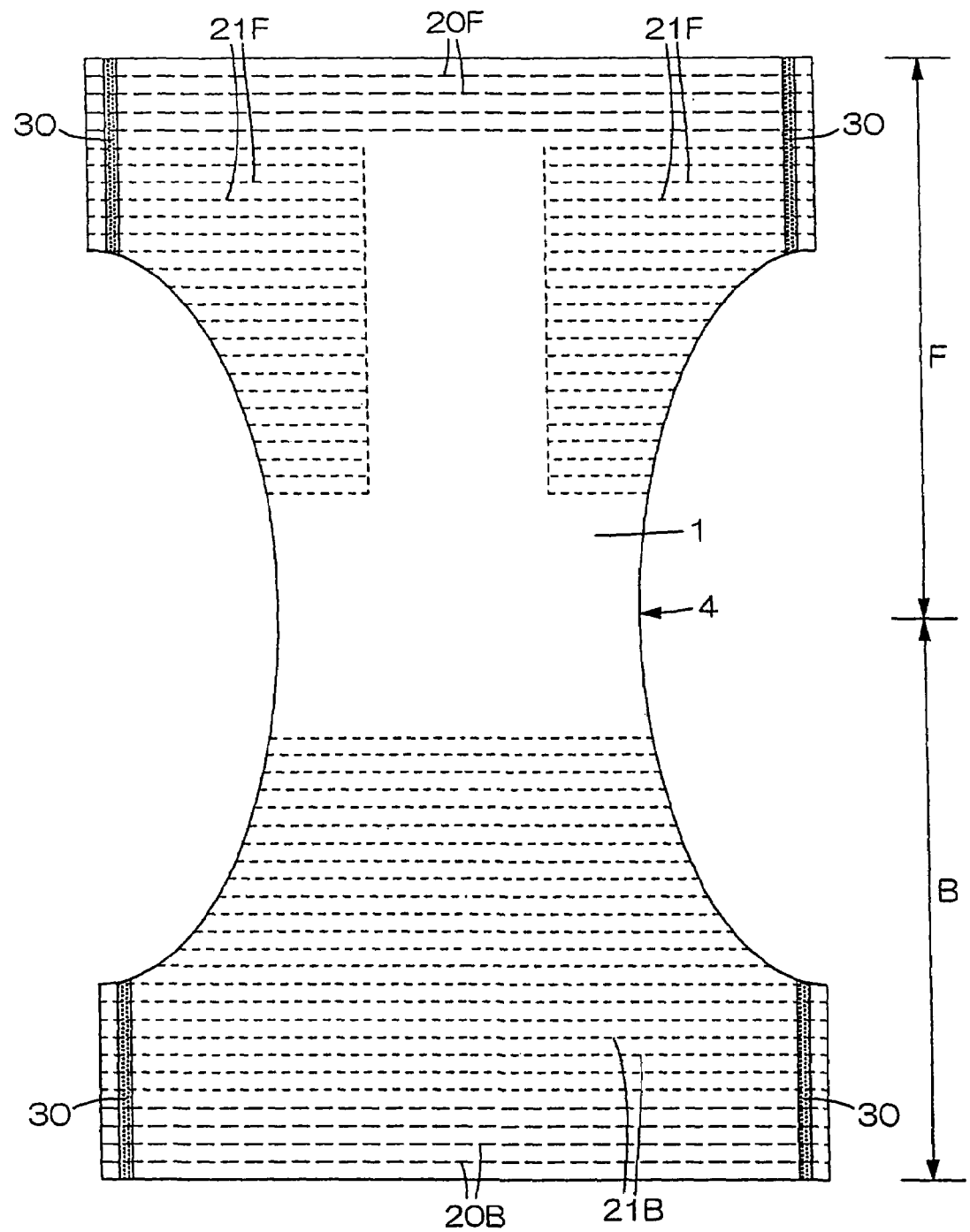
FIG. 4 is a plan view of the outer surface (facing outside) of the diaper in its flat-out state.

In FIG. 1, the diaper is in its longitudinally flat-out state. Actually, when the diaper is applied to the wearer, it defines a boat-form through the means of application of constriction force caused by the stretchable members 50, 50 . . . . Therefore, when the diaper is worn, in its leg portion, the standing cuff b stands due to the above constriction force as shown in FIG. 3, while in its front and back ends, it does not stand but keeps original position. In this case, the side portion of absorbent main body 10 is deformed and lifted. At the same time, the absorbent AB is slightly deformed and lifted. Thus, a deep pocket space is formed in the diaper.

In addition, in such lifted state, the contracting force by the stretchable members 50, 50 . . . is applied to the standing cuff b itself. Therefore, the standing portion b1 is able to stand in the substantially vertical direction. The surface-contacting portion b2 also stands vertically. However, since the portion corresponding to the surface-contacting portion b22 being folded back and inverted is fixed to the portion corresponding to the standing portion b11, vertical standing is limited and the surface-contacting portion b2 stands facing outward and keeping the standing force in the vertical direction. As a result, the surface-contacting portion b2 always fits flat around the wearer's leg.

The space formed between the standing portions b1, b1 forms a pocket space for enclosing urine and loose feces. When they are captured in the pocket space, the urine is absorbed into the absorbent AB through the liquid pervious top sheet 11, and the solid component of the loose feces is prevented from flowing beyond the standing cuff b due to its standing portion b1, b1 as barriers. If the urine and the liquid component of the loose feces should flow beyond the distal edge of the standing portion b1, the surface-contacting portion b2 functions as a stopper against the side-leakage.

In this embodiment, at the opposite sides of absorbent AB and within the laterally inboard portion with respect to the base line of standing, stretchable members 60 for lifting are fixed in their stretched state.

In this embodiment as shown, the stretchable members 60 for lifting are disposed between the liquid impervious back sheet 12 and the absorbent AB.

Further, in a plane view, as clearly shown in FIG. 2, in each leg portion of the diaper, the stretchable member 60 for lifting is not superposed on the constricted portion of the absorbent core 13, while in front end and back end of the diaper, it is superposed on the laterally extended portions of the absorbent core 13.

By providing such stretchable members 60 for lifting, as shown in FIG. 3, when the diaper is worn, due to the constriction force by the stretchable members 60 for lifting (the direction of force is shown in a white arrow), the opposite sides of absorbent AB are deformed so as to stand toward the wearer. In addition to this standing of the opposite sides of absorbent AB, the standing cuffs b stand from the base lines of standing, which are disposed laterally outboard with respect to the stretchable members 60 for lifting. This means that the diaper's standing is high enough to obtain a deeper pocket space, thus, the garment fit of diaper is improved sufficiently. As a result, by utilizing only standing cuffs b, the side-leakage can be surely prevented.

Further, in the front body F and back body B, in order to improve the garment fit of waist area, waist stretchable members 20F, 20F . . . and 20B, 20B . . . are provided between non-woven fabrics of overall sheet 1 and at the portions formed by folding back a sheet on the backside of overall sheet 1 at its front and back ends. Each waist stretchable member is defined by an rubber thread of small diameter. The waist stretchable members 20F, 20F . . . and 20B, 20B . . . are arranged and fixed so as to be spaced each other in the lengthwise direction and parallel to waist opening's edges and in their stretched state. The interval of waist stretchable members 20F, 20F and 20B, 20B and their number may be determined suitably, for example, it is preferable that the interval is about 4 to 6 mm and the number is 5 to 7.

Now, according to the present invention, in the diaper having the foregoing configuration, under-waist stretchable members 21F, 21F . . . are provided along the waist circumference fastening direction (It is parallel to the waist opening's edge. The same shall apply hereinafter.) within the under-waist area in the front body. On the other hand, buttock stretchable members 21B, 21B . . . are provided along the fastening direction of diaper within the buttock area in the back body. This buttock area is corresponding to that under-waist area in configuration. Then, the under-waist stretchable members 21F, 21F . . . are provided from the joint 30 on one side to the joint 30 on the other side, while they are discontinuous at the part of a range having the crosswise length corresponding to the width of absorbent AB. On the other hand, the buttock stretchable members 21B, 21B . . . are extended without any discontinuous part from the joint 30 on one side to the joint 30 on the other side. Then, the under-waist stretchable members 21F, 21F . . . are continued to the buttock stretchable members 21B, 21B . . . , respectively. This is done by connecting the side ends of buttock stretchable members 21B, 21B . . . with the side ends of under-waist stretchable members being opposite to the ends of the above part where the under-waist stretchable members are discontinuous.

In the under-waist stretchable members 21F, 21F . . . in the front body F and in the buttock stretchable members 21B, 21B . . . in the back body B, each member is defined by rubber thread of small diameter. Further, this rubber thread is arranged and fixed between the nonwoven fabrics of overall sheet 1 on the flat-out state of diaper in its stretched state. Then, in the embodiment shown in FIG. 1, the number of under-waist stretchable member 21F and the number of buttock stretchable member 21B are 9 to 25. The interval of under-waist stretchable members 21F, 21F is determined so as to be the same as or smaller than that of waist stretchable members 20F, 20F and 20B, 20B.

Additionally, in each rubber thread used for the under-waist stretchable members 21F and the buttock stretchable members 21B, its stretching stress and outer diameter of its cross section are smaller or substantially the same as those of each rubber thread used for the waist stretchable member 20F and 20B. For simplicity of the configuration of diaper, completely identical rubber thread may be used for the all stretchable members 21F, 21B, 20F and 20B. However, besides the stretching stress and the outer diameter of cross section, some other properties such as difference of color can be used for distinction. Concretely, the stretching stress of each rubber thread of small diameter is preferably 4 to 17 g, more preferably 5 to 10 g under the extensibility of 150%, while the outer diameter of its cross section is preferably 100 to 350 μm, more preferably 120 to 270 μm.

As explained above, the under-waist stretchable members 21F, 21F . . . are provided from the joint 30 on one side to the joint 30 on the other side, while they are discontinuous at the part of range over the absorbent AB. Precisely, these members 21F, 21F . . . are discontinuous over the absorbent AB, which decreases the constriction force caused by the stretchable members along the fastening direction in the girth area. On the contrary, in a conventional diaper, since under-waist stretchable members are extended so as to be continuous over an absorbent, constriction force is caused by the stretchable members. Accordingly, the diaper is shirred there so as to form longitudinal creases along the fastening direction of diaper. These creases make the absorbent lift up above the wearer's skin, which causes leak from the girth area. In this respect, in the present invention, such problem can be prevented, because the under-waist stretchable members 21F, 21F . . . are extended so as to be discontinuous over the absorbent AB. On the other hand, the buttock stretchable members 21B, 21B . . . are extended without any discontinuous part from the joint 30 on one side to the joint 30 on the other side. Accordingly, the present diaper has sufficient effect for preventing it from slipping down and for keeping the tight contact between itself and the wearer's skin. Further, since there are very few creases at the part where the under-waist stretchable members 21F, 1F . . . are discontinuous, when a clothes such as pants is put on over the diaper, good garment fit between the clothes and the diaper and neat appearance can be obtained. In another embodiment of disposable diaper of pant type (not shown), the under-waist stretchable members 21F, 21F . . . are provided from the joint 30 on one side to the joint 30 on the other side, while they are removed completely at the part of range having the crosswise length corresponding to the width of absorbent AB. Also in this case, the above effects can be attained.

Figure 5:
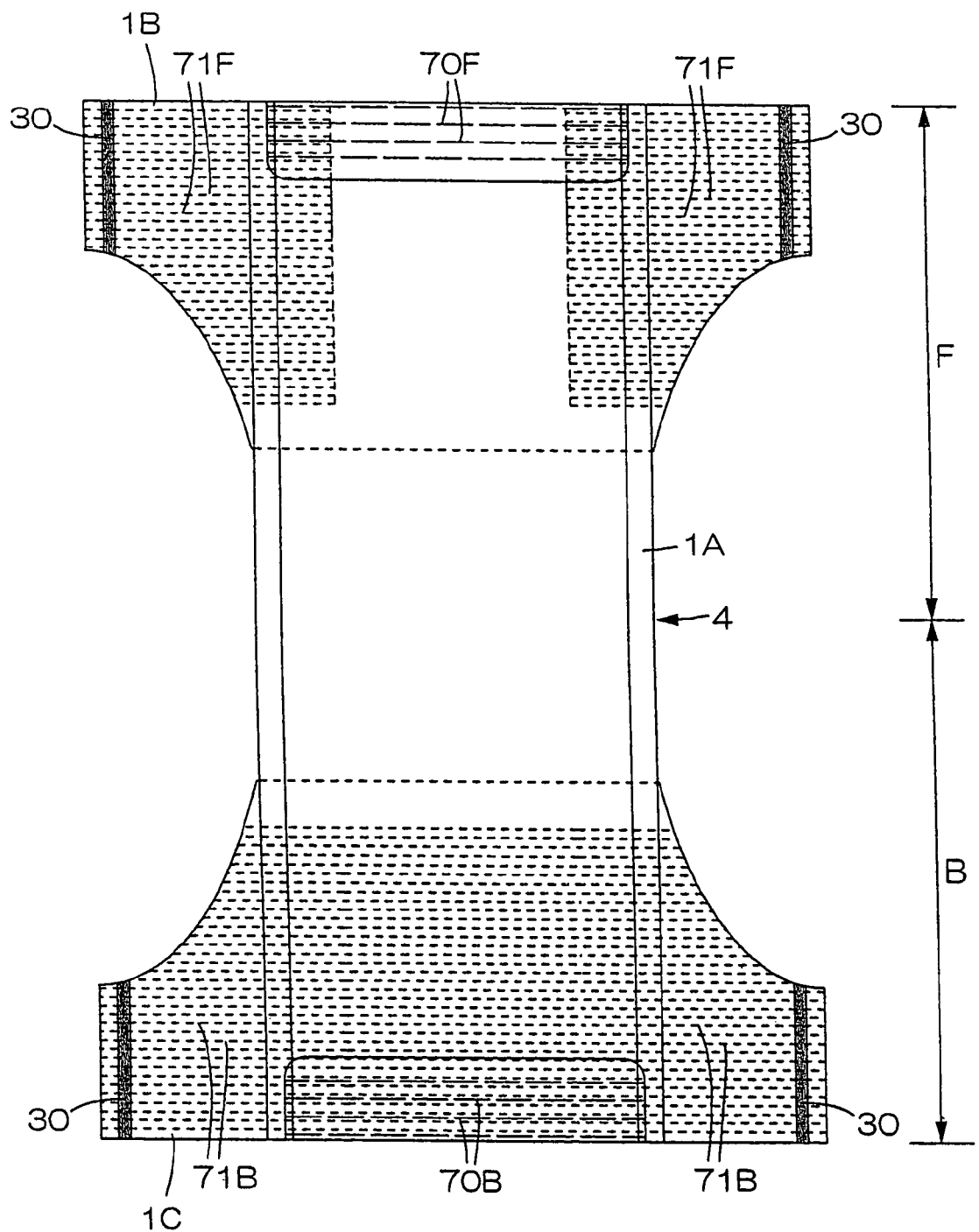
FIG. 5 is a plan view of the diaper (outer surface) in accordance with a modified embodiment when the diaper is in its flat-out state.

Now, referring to FIG. 5, further another embodiment according to claim 1 is explained. This paper diaper comprises, a structural overall sheet 1A, which has larger width than that of absorbent main body 10, a front body girth sheet 1B, which forms a front body except a diaper bottom 4, and a back body girth sheet 1C, which forms a back body except the diaper bottom 4. Then, these sheets 1A, 1B and 1C are laminated and fixed.

A plurality of waist stretchable members 70F, 70F . . . and 70B, 70B . . . are arranged and fixed on the flat-out state of structural overall sheet 1A so as to be spaced each other in the lengthwise direction. They are parallel to waist opening's edges and they stretch with elasticity. In opposite side portions of front body girth sheet 1B, a large number of stretchable members 71F, 71F . . . are fixed on the flat-out state of diaper in their stretched state. Each stretchable member 71F of one side portion is not connected to each stretchable member 71F of the other side portion. On the other hand, in the back body girth sheet 1C, stretchable members 71B, 71B . . . are arranged and fixed so as to be extended without any discontinuous part from a joint 30 on one side to a joint 30 on the other side. In this case, the portion of these stretchable members which is continuous to waist stretchable members is considered to be part of the waist stretchable members functionally and conceptually. The diaper of this kind can be also involved in the diaper in accordance with Claim 1 of the present invention.

[Other Embodiments of Paper Diaper of Pant Type]

In the embodiments stated above, the under-waist stretchable members are provided so as to be discontinuous, while the buttock stretchable members are extended so as to be continuous. On the contrary, in another embodiment of paper diaper, the under-waist stretchable members are extended without any discontinuous part from a joint on one side to a joint on the other side, while the buttock stretchable members are provided so as to be discontinuous or so as to be removed completely at the part of range having the crosswise length corresponding to the width of absorbent. Alternatively, in further other embodiments of paper diaper, as shown in the following embodiments, the both of under-waist stretchable members and buttock stretchable members are provided so as to be discontinuous at the part of or at the whole of ranges having the crosswise length corresponding to the width of absorbent, respectively.

Figure 42:
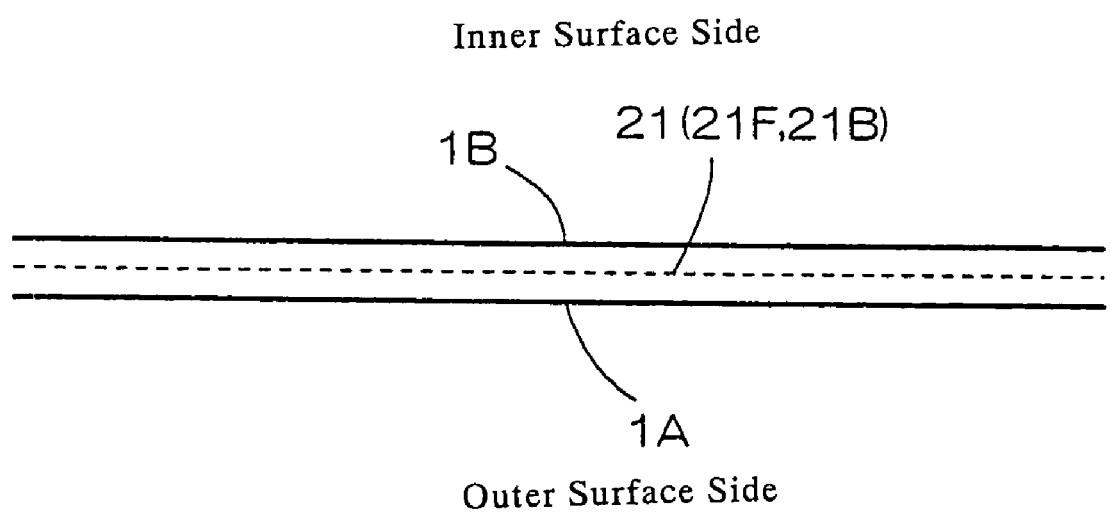
FIGS. 42 to 55 are views for explaining the embodiments of the present invention.

As shown schematically in FIG. 42, at ends in the lengthwise direction of front body F and back body B, in order to improve the garment fit of waist area W, waist stretchable members 20F, 20F . . . and 20B, 20B . . . are provided so as to be spaced each other in the lengthwise direction and parallel to waist opening's edge. Each waist stretchable member is defined by an rubber thread of small diameter. Then, the waist stretchable members 20F, 20F . . . , 20B, 20B . . . are fixed with e.g. hot melt adhesive between nonwoven fabrics 1A, 1B, on the flat-out state of diaper in their stretched state. The interval of waist stretchable members 20F, 20F and 20B, 20B and their number may be determined suitably, for example, it is preferable that the interval is about 4 to 7 mm and the number is 4 to 10.

In such configuration, under-waist stretchable members 21F, 21F . . . and 21B, 21B . . . are provided along the peripheral direction of diaper within a under-waist area in its front body and within a buttock area in its back body, respectively. These under-waist stretchable members 21F, 21F . . . and 21B, 21B . . . are provided from a joint 30 on one side to a joint 30 on the other side, while they are removed completely at the part of range having the crosswise length corresponding to the width of absorbent core 13. That is to say, they are provided in only the opposite right and left side portions.

A nonwoven fabric sheet 1A on the outer surface of overall sheet 1 of diaper has the opacity of 40% or more, preferably 50% defined by JIS P 8138. The opacity can be measured with COLORIMETER manufactured by Nippon Denshoku Industries Co. Ltd. according to JIS P 8138.

Additionally, it is preferable that the nonwoven fabric sheet 1A has the weight of being 40 g/m$^2$ or less, the thickness of 0.1 mm or more and the stiffness of being 10 mm or more defined by JIS 8143. In the nonwoven fabric sheet 1A on the outer surface of overall sheet 1, by the thickness of being 0.1 mm or more, its covering power is increased, by the weight of 40 g/m$^2$ or less and the stiffness of 10 mm or more, its expansibility is increased and feeling is improved. The color of nonwoven fabric sheet 1A on the outer surface of overall sheet 1 is preferably white from the sight of clean image. The same shall apply to the nonwoven fabric sheet 1B, which is laminated to the inner side of nonwoven fabric sheet 1A.

In this embodiment, as the under-waist stretchable member 21F, 21B, rubber thread of small diameter is used. Concretely, it is of 925 dtex or less, preferably of 620 dtex or less. Then, the color of under-waist stretchable member 21F, 21B is preferably white as is the case of the nonwoven fabric sheet 1A. If desired, the stretchable member is formed to be transparent or translucent, for example, its transparency is 50% or more. By doing so, it is preferable because the transparent or translucent stretchable member is inconspicuous.

The under-waist stretchable members 21F, 21F . . . and 21B, 21B . . . are arranged and fixed between the nonwoven fabric sheets of overall sheet 1 so as to be parallel each other in the front body F and back body B, respectively. Then, the interval of under-waist stretchable members 21F, 21F and 21B, 21B in the direction toward the diaper bottom 4 is preferably 7.0 mm or less, more preferably 5.0 mm or less and their number is 15 to 40 in the front body and in the back body, respectively. It is preferable that the interval of under-waist stretchable members 21F, 21F and 21B, 21B is determined so as to be the same as or smaller than that of waist stretchable members 20F, 20F and 20B, 20B.

Each rubber thread used for the under-waist stretchable member 21F, 21B may have the stretching stress and outer diameter being substantially equal to or smaller than those of rubber thread used for the waist stretchable members. Concretely, the stretching stress of each rubber thread of small diameter is preferably 4 to 17 g, more preferably 5 to 10 g under the extensibility of 150%.

In this embodiment, crotch stretchable members 23, 23 . . . are provided at the both sides in a crotch area L but they are not provided within its central portion. That is to say, they are provided in the opposite side portions of crotch area L. The crotch stretchable member 23 is, in the same manner as the waist stretchable member 21F, 21B, defined by an rubber thread of 925 dtex or less, preferably 620 dtex or less. Then, these rubber threads are arranged and fixed between nonwoven fabrics at the interval of 7 mm or less in the lengthwise direction.

[Second Embodiment of Disposable Diaper of Pants-Type]

Figure 43:
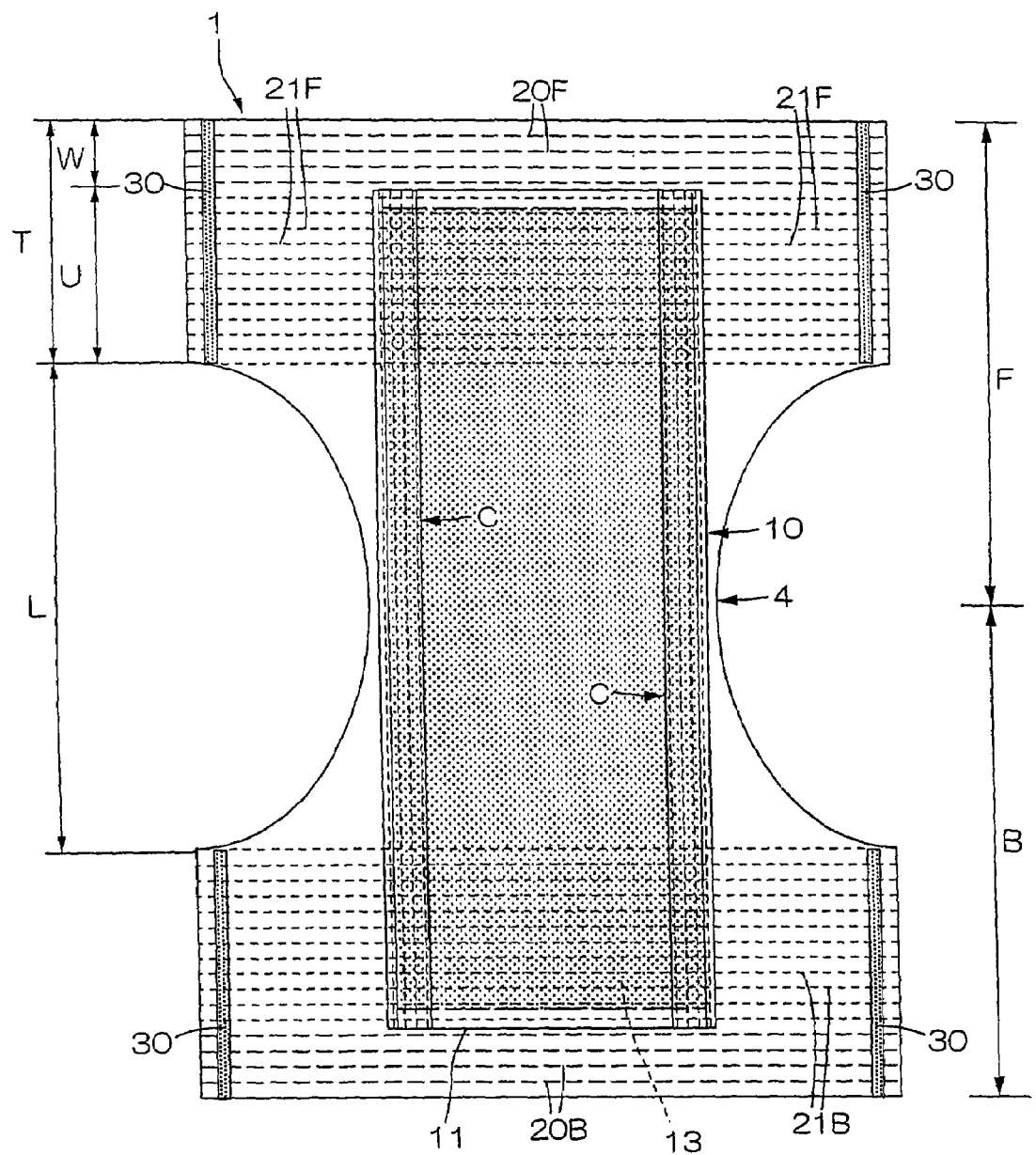
Figure 44:
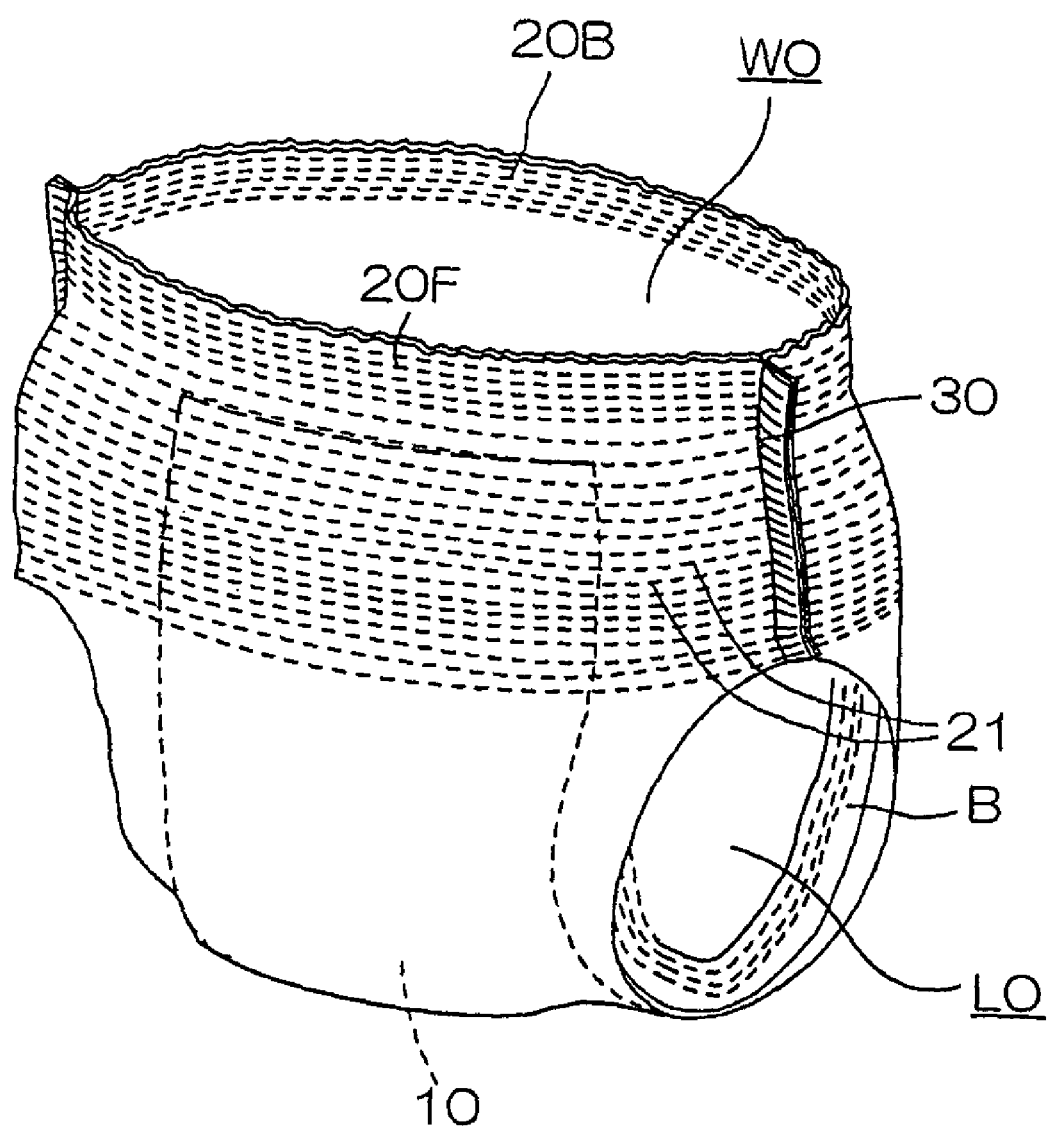

The embodiment shown in FIGS. 43 and 44 differs from the above embodiment in that there is no crotch stretchable member in a crotch area L and that under-waist stretchable members 21F, 21F . . . and 21B, 21B . . . are arranged and fixed along the peripheral direction between nonwoven fabrics so as to cross an absorbent main body 10 without any discontinuous part.

Figure 45:
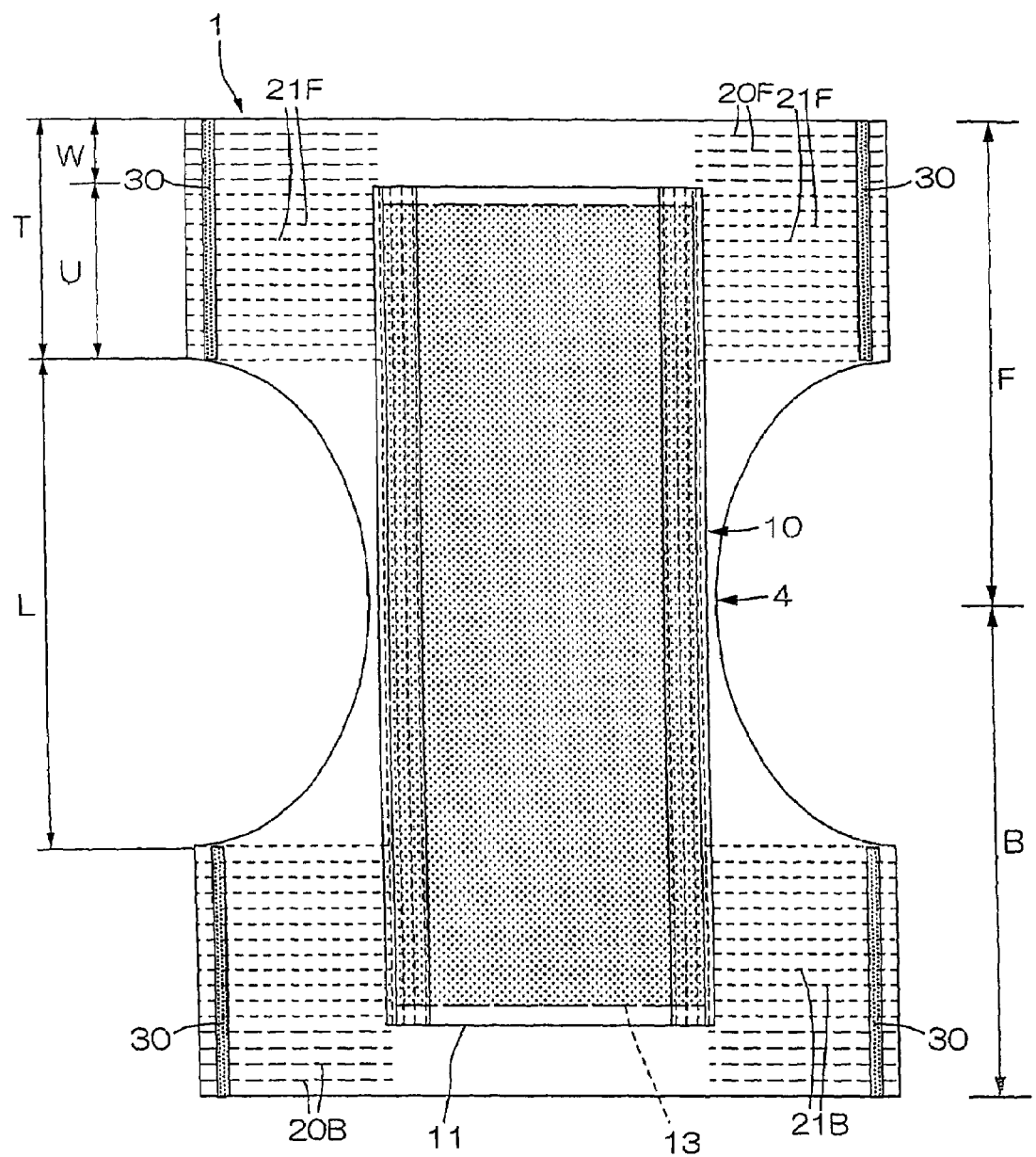
Figure 46:
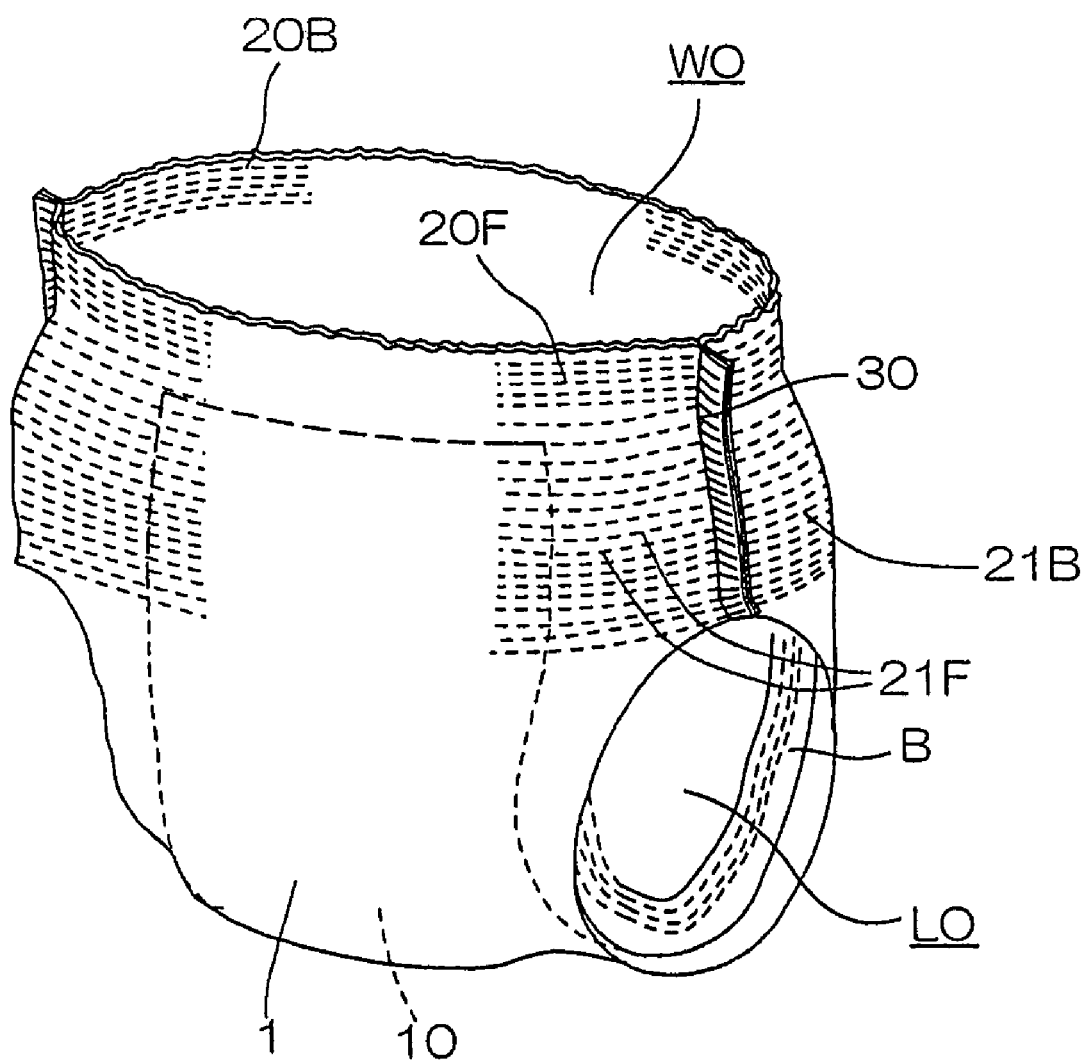

The embodiment shown in FIGS. 45 and 46 differs from the above embodiment in that there is no crotch stretchable member and that under-waist stretchable members 21F and 21B are fixed on only opposite side portions but they are not provided in a central portion.

Figure 47:
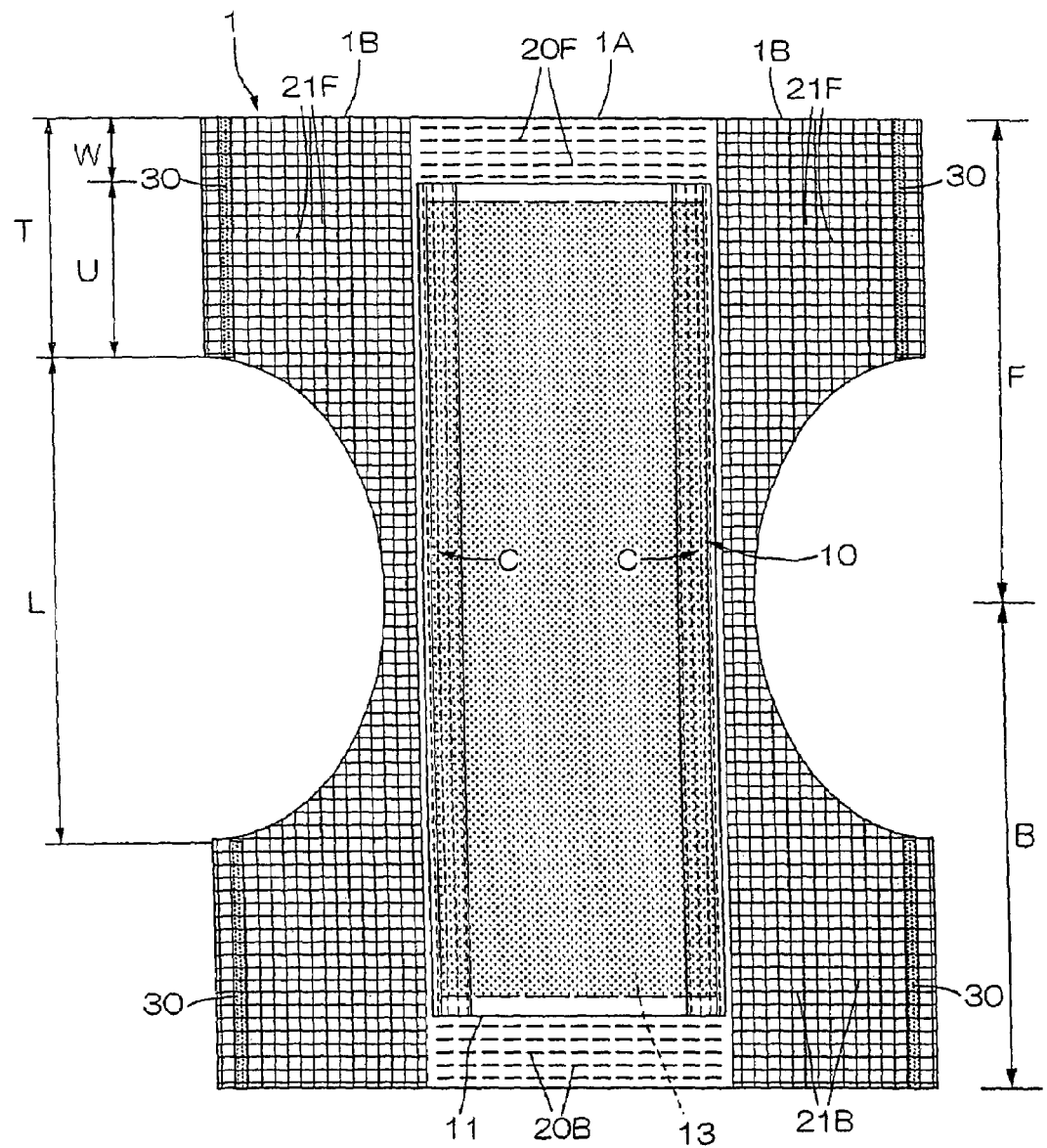

FIG. 47 shows a diaper having an overall sheet 1, which comprises a middle sheet 1A on the lengthwise direction and opposite side sheets 1B, 1B. Then, in the side sheet 1B, rubber threads are fixed between nonwoven fabrics so as to form a net-like pattern, for example a lattice pattern. The side sheets 1B, 1B are jointed to the middle sheet 1A, while the side sheets 1B, 1B are stretchable. Also in this case, the rubber threads define stretchable members within a waist area W and an under-waist area U.

Figure 48:
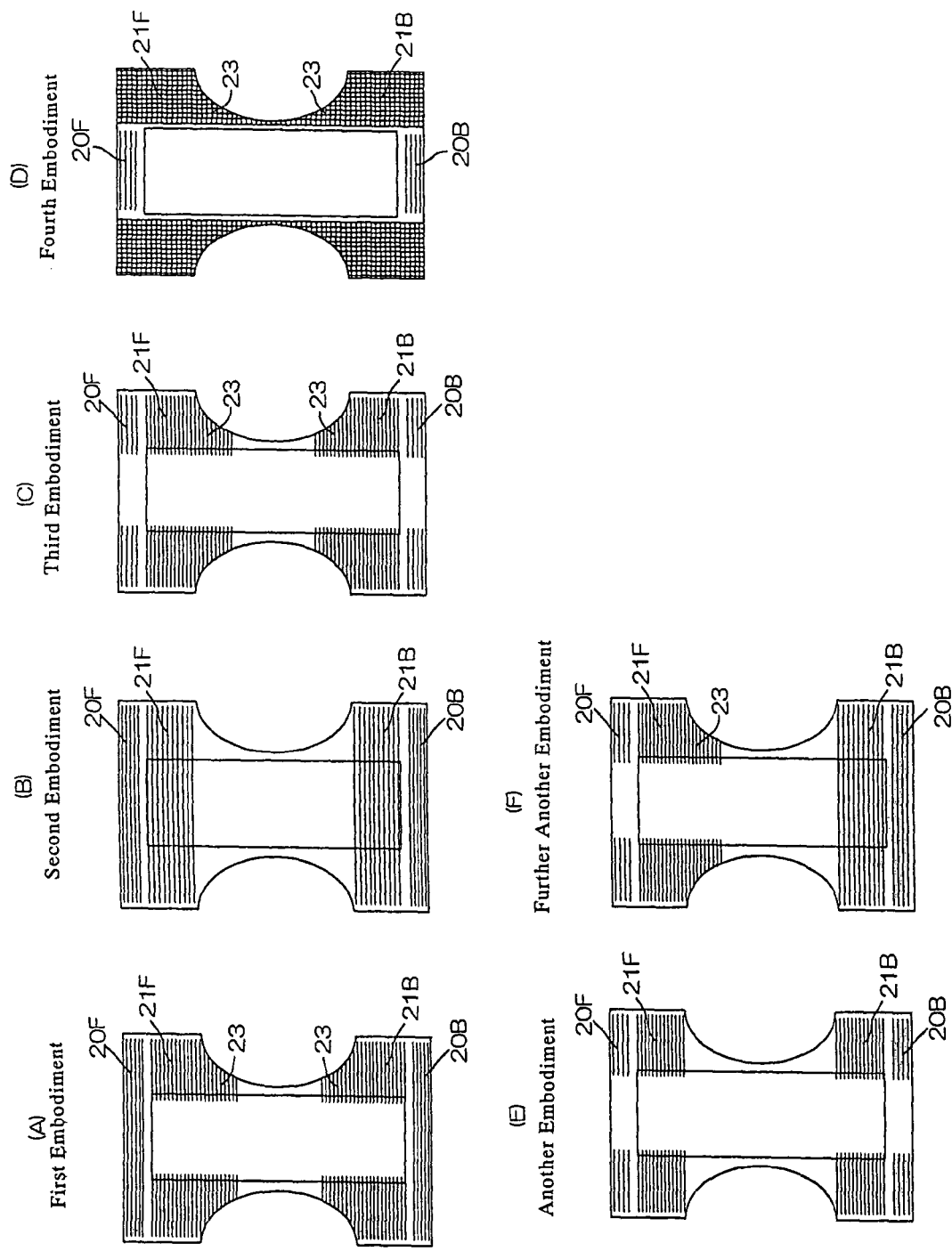

From the foregoing explanation of paper diaper in accordance with the present invention, four embodiments can be listed up conceptually, as shown in FIGS. 48(A), (B), (C) and (D). As known from these embodiments, there are two cases as for the waist stretchable members 20F, 20B and under-waist stretchable members 21F, 21B. Precisely, in the first case, they are arranged and fixed on the peripheral direction so as to cross over the absorbent main body 10 without any discontinuous part, while in the second case, they are not provided in the central portion where the absorbent core is located and they are arranged and fixed in only the opposite right and left side portions. These cases can be selected optionally. Further, there are also two cases as for the crotch stretchable members 23. Precisely, in the first case, they are provided, while in the second case, they are not provided. These cases can be selected optionally too. Additionally, there are two cases as for the arrangement of stretchable members in front body F and back body B. Precisely, in the first case, their arrangement in the front body F is the same as that in the back body B, while in the second case, their arrangement in the front body F is different from that in the back body B. These cases can be also selected optionally. Therefore, another embodiment shown in FIG. 48(E) can be selected. Precisely, the waist stretchable members 20F, 20F . . . , 20B, 20B . . . and under-waist stretchable members 21F, 21F . . . , 21B, 21B . . . are not provided in the central portion where the absorbent core 13 is located and they are arranged and fixed in only the opposite right and left side portions, as well as the crotch stretchable member 23 is not provided. Alternatively, further another embodiment shown in FIG. 48(F) can be selected. Precisely, the waist stretchable members 20F, 20F . . . and under-waist stretchable members 21F, 21F . . . in the front body are not provided in the central portion where the absorbent core 13 is located so that they are arranged and fixed in only the opposite right and left side portions, and the waist stretchable members 20B, 20B . . . and under-waist stretchable members 21B, 21B . . . in the back body are fixed so as to cross over the absorbent main body 10 without any discontinuous part as well as the crotch stretchable members 23, 23 . . . are provided in the front body F and they are not provided in the back body B. The arrangement of stretchable members can be selected optionally. When the under-waist stretchable members 21F, 21F . . . , 21B, 21B . . . or crotch stretchable members 23, 23 . . . are not provided in the central portion where the absorbent core 13 is located so that they are arranged and fixed in only the opposite right and left side portions, there are two cases as for the longitudinal centerline-side end of under-waist stretchable member 21F, 21B and the longitudinal centerline-side end of crotch stretchable member 23, respectively. Precisely, in the first case, each end is superposed on the side edge of absorbent core 13, while in the second case, each end does not reach at the side edge of absorbent core so that there is a space formed between the end and side edge.

In every paper diaper stated above, the absorbent main body 10 having the shape of rectangle is jointed to the overall sheet 1 having the shape of hourglass. As another embodiment, a liquid pervious top sheet 1 having the same shape as that of overall sheet 1 is provided and the absorbent AB is disposed between the top sheet 11 and overall sheet 1. As further another aspect, the overall sheet 1 and absorbent main body 10 are formed so as to be integral without any boundary.

The overall sheet 1 defining the outer surface of diaper is manufactured by laminating and fixing two or more than three breathable and water repellant nonwoven fabrics. However, the overall sheet 1 may be defined by one sheet of nonwoven fabric. In this case, stretchable members 20, 20 . . . , 21, 21 . . . and 23, 23 . . . may be fixed on the inner (absorbent core-side) surface of nonwoven fabric sheet. Further, a plastic sheet may be disposed between the nonwoven fabrics. Alternatively, the inner (absorbent core-side) surface of nonwoven fabric sheet for the outer surface of diaper is covered with a plastic sheet.

The under-waist stretchable members 21F, 21F . . . , 21B, 21B . . . may be arranged so as to form lattice patterns, as shown in FIG. 47. Also in this case, the stretchable members should be spaced each other at the interval in the lengthwise direction defined by the present invention.

In the embodiments, the waist stretchable members 20F, 20F . . . and under-waist stretchable members 20F, 20F . . . are provided at the range of lengthwise of 60% or more, preferably of 70% or more, and more preferably of 90% or more with respect to the range of lengthwise from waist opening's edge to the leg opening's start end. However, if the stretchable members 20F, 20F . . . , 21F, 21F . . . are provided at the range of lengthwise of 40% or less with respect to the range of lengthwise from waist opening's edge to the leg opening's start end, since the diaper can have neat appearance due to small amount of stretchable members, the stretchable members should not be spaced each other at the interval in the lengthwise direction and the thickness, which are defined by the present invention.

Figure 49:
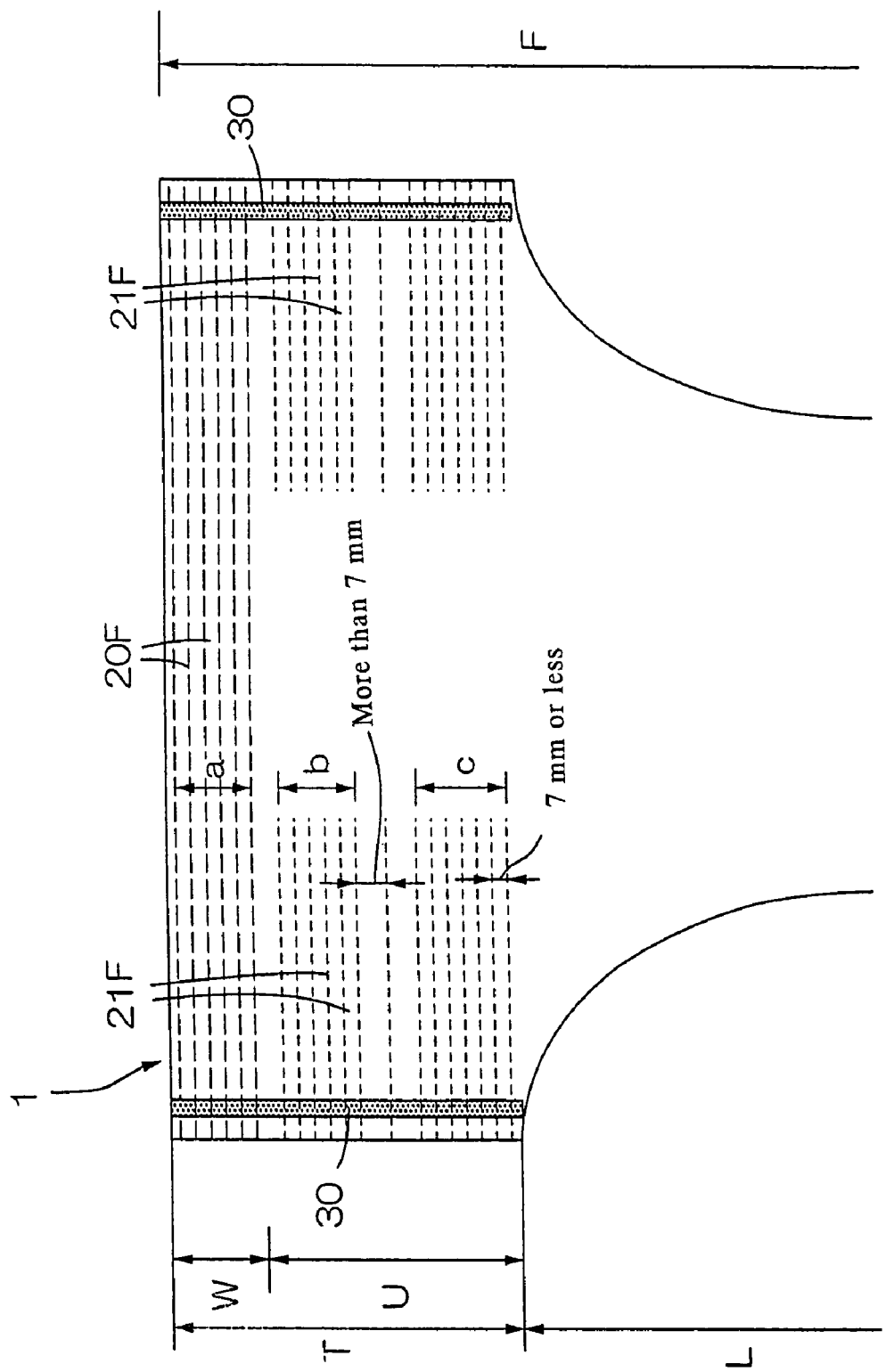

Now, referring to an enlarged view of FIG. 49, the range of lengthwise of these stretchable members 20F, 20F . . . , 21F, 21F . . . is explained concretely. First, the waist stretchable members 20F, 20F . . . are spaced each other at the interval of 7 mm or less for the range of lengthwise of a. Next, the under-waist stretchable members 21F, 21F . . . are spaced each other at the interval of 7 mm or less for the range of lengthwise of b. Finally, the under-waist stretchable members 21F, 21F . . . are spaced each other at the interval of 7 mm or less for the range of lengthwise of c. Here, between the lowermost member 21F of the range having the lengthwise of b and the uppermost member 21F of the range having the lengthwise of c, there is the interval of larger than 7 mm, which should be exclusive. As a result, it is defined that the ratio of the sum of the length of ranges having the lengthwise a, b and c to the length of girth area T (that is (a+b+c)/T) is 60% or more.

The stretchable members can be provided on the overall sheet 1 in several manners, in order to improve garment fit of diaper at its diaper bottom or crotch area.

Figure 50:
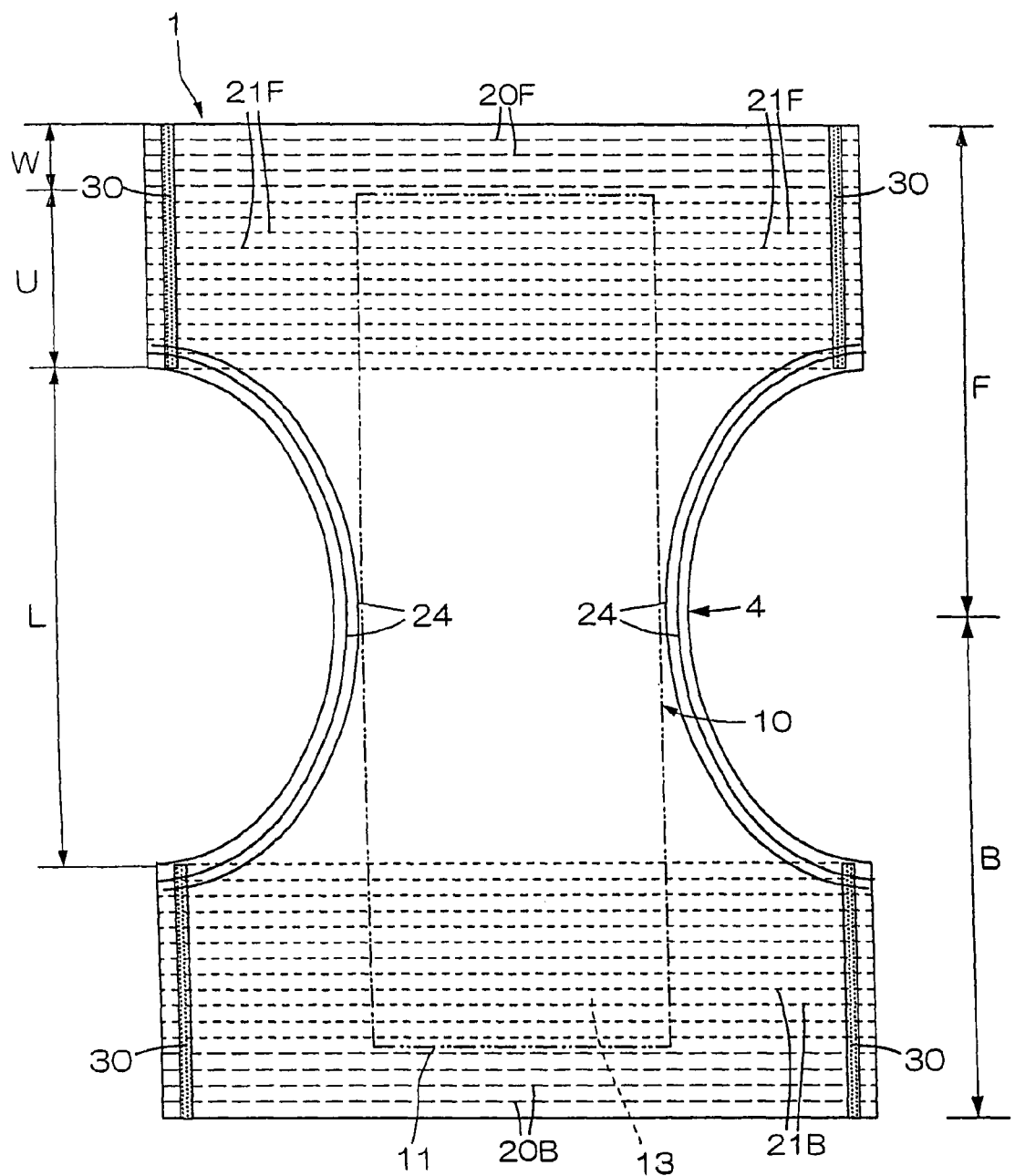

In an embodiment shown in FIG. 50, crotch stretchable members 24, 24 are fixed between the nonwoven fabrics of overall sheet 1 so as to be parallel to the leg opening's edge of leg area from the end of front side portion to the end of back side portion. In this embodiment, due to the crotch stretchable members 24, 24, the leg opening is shirred so as to prevent the leakage of body exudates. In order to show clearly the crotch stretchable members 24, 24, absorbent main body 10 is illustrated with a double dot and dash line.

Figure 51:
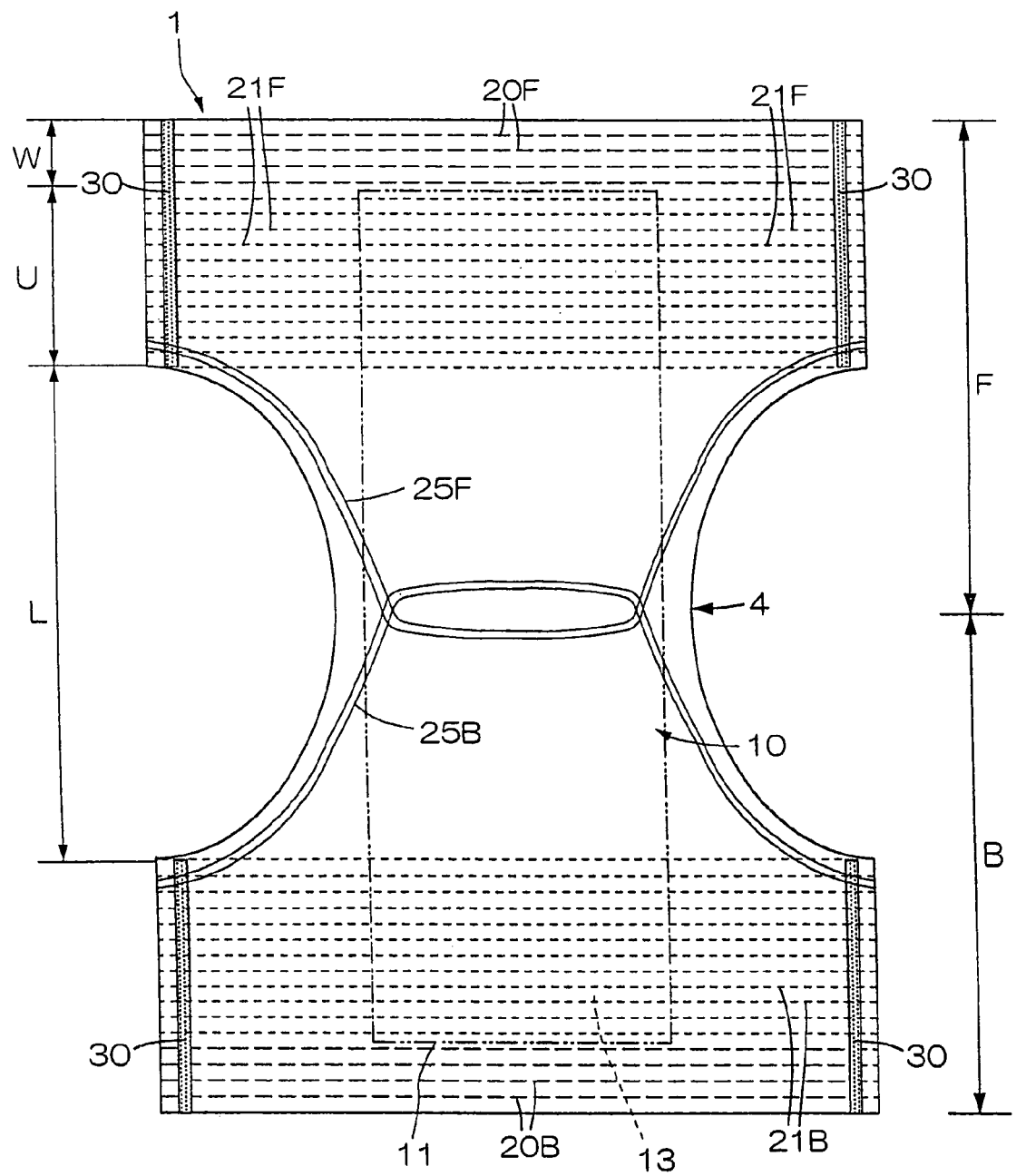

In an embodiment shown in FIG. 51, crotch and diaper bottom stretchable members 25F and 25B are fixed between nonwoven fabrics of overall sheet 1 so as to cross from the end of the side portion of one side through a diaper bottom to the end of the side portion of the other side in its front body F and back body B, respectively. In this embodiment, the crotch and diaper bottom stretchable members 25F and 25B are partly crossed each other.

Figure 52:
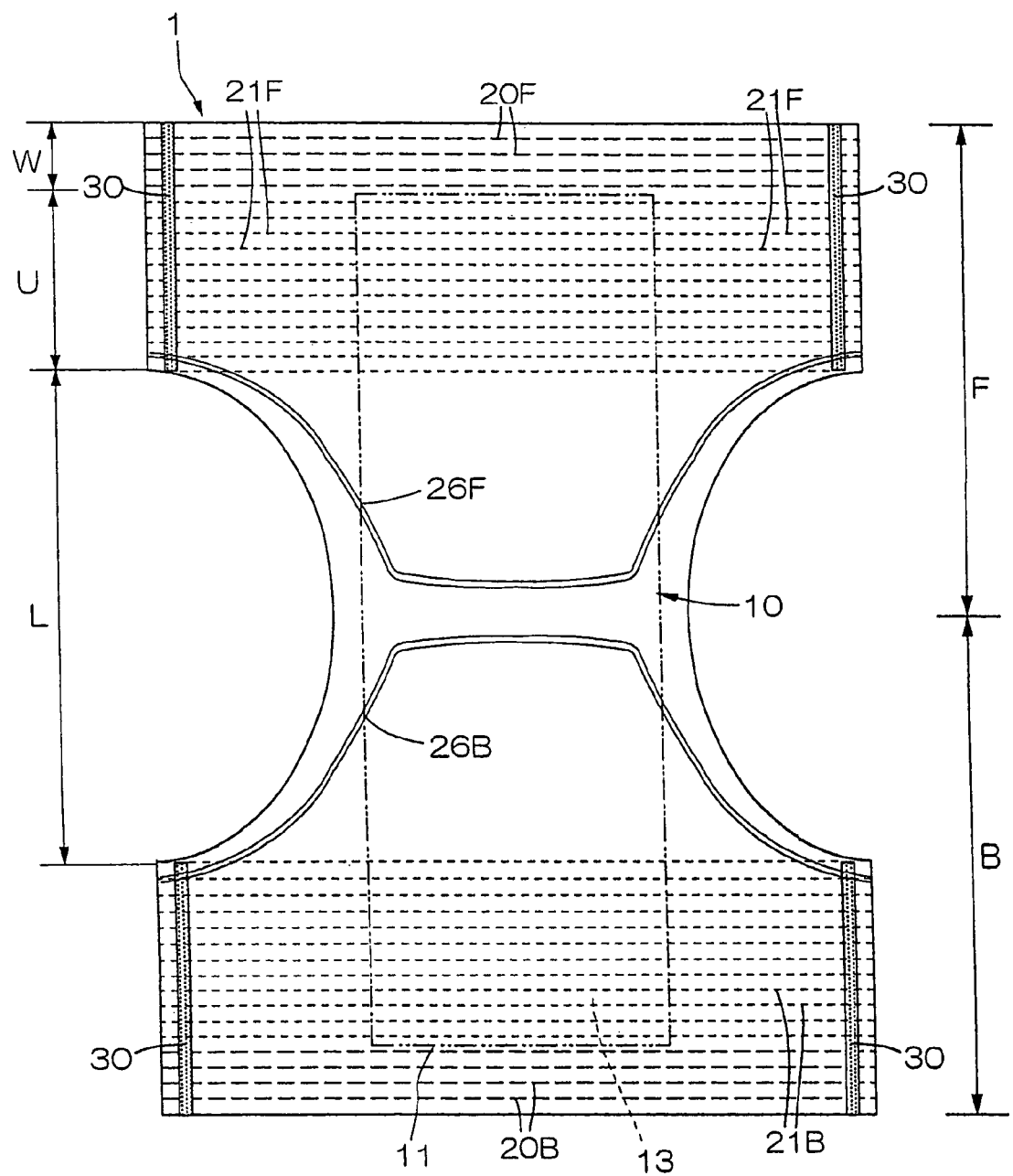

In an embodiment shown in FIG. 52, crotch and diaper bottom stretchable members 26F and 26B are fixed between nonwoven fabrics of overall sheet 1 so as to cross from the end of the side portion of one side through a diaper bottom to the end of the side portion of the other side in its front body F and back body B, respectively. In this embodiment, the crotch and diaper bottom stretchable members 25F and 25B are not crossed but parallel each other at the diaper bottom.

Figure 53:
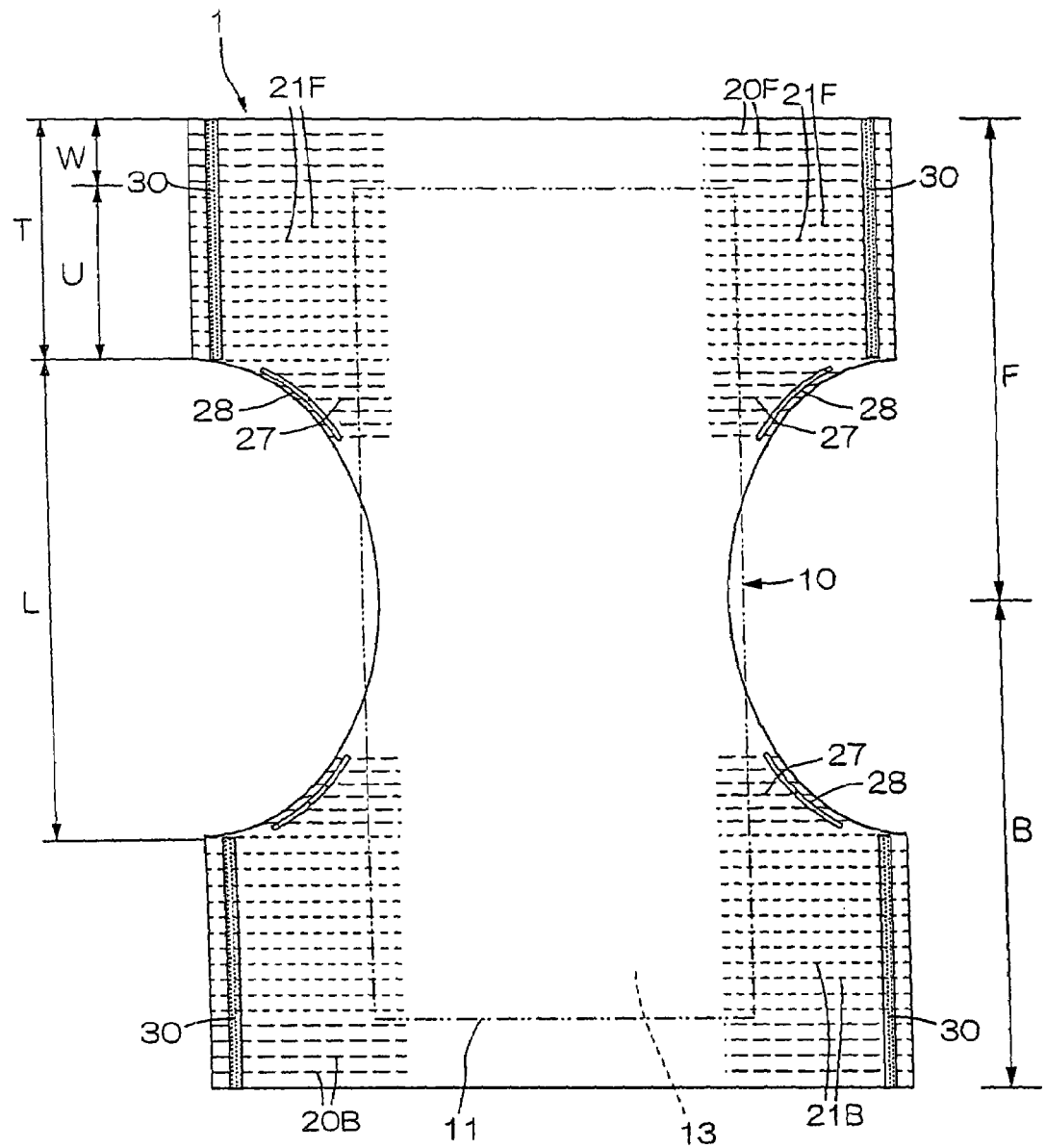

In an embodiment shown in FIG. 53, an overall sheet 1 may be formed so as to have, at its middle portion, the smaller width than that of absorbent main body 10, particularly absorbent core 13. This embodiment has another characteristic, as stated in the following. Then, this characteristic can be applied to the foregoing embodiments. The overall sheet 1 has, at its both sides, opposite portions ejecting out from the opposite side edges of absorbent core 13 so as to be often flapping, which obstructs the neat appearance of diaper. For this reason, arranging stretchable members 27, 27 . . . are provided in the same manner as the crotch stretchable member 23 in the first embodiment. By doing so, the above ejecting parts of overall sheet 1 can be shirred toward the central portion of diaper, which solves the problem related to the fluttering. Additionally, the outer ends of groups of arranging stretchable members 27, 27 . . . are fixed by seal lines 28, 28, 28 and 28 with hot melt adhesive, so that their outer ends can be prevented from being pulled into the centerline-side.

Figure 54:
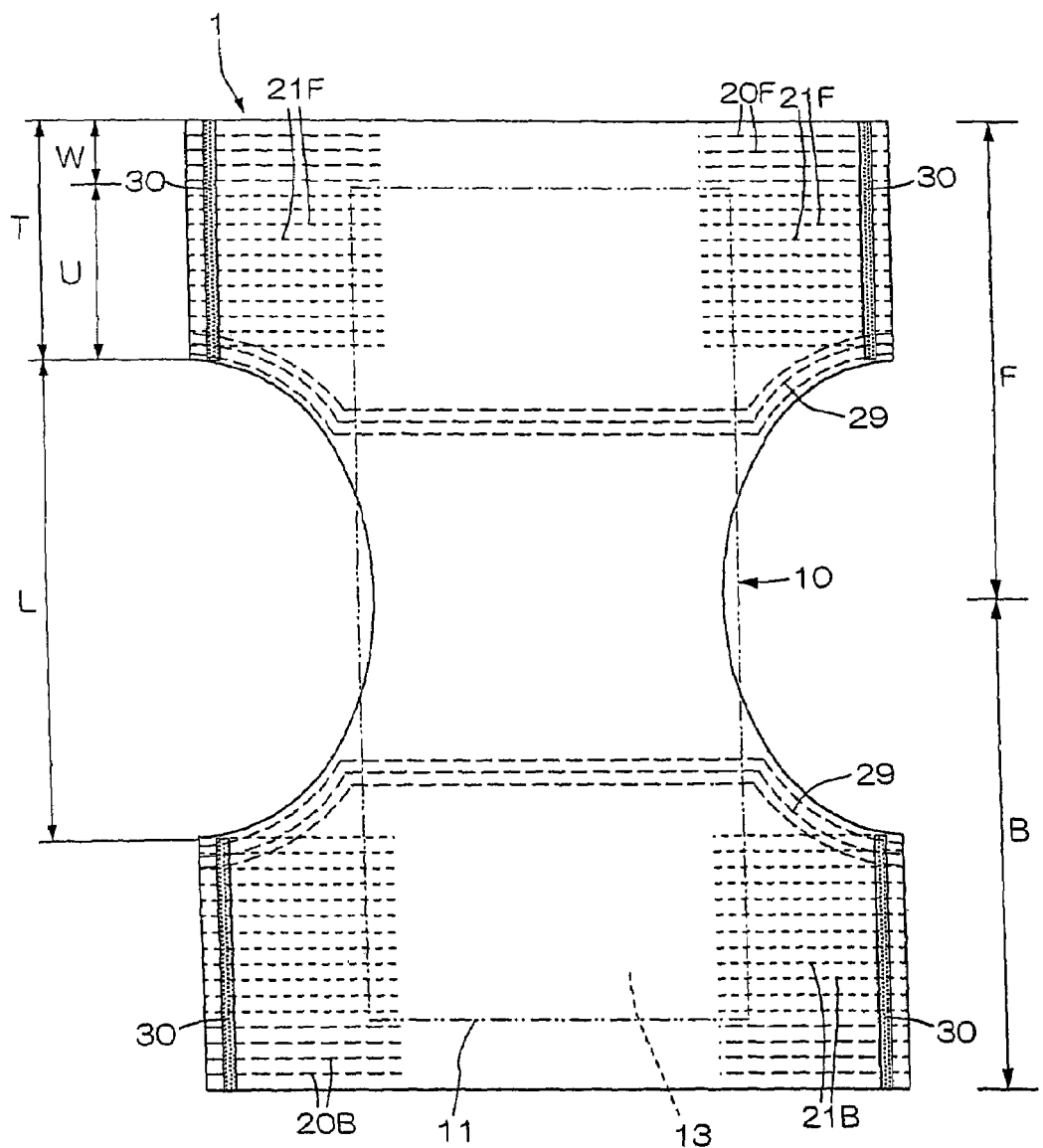

In an embodiment shown in FIG. 54, also in order to solve the problem related to fluttering, arranging stretchable members 29, 29 . . . are provided between the nonwoven fabrics of overall sheet 1 in a front body F and back body B, respectively, so as to partly go along the leg opening of one side form its start end, cross a crotch area and partly go along the leg opening of the other side to its start end. In this case, due to the almost horizontal parts in the peripheral direction of arranging stretchable members 29, 29 . . . , the ejecting parts of overall sheet 1 can be shirred toward the central portion of diaper, which solves the problem related to the fluttering. At the same time, since the arranging stretchable member 29 is provided so as to reach the end of the side portion, a crotch area can be lifted toward a girth area by the application of the arranging stretchable member 29. Thus, the looseness of diaper at its under-waist area and at its buttock area can be eliminated, resulting in the neater diaper.

[Embodiments of Diaper of Tape-Type]

Figure 55:
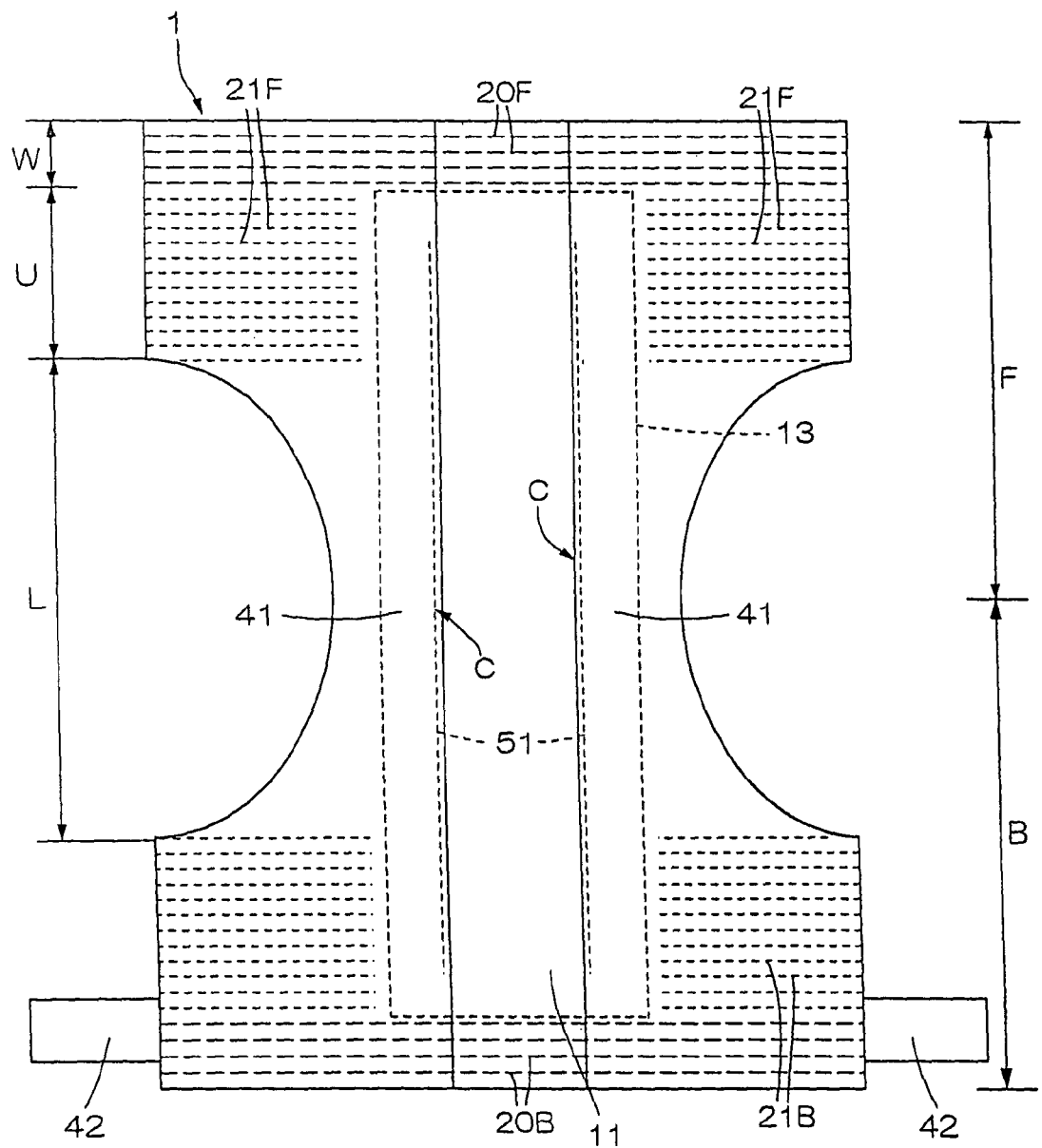

As stated above, the present invention can be applied not only a paper diaper of pants-type but also a disposable diaper of tape-type. The first embodiment of diaper of tape-type is explained referring to FIG. 55. In this embodiment, opposite standing sheets 41, 41 are provided at the both sides of diaper. Then, stretchable members are provided on the both side edges of the free standing portions of the standing sheets so as to form standing cuffs C, C. The standing sheets 41, 41 are jointed to a back sheet 1 corresponding to the overall sheet in the foregoing embodiments. The reference numeral 42 depicts tape fasteners for picking up the opposite right and left side portions of back body and jointing them to the opposite right and left side portions of front body, respectively. In this diaper, at the both ends of the front body F and back body B on the longitudinal direction, in order to improve the garment fit of waist area, waist stretchable members 20F, 20F . . . , 20B, 20B . . . are arranged and fixed between the nonwoven fabric sheets of back sheet 1. The waist stretchable member is defined by rubber thread of small diameter. Then, the rubber threads are provided so as to be spaced each other and parallel to the edge of waist opening WO. Additionally, within the under-waist area of the front body F and within the buttock area of the back body B, under-waist stretchable members 21F, 21P . . . , 21B, 21B . . . are provided along the peripheral direction in the opposite side portions, but they are removed in the central portion.

[Stretchable Member]

Figure 24:
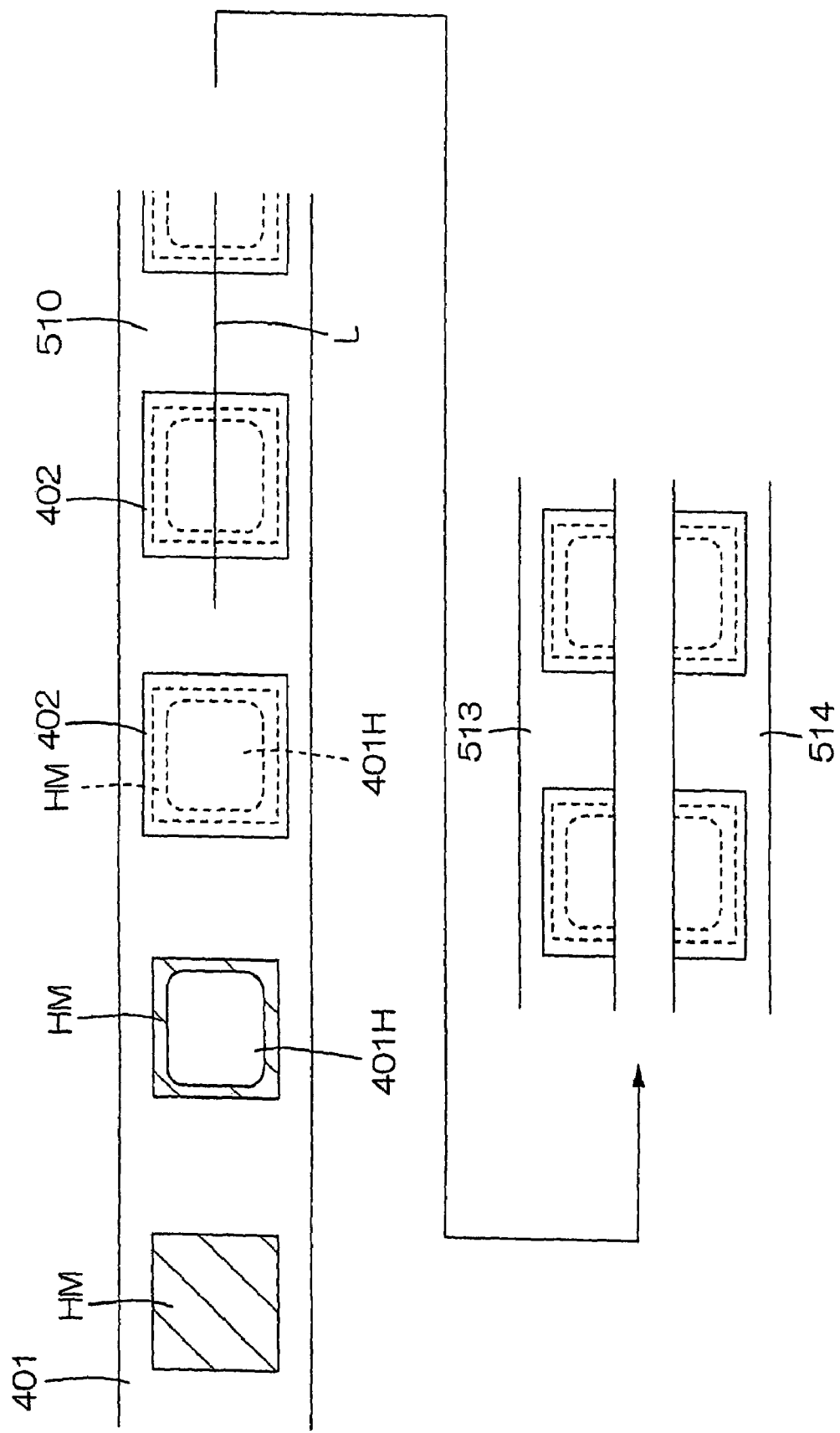
FIG. 24 is a plan view showing a step for producing an under-waist stretchable member band and a buttock stretchable member band in accordance with the modified embodiment of the second embodiment.
Figure 25:
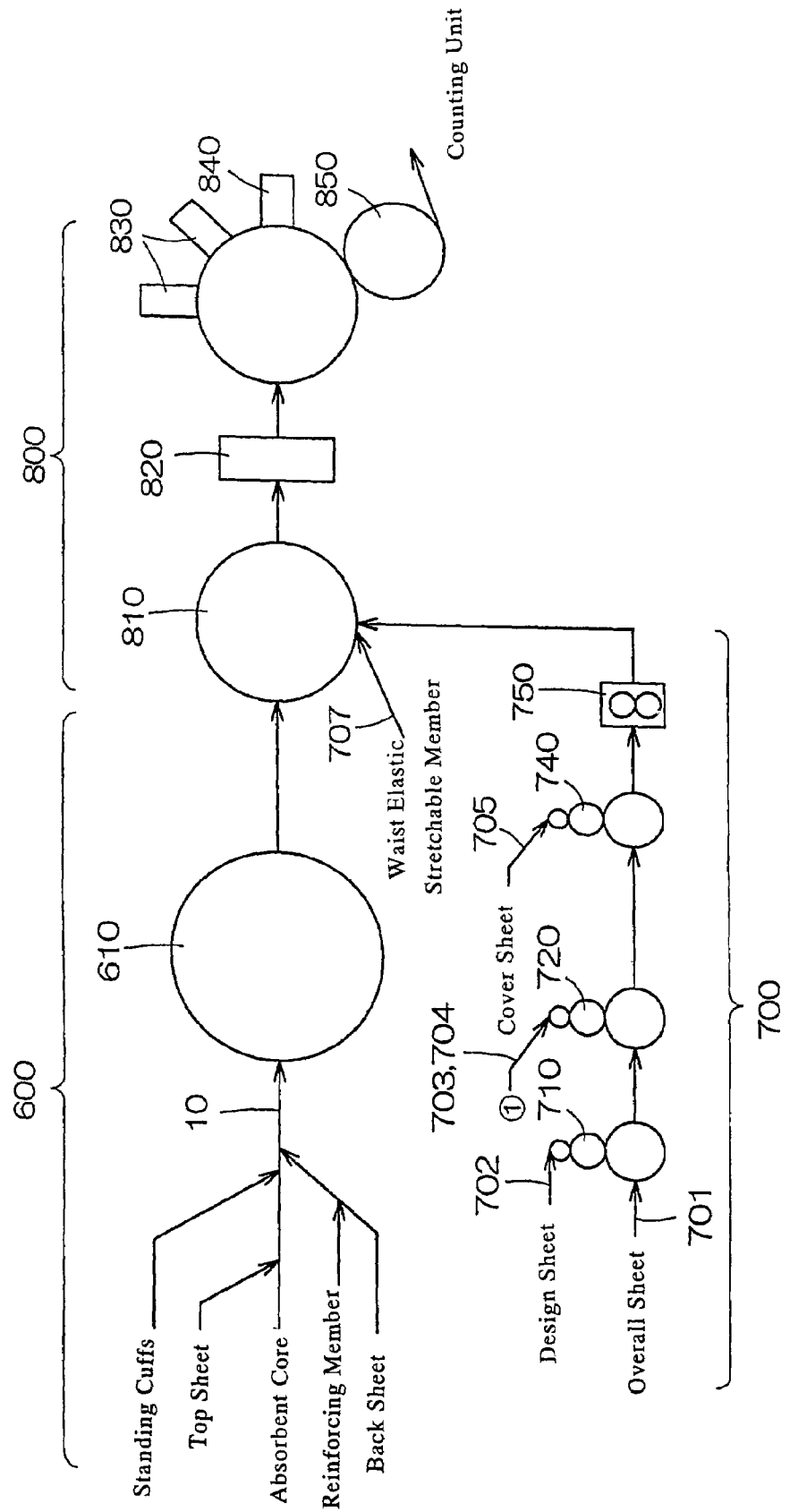
FIG. 25 is a flow diagram showing the producing line of the diaper using a method for attaching stretchable members to the diaper in accordance with the third embodiment.

The stretchable member is made from natural rubber, synthetic rubber, other materials having expansibility like urethane or the like. Then the stretchable member is used in the form of stretchable strand member or stretchable seat member having larger area. For example, there can be listed urethane belt-shaped member, film member, sheet member and the like. As the film member, imperforate film, perforate film or the like can be used. As the sheet member, sheet having net-like pattern can be used. These materials can be selected optionally. FIG. 24 shows another embodiment of arrangement of imperforate film 60, and FIG. 25 shows further another embodiment of arrangement of film 61 having net-like pattern. Also in these embodiments, it should be noted that stretchable members are provided at the range of lengthwise of 60% or more with respect to the range of lengthwise of the girth area.

<Embodiments of Method for Attaching Stretchable Members to Disposable Diaper in Producing of Diaper>

Now, are explained the embodiments of producing method of paper diaper are explained. Here, a method for attaching stretchable members to the diaper in accordance with the present invention is applied to each producing method.

First Embodiment

Figure 6:
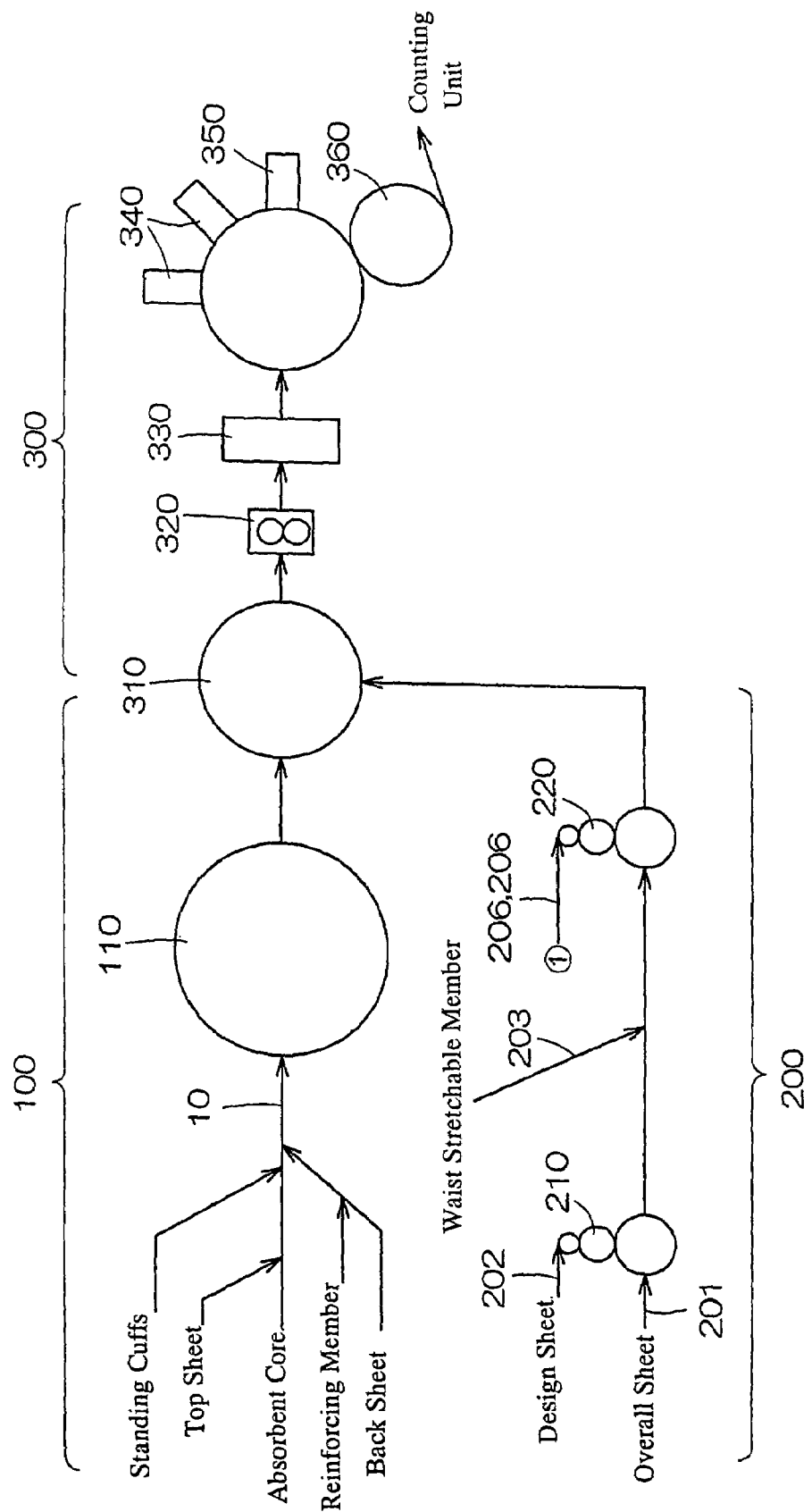
FIG. 6 is a flow diagram showing the producing line of the diaper using a method for attaching stretchable members to the diaper in accordance with the first embodiment.

FIG. 6 shows an assembling draw of paper diaper of pants-type in accordance with the first embodiment. This draw comprises an absorbent main body-producing and supplying line 100, overall sheet-producing and supplying line 200 and final process line 300.

This assembling is carried out as follows. At first, an absorbent core is supplied while its lengthwise direction is identical to its conveying direction. Next, a liquid pervious top sheet is covered and fixed on the absorbent core. Then, standing cuffs are arranged and fixed on the opposite sides of the liquid pervious top sheet. Additionally, the resultant absorbent core covered with the top sheet having the standing cuffs is arranged and fixed on a liquid impervious back sheet, which is separately supplied, so that the finished piece of absorbent main body 10 is obtained. In this embodiment, the liquid impervious back sheet 10 is previously, at the opposite side edges, folded back upon itself so as to form double portions. Then, reinforcing members such as color urethane film are adhesive-bonded between the opposite double portions. By doing so, the side edges can be flexible (Instead of reinforcing member, color hot melt adhesive-bonding is carried out so that the side edges become flexible or conspicuous).

The resultant absorbent main body 10 is turned for 90 degrees on a plane by means of 90 degrees-turn unit 110 so that the lengthwise direction of the absorbent main body 10 is perpendicular to the conveying direction. Then, this absorbent main body 10 is conveyed to an overall sheet-attaching unit 310 of the final process line 300.

On the other hand, in the overall sheet-producing and supplying line 200, under-waist stretchable members and buttock stretchable members and waist stretchable members are attached to a belt-shaped overall sheet 201, which is continuous on the crosswise direction of the diaper.

Now, explanation is carried out particularly. First, the belt-shaped overall sheet 201 is introduced into a slipping and cutting unit 210. On the other hand, a design sheet 202, which is supplied separately, is slipped into the slipping and cutting unit 210 with time-interval in supplying and cut one by one so as to form many predetermined shaped design sheets. Then, as shown in also FIG. 9, these predetermined shaped design sheets 202, 202 . . . are arranged and fixed, with e.g. hot melt adhesive, on the upper surface of belt-shaped overall sheet 201 at the central portion on the crosswise direction in the front body and at the central portion on the crosswise direction in the back body. As the design sheet, for example, an opaque film, which is provided with visible design such as pattern of animation character, can be used.

Figure 9:
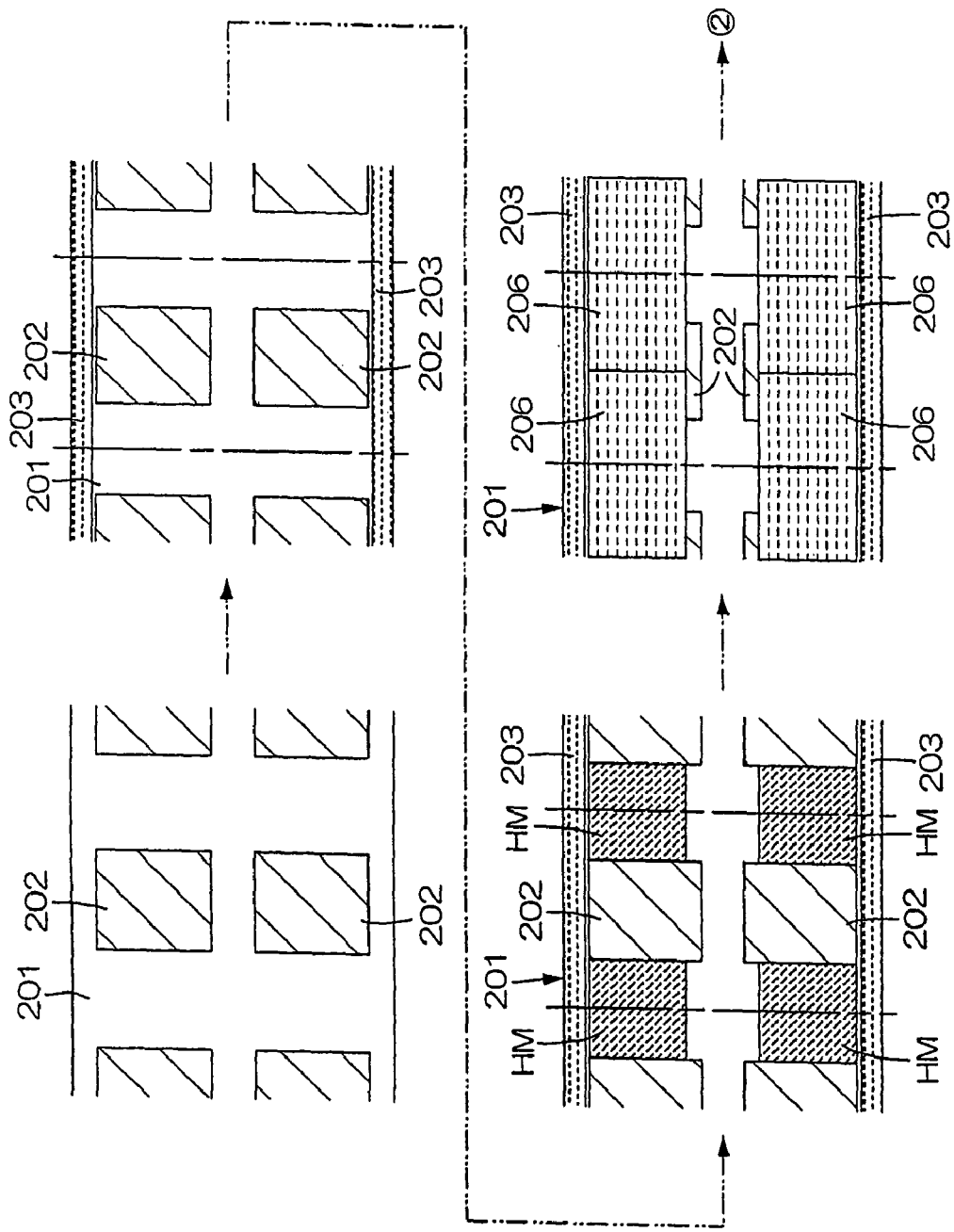
FIG. 9 is a plan view showing a producing step of the producing line of a girth stretchable member in accordance with the first embodiment.

Next, on the upper surface of the belt-shaped overall sheet 201, to which the design sheets 202, 202 . . . are attached, as shown in also FIG. 9, continuous waist stretchable members 203, 203 . . . are supplied uninterruptedly at the predetermined portions, respectively (For example, a plurality of thread-shaped elastic members or belt-shaped elastic members are supplied so as to be parallel each other at the interval). Then, the waist stretchable members 203, 203 . . . are fixed there with hot melt adhesive. Additionally, the belt-shaped overall sheet 201, to which the waist stretchable members 203, 203 . . . are attached, is introduced into a girth stretchable member-attaching unit 220, where the under-waist stretchable members and buttock stretchable members are attached, respectively in the manner according to the present invention.

Figure 7:
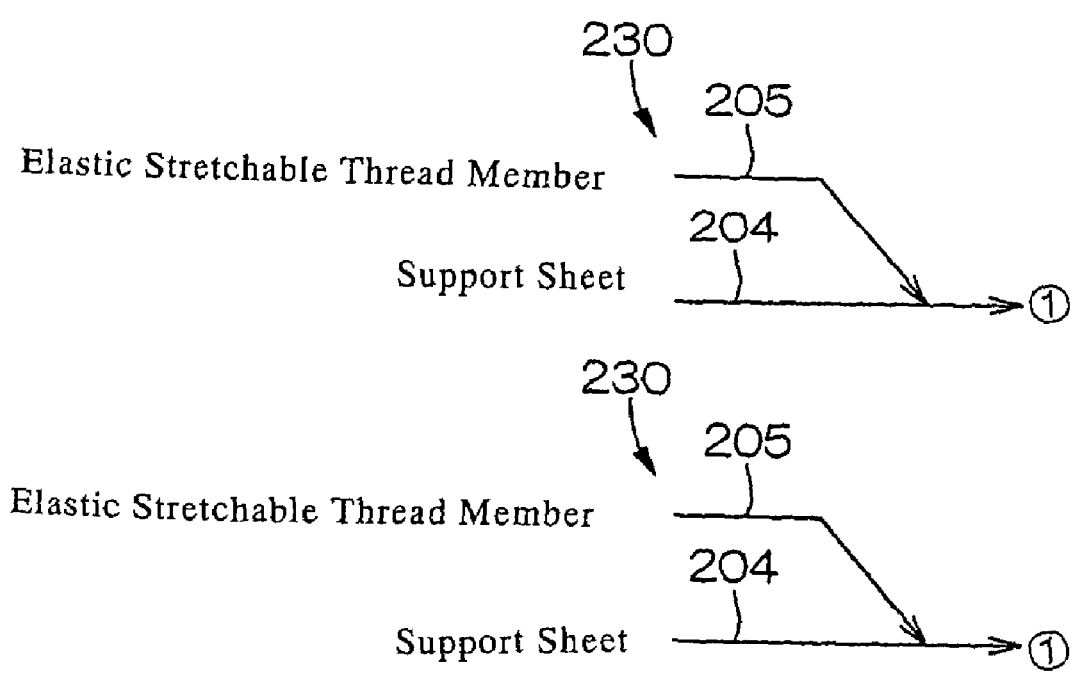
FIG. 7 shows flow diagrams indicating line ① part of FIG. 6.

Therefore, in this embodiment, as shown in FIG. 7, an under-waist stretchable member band-supplying line 230 and buttock stretchable member band-supplying line 230 are provided separately. In each supplying line 230, as shown in the upper drawing of FIG. 8, a plurality of continuous stretchable members 205 (thread-shaped elastic members, strip-shaped elastic members, belt-shaped elastic members, or the like. The same shall apply hereinafter) are arranged and fixed, with e.g. hot melt adhesive, on a belt-shaped continuous support sheet 204 so as to be spaced and parallel each other and in their stretched state, resulting in a belt-shaped continuous stretchable sheet member 206. After that, the belt-shaped continuous stretchable sheet members 206, 206 obtained from the supplying lines 230, 230 are introduced into the girth stretchable member-attaching unit 220, respectively. Alternatively, one belt-shaped continuous stretchable sheet member is formed so as to be cut longitudinally with a slitter cutter, resulting in a plurality of belt-shaped continuous stretchable sheet member, each of which is introduced into the girth stretchable member-attaching unit 220, although which is not shown.

Figure 11:
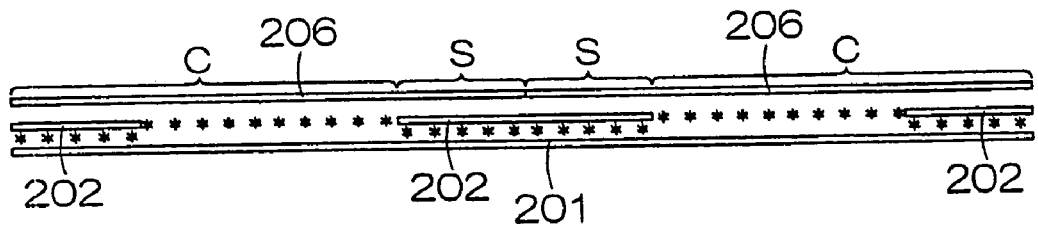
FIG. 11 is a longitudinal sectional view showing stretchable sheet members, which are attached to the diaper and before being contracted, in accordance with the first embodiment.

In the girth stretchable member-attaching unit 220, each belt-shaped stretchable sheet member 206 is cut one by one into a plurality of stretchable sheet members 206, 206 . . . of predetermined length. On the other hand, by an adhesive applying-unit (not shown), adhesive such as hot melt adhesive HM is applied intermittently to a separately introduced overall sheet 201 at its under-waist areas except their central portions and at its buttock areas except their central portions. Then, the stretchable sheet members 206, 206 . . . are arranged in the crosswise direction of diaper so as to stretch along the crosswise direction of diaper with elasticity. Additionally, the stretchable sheet members 206, 206 . . . are placed so that their attaching faces mate with the overall sheet 201. Here, each stretchable sheet member 206 is divided conceptually into three portions, central portion C and opposite side portions S, S, so that the side portion S of one stretchable member 206 is adjacent to the side portion S of the next stretchable member 206. Then, as stated above, since the adhesive HM is applied intermittently, as shown in FIG. 11, each pair of adjacent stretchable sheet members 206, 206 are adhesive-bonded to the overall sheet 201 at their two central portions C, C, while each pair of adjacent stretchable members 206, 206 are not adhesive-bonded to the overall sheet 201 at their two adjacent side portions S, S.

Figure 10:
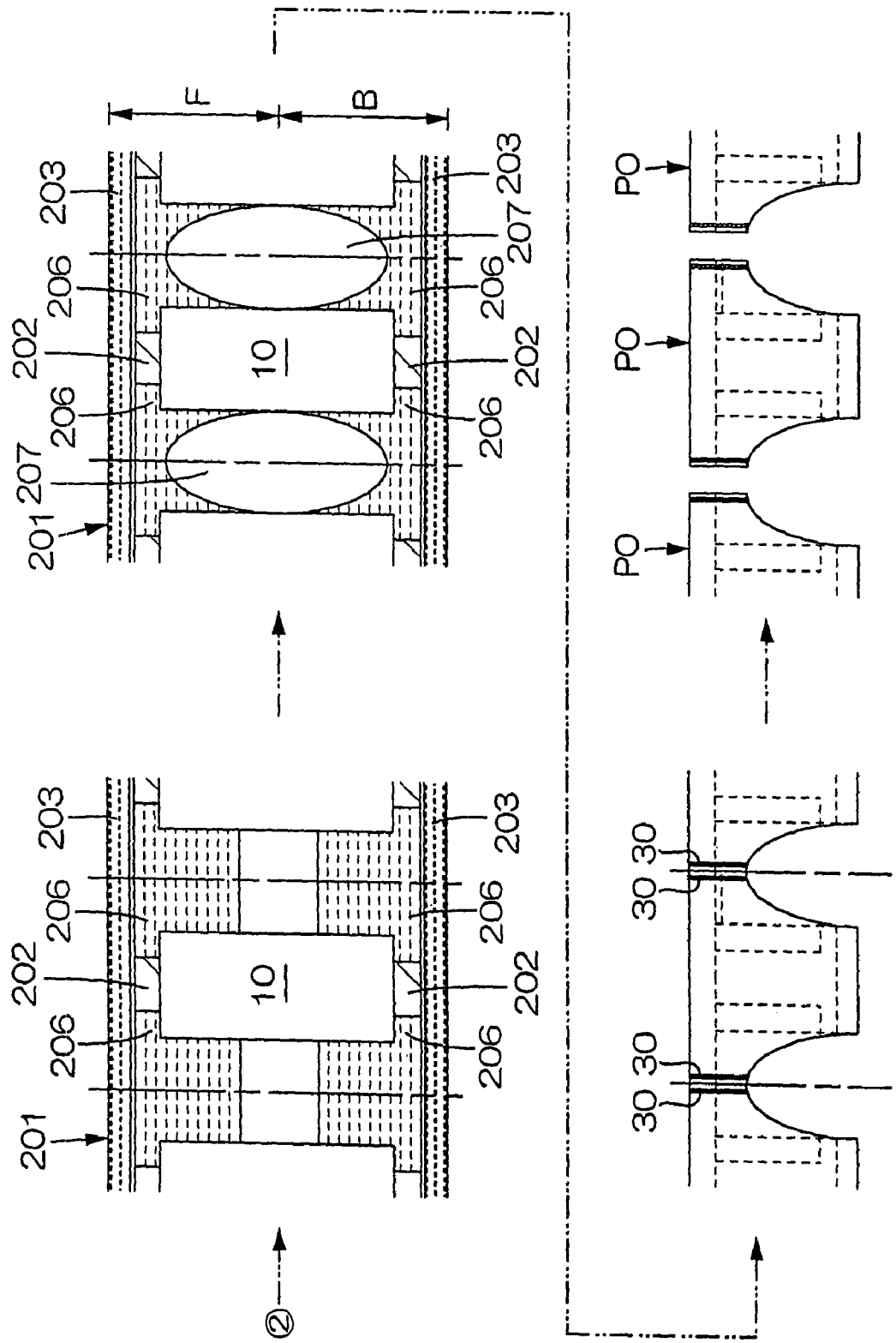
FIG. 10 is a plan view showing a producing step of the final process line in accordance with the first embodiment.
Figure 12:
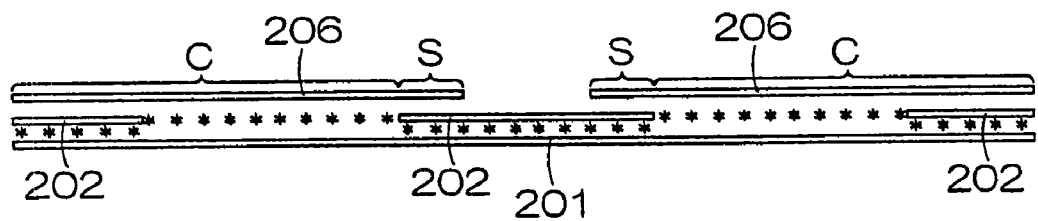
FIG. 12 is a longitudinal sectional view showing stretchable sheet members, which are contracted, in accordance with the first embodiment.

After such bonding to the overall sheet 201, these stretchable sheet members 206, 206 are released from stretching situation. Accordingly, as shown in FIGS. 10 and 12, the two adjacent side portions S, S of each pair of two adjacent stretchable sheet members 206, 206 are constricted so as to be apart from each other. Therefore, each pair of two adjacent stretchable sheet members 206, 206 attached to the overall sheet 201 are spaced each other so as to be discontinuous.

Figure 13:
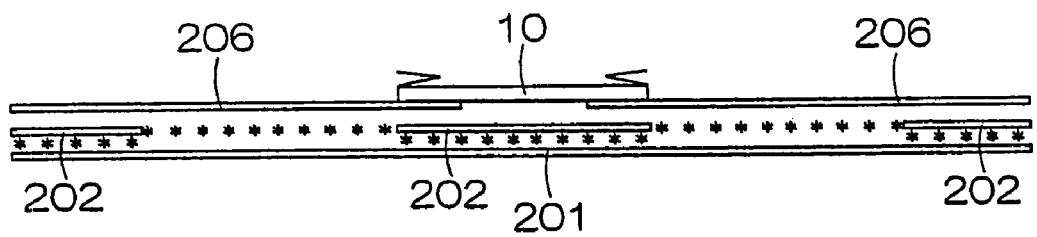
FIG. 13 is a longitudinal sectional view showing an absorbent attached to the diaper in accordance with the first embodiment.

Next, the overall sheet 201, to which the stretchable members are attached, is introduced into the overall sheet-attaching unit 310 of the final process line 300. In the overall sheet-attaching unit 310, as shown in FIGS. 10 and 13, the separately introduced absorbent main body 10 is arranged and fixed, by means of e.g. hot melt adhesive bonding, on the overall sheet 201 so as to cross over the space formed between adjacent two stretchable sheet members 206, 206.

The resultant overall sheet 201, to which the stretchable members and absorbent main body are attached, is introduced into a die cutter successively. Then, in this die cutter, the overall sheet 201 is cut so as to make holes 207, each of which is corresponding to two leg openings of two adjacent diapers. Next, the overall sheet 201 is folded up so that the opposite side edges 30, 30 of each back body B is put upon the opposite side edges 30, 30 of each front body B, respectively. Then, thus folded overall sheet 201 is introduced into a heat seal unit 340, where heat seal is carried out at the side edges 30, 30 . . . . After that, the overall sheet 201 is introduced into a final cutter 350. In this final cutter 350, first, margins provided for conveying are cut away. Then, the overall sheet is cut so as to have slit at each waist opening's edge. Additionally, the overall sheet is cut away so as to separate each other at the side edges. Further, thus separated individual piece is trimmed into a diaper PO having the predetermined size as a product. After such cutting, visible design such as pattern of animation character, mark or the like are transferred to each diaper PO by means of transfer roll 360 if desired. Finally, the diapers PO, PO . . . are introduced into a counting unit (not shown) successively.

Figure 14:
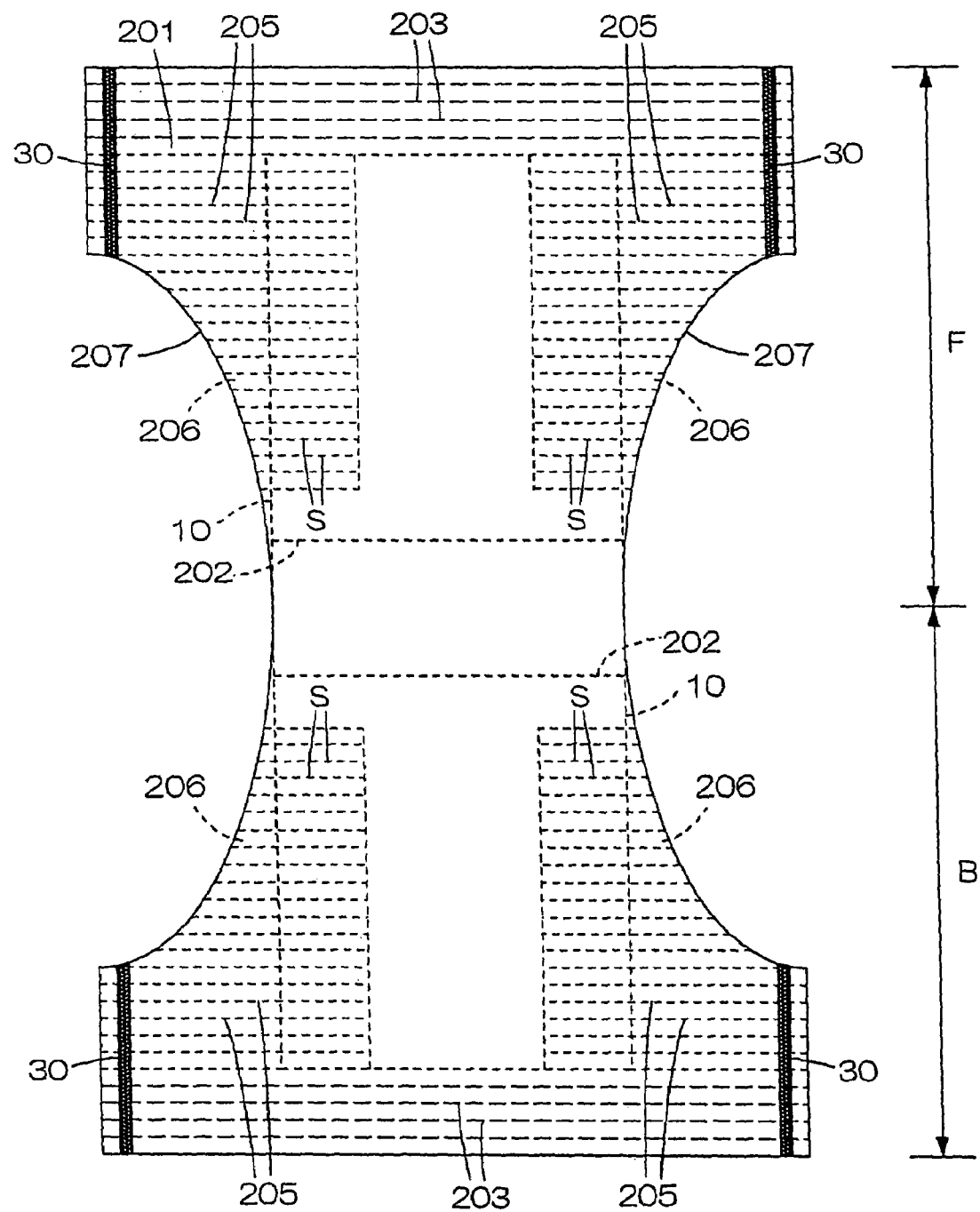
FIG. 14 is a plan view showing a disposabale diaper (outer surface) produced by a method in accordance with the first embodiment when the diaper is in its flat-out state.

In a thus produced paper diaper PO, as shown in a diaper depicted in FIG. 14 while it is in flat-out state (inner-side), in the front body F, the under-waist stretchable members 205, 205 . . . , which are included in the stretchable sheet member 206, are provided from the joint 30 of one side to the joint 30 of the other side, while they are discontinuous at the range having the central portion of crosswise length corresponding to the width of absorbent AB. Further, in the back body B, the buttock stretchable members 205, 205 . . . , which are included in the stretchable sheet member 206, are provided from the joint 30 of one side to the joint 30 of the other side, while they are discontinuous at the range having the central portion of crosswise length corresponding to the width of absorbent AB. On the other hand, in each pair of adjacent stretchable members 206, 206, the central portions C, C are attached in their stretched state while its side portions S, S, each of which is disposed at the absorbent-side, are attached so as not to stretch. Then, as shown in FIG. 14, although the side portions S, S, which are not adhesive-bonded, are superposed on the side edges of the absorbent main body, under-waist stretchable members 205 and buttock stretchable members 205 located there are not visible, because they are hidden by the design sheet.

Alternatively, the under-waist stretchable members 205, 205 and buttock stretchable members 205 are discontinuous at the range having the whole of crosswise length corresponding to the absorbent.

Figure 8:
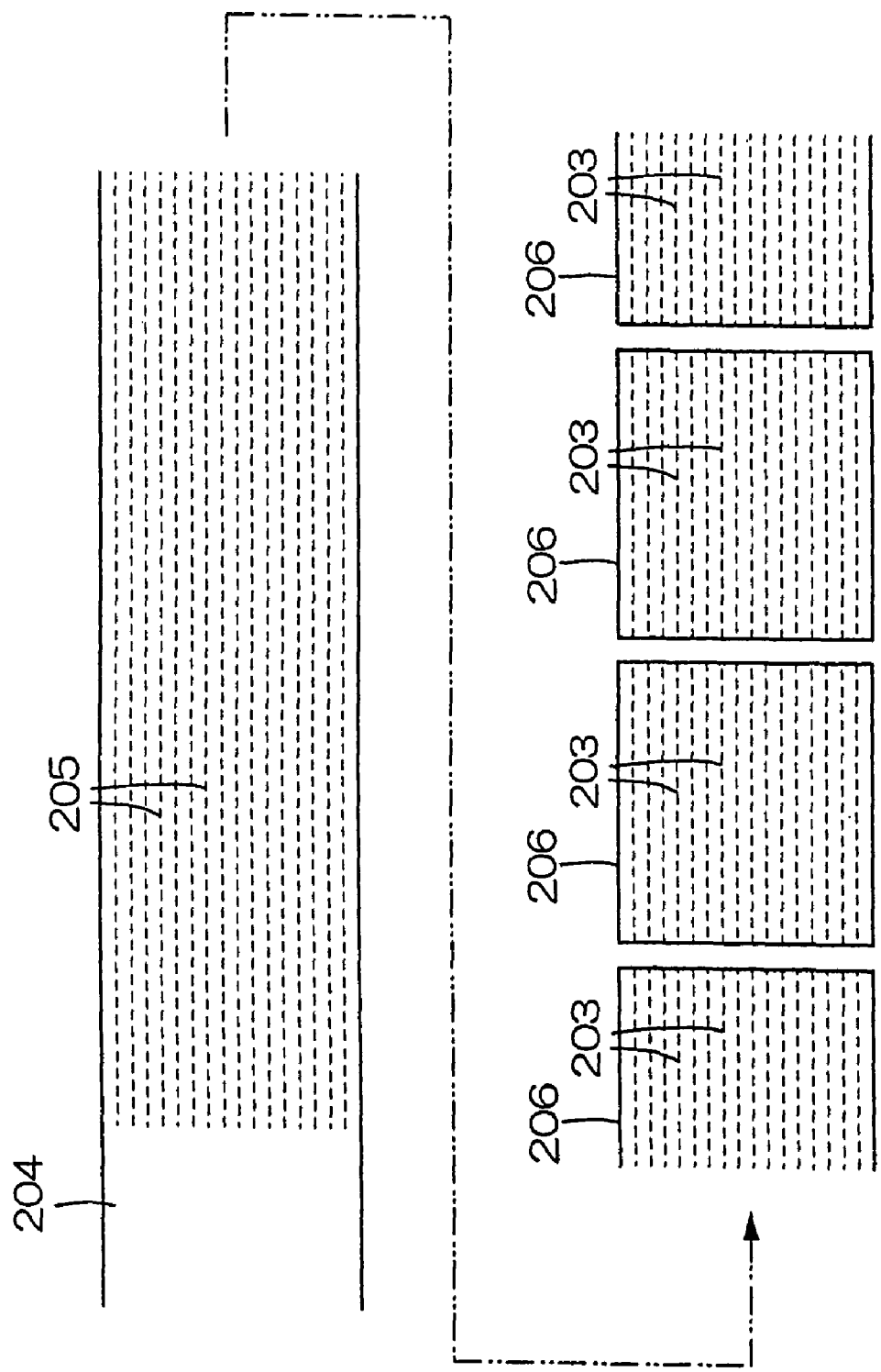
FIG. 8 is a plan view showing a step for producing stretchable sheet members in accordance with the first embodiment.
Figure 38:
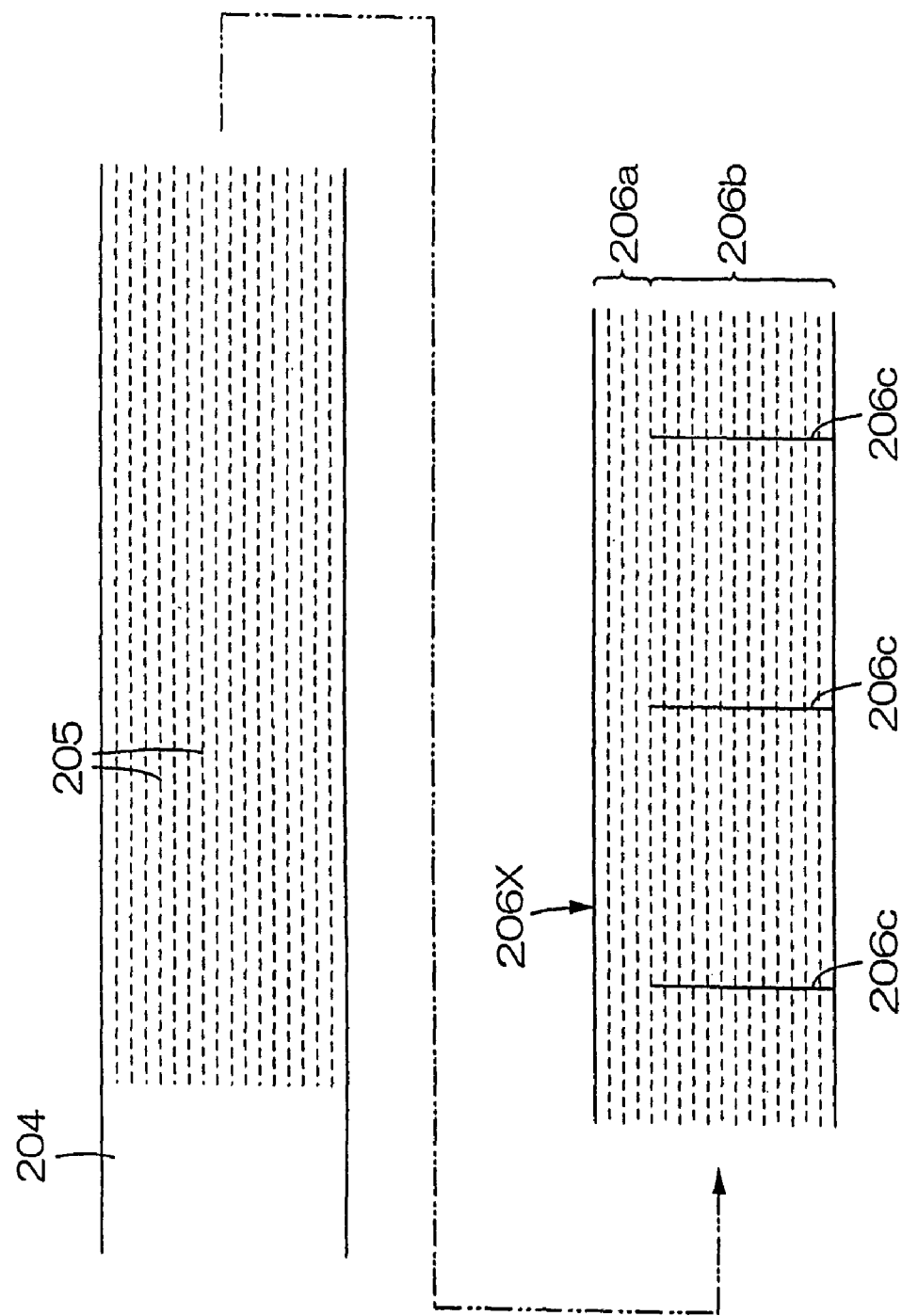
FIG. 38 is a plan view showing a modified embodiment of the first embodiment.
Figure 39:
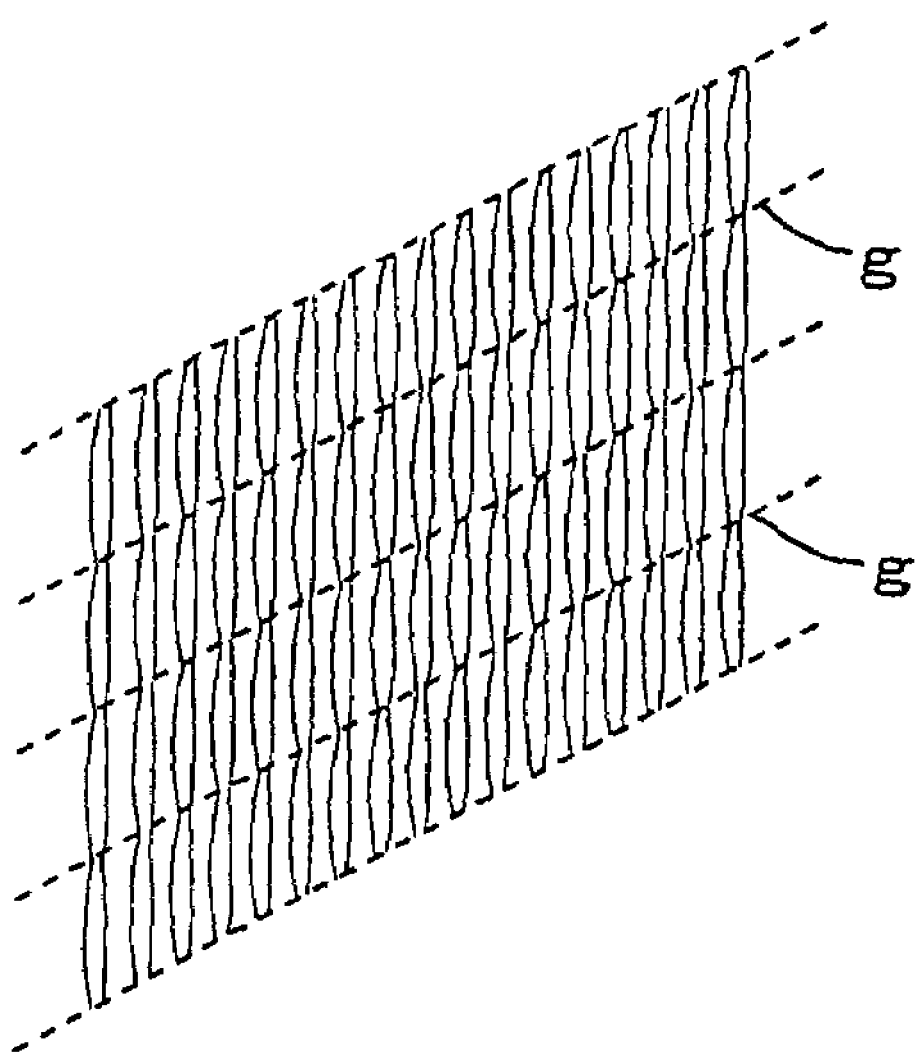
FIG. 39 is a schematic illustration showing creases, which are formed in the diaper of the present invention.

Alternatively again, the buttock stretchable member band-supplying line 230 shown in FIG. 7 may not be used. Precisely, stretchable sheet members produced in the same manner as shown in FIG. 8, may be arranged as they are, and fixed, with e.g. hot melt adhesive, on the predetermined portions of overall sheet in their stretched state. As for front body F, process is carried out in the same manner as stated before. By doing so, similarly to the diaper shown in FIG. 1, a paper diaper where buttock stretchable members are arranged and fixed continuously from the side edge of one side to the side edge of the other side in back body, while the under-waist stretchable members are discontinuous in front body, There is another cutting method of belt-shaped stretchable sheet member than that shown in FIG. 8. Precisely, as shown in FIG. 38, a belt-shaped stretchable sheet member 206X is cut not completely but halfway of the range having its crosswise length so that the side edge 206a is left uncut. Then, thus left side edge 206a is used as waist stretchable members, while separated portions 206b, 206b . . . are used as under-waist stretchable members and as buttock stretchable members, respectively. This cutting method is also included in the present invention. In FIG. 8, the reference mark 206c depicts a cutting line. By using such cutting method, the above waist stretchable member-supplying line shown in FIG. 6 is not required.

Second Embodiment

Figure 15:
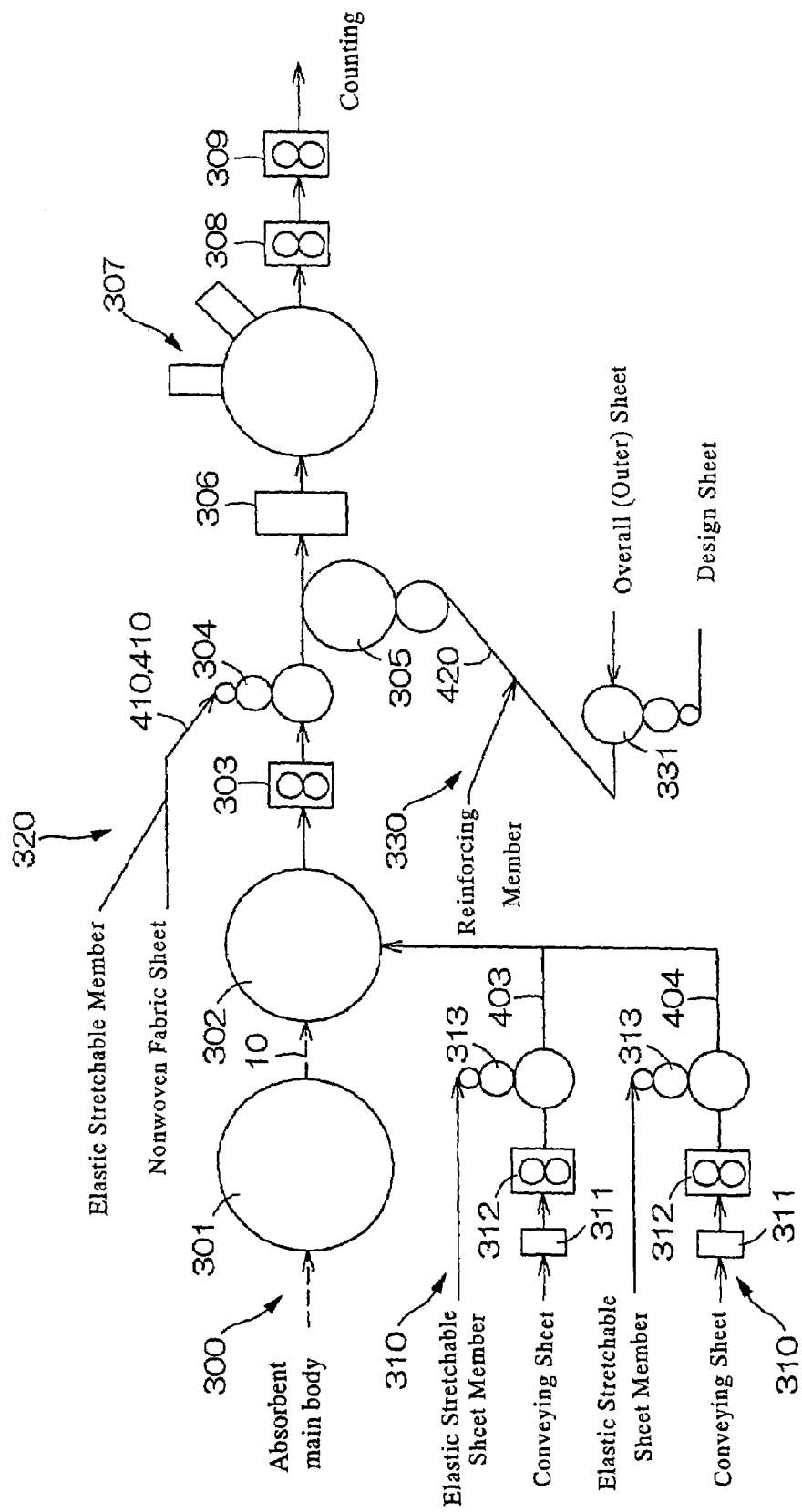
FIG. 15 is a flow diagram showing the producing line of the diaper in accordance with the second embodiment.

FIG. 15 shows an assembling draw of paper diaper of pants-type in accordance with the second embodiment. In this assembling draw, absorbent main bodys on each of which standing cuffs are formed, girth stretchable members, waist stretchable members and overall sheets are supplied to a main line, in the order named for assembling the diaper.

Figure 16:
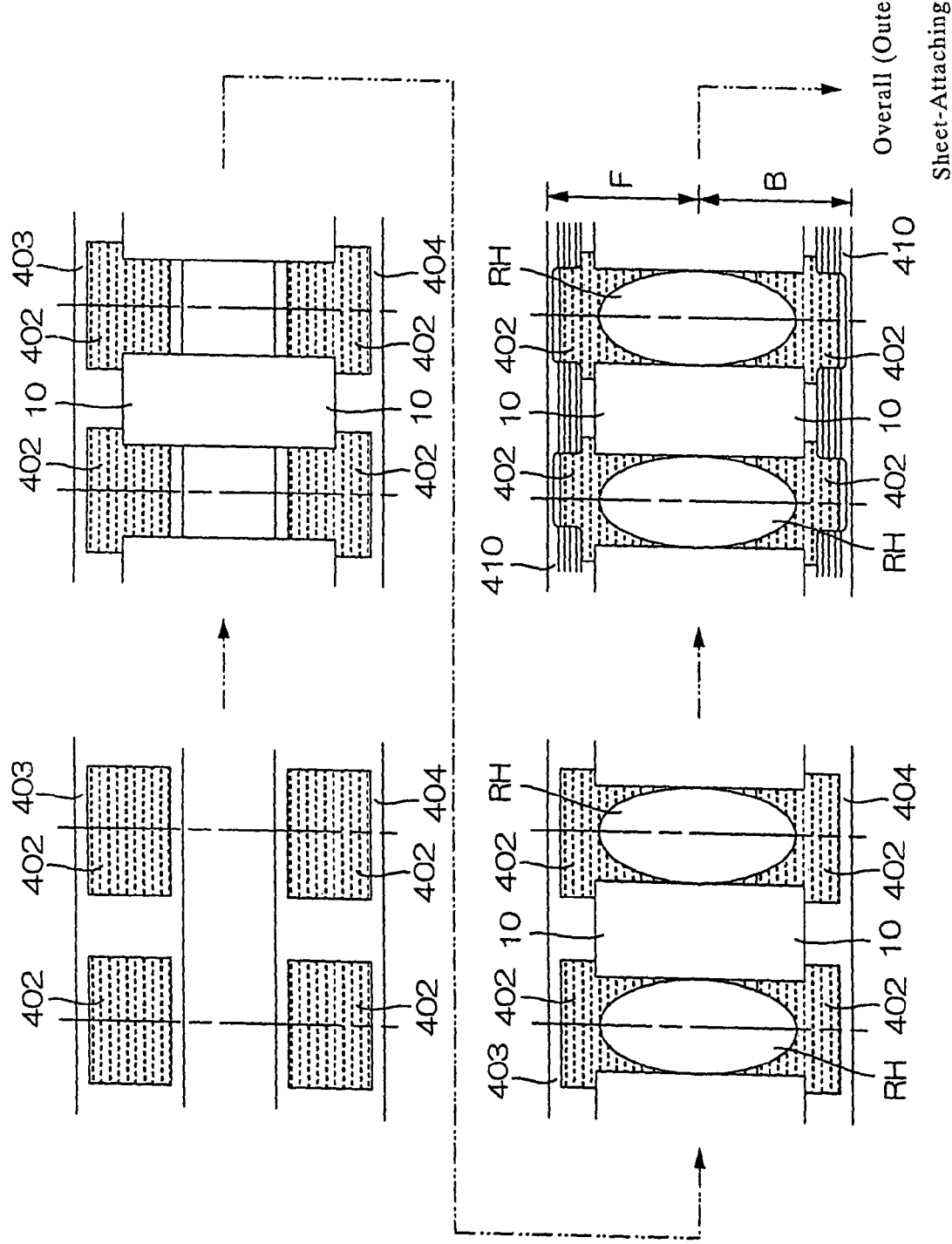
FIG. 16 is a plan view showing a main line in accordance with the second embodiment.
Figure 17:
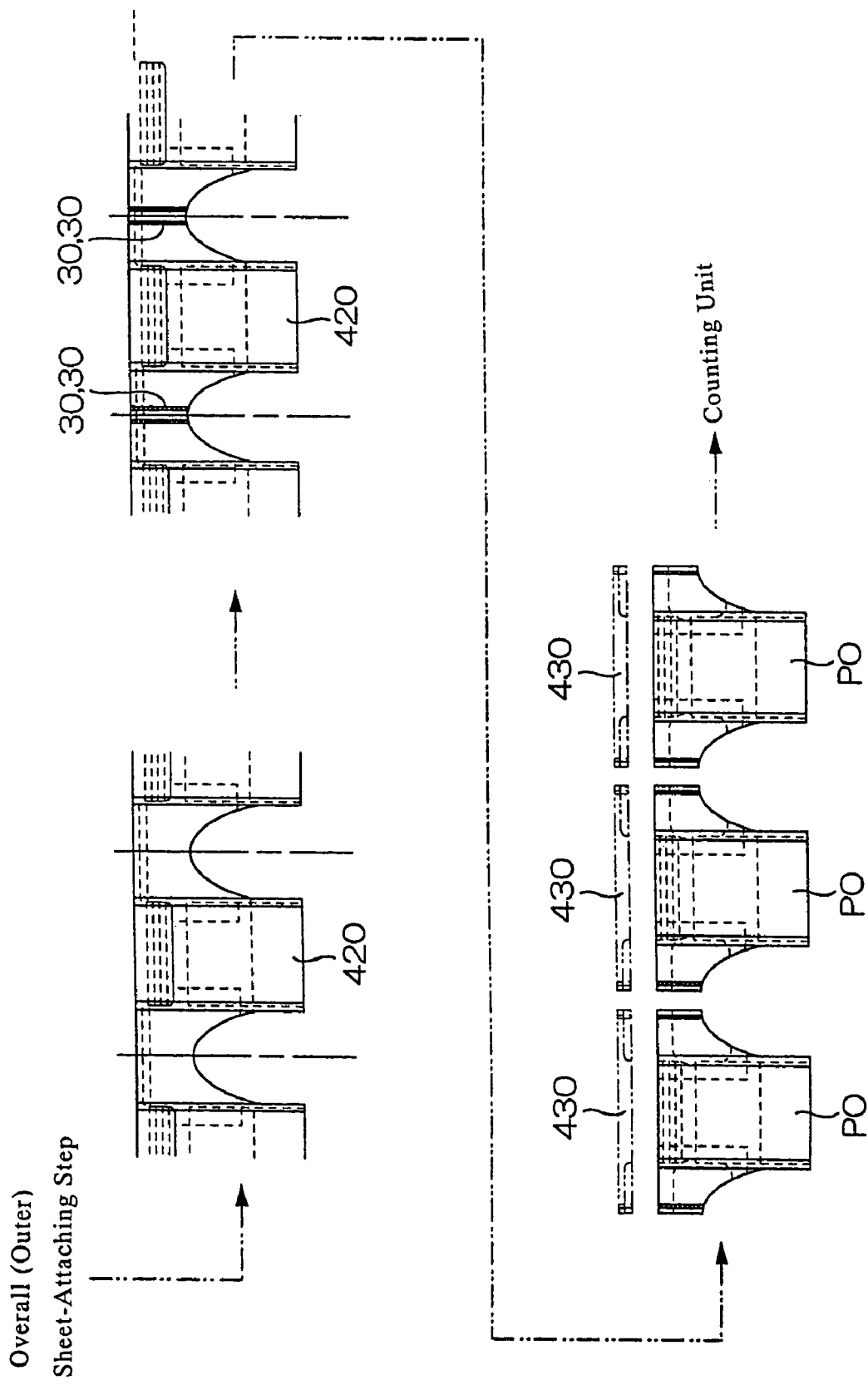
FIG. 17 is a plan view showing the main line in accordance with the second embodiment.

This assembling is carried out as follows. At first, the absorbent main bodys on which the standing cuffs are formed are supplied one by one from absorbent main body-producing line (not shown), while each lengthwise direction is identical to the conveying direction of main line 300. Each absorbent main body introduced into the main line 300 is turned for 90 degrees on a plane by means of 90 degrees-turn unit 301 so that the lengthwise direction of the absorbent main body is perpendicular to the conveying direction. Then, this absorbent main body is conveyed to a girth stretchable member-arranging unit 302. After the turning, the main line 300 is advanced as shown in FIGS. 16 and 17.

Figure 18:
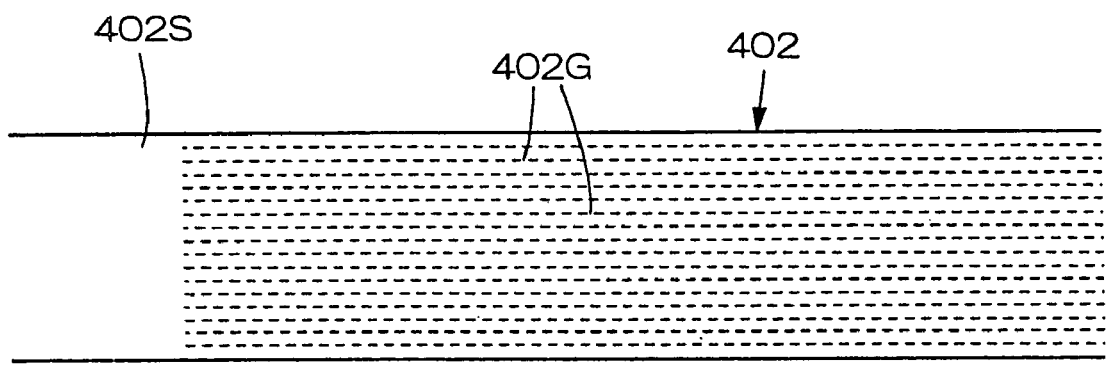
FIG. 18 is a plan view showing a step for producing an a stretchable sheet member in accordance with the second embodiment.
Figure 19:
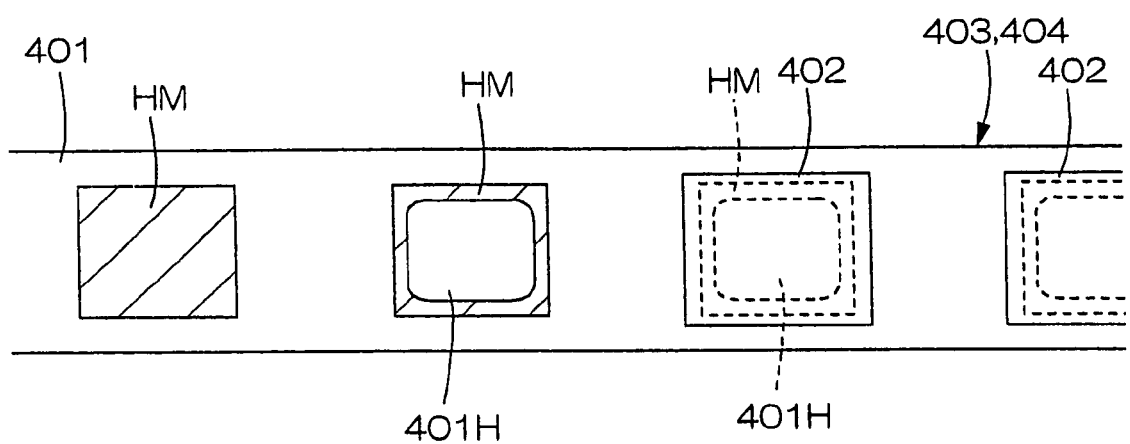
FIG. 19 is a plan view showing a step for producing an under-waist stretchable sheet band and a buttock stretchable sheet band.

In an under-waist stretchable member band-supplying line 310 and in a buttock stretchable member band-supplying line 310, under-waist stretchable member band 403 and buttock stretchable member band 404 are produced, respectively. In each line 310, 310, as shown in FIG. 18, continuous stretchable members 402G, 402G . . . are arranged and fixed on a belt-shaped support sheet 402S in their stretched state for forming a continuous belt-shaped stretchable sheet member 402. Particularly, a pair of nonwoven fabrics are attached each other and stretchable members are arranged and fixed so as to be continuous longitudinally between the nonwoven fabrics so that a continuous belt-shaped stretchable sheet member 402 is formed. On the other hand, belt-shaped conveying sheets 401, 401 made of nonwoven fabrics are supplied continuously in the under-waist stretchable member-supplying line 310 and buttock sretchable member-supplying line 310, respectively (See FIG. 15). Previously, stretchable member-attaching portions are set, with predetermined interval, on each conveying sheet 401 along its longitudinal direction. After that, the conveying sheet 401 is introduced into an adhesive-applying unit 311 (See FIG. 15), where melt adhesive HM is applied to the whole surface of stretchable member-attaching portions one by one as shown in FIG. 19. Next, the conveying sheet 401 is introduced into a die cutter 312 (See FIG. 15), where the conveying sheet 401 is cut at the stretchable member-attaching portions so as to make holes 401H while rectangular edges, to which the hot melt adhesive is applied, are left uncut so as to surround the holes 401H. Thus the conveying sheet 401 is introduced into a slipping and cutting unit 313 (See FIG. 15). In this unit 313, the above belt-shaped continuous stretchable sheet member 402, which is supplied separately, is slipped and cut one by one into cut members 402, 402 . . . having the predetermined length. Then, these cut stretchable sheet members 402, 402 . . . are attached on and fixed to the conveying sheet 401 one by one so as not to stretch, while each cut stretchable sheet member 402 stretches over each rectangular edge, to which the hot melt adhesive is applied, so as to cover totally each hole 401H. As a result, are obtained under-waist stretchable member band 403 and buttock stretchable member band 404, to which the stretchable sheet members 402, 402 . . . are attached intermittently on the longitudinal direction (which is crosswise direction of the diaper).

Next, the under-waist stretchable member band 403 and buttock stretchable member band 404 are supplied into the girth stretchable member-arranging unit 302 of main line 300. In this unit 302, as shown in FIG. 16, the under-waist stretchable member band 403 and buttock stretchable member band 404 are arranged on upper and lower end portions (corresponding to the under-waist area and buttock area, respectively) in the conveying line, while their surfaces, on which the stretchable sheet members 402, 402 are attached, direct upward. Additionally, the above absorbent main bodys 10 are arranged on the both bands 403, 404 at its predetermined positions. Then, the both bands 403, 404 are cut at predetermined positions so as to make holes corresponding to leg openings RH, RH . . . by means of leg opening die cutter 303. After that, thus treated bands 403, 404 are introduced into a slipping and cutting unit 304 so as to be processed to have discontinuous stretchable sheet members 402, 402 arranged thereon.

Figure 20:
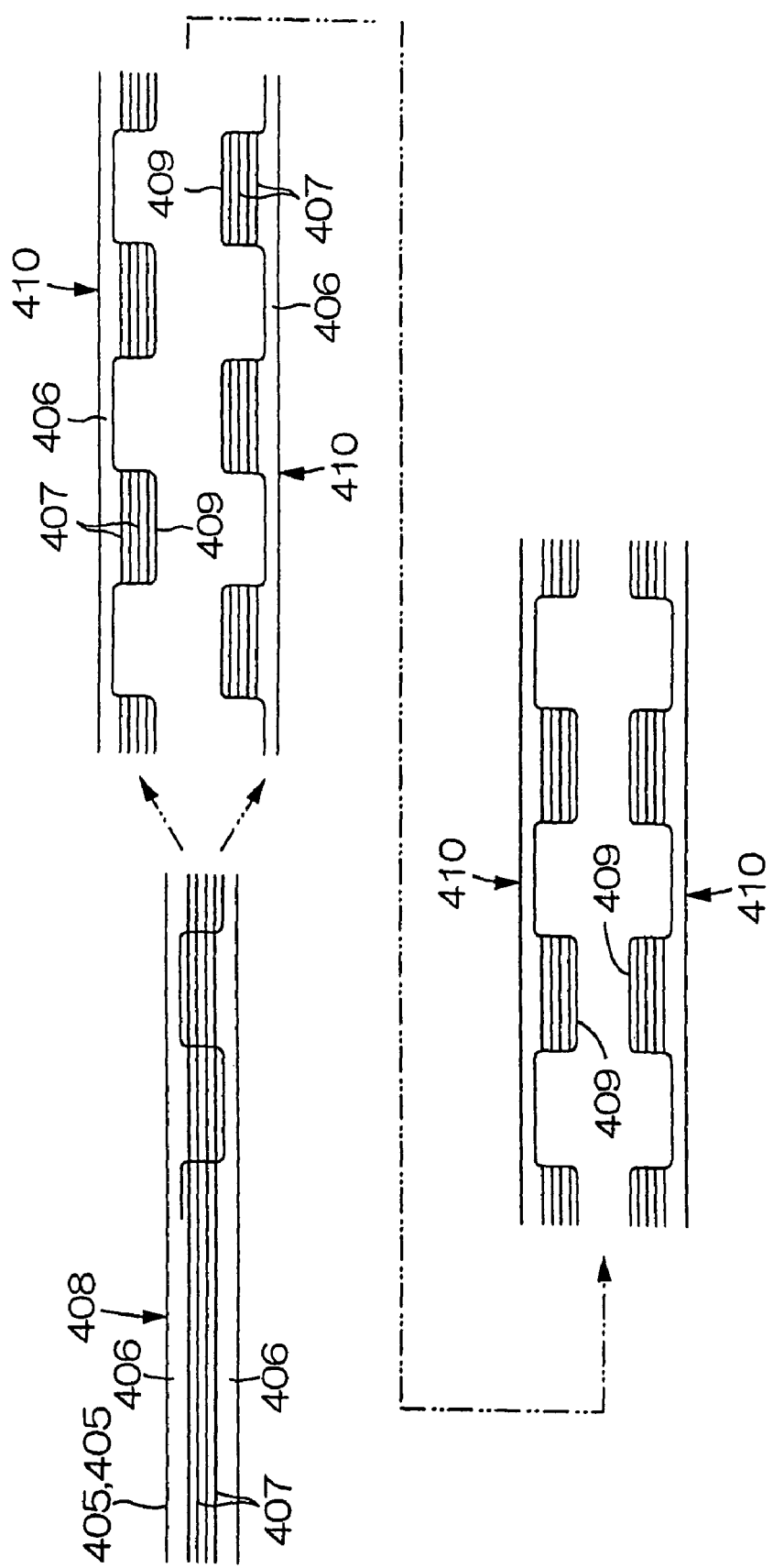
FIG. 20 is a plan view showing a step for producing waist stretchable members in accordance with the second embodiment.

In a waist stretchable member band-supplying line 320 (See FIG. 15), a pair of waist stretchable member band 410, 410 are produced. Referring to FIG. 20, at first, a pair of belt-shaped nonwoven fabrics are attached each other. Space formed between the nonwoven fabrics is divided conceptually to three portions on its crosswise direction, longitudinal upper and lower edge portions 406 and 406 and longitudinal middle portion. Then, a plurality of continuous stretchable members e.g. rubber threads 407, 407 . . . are arranged and fixed in the longitudinal middle portion in their stretched state for forming a continuous belt-shaped stretchable member 408 successively. This belt-shaped stretchable member 408 is divided longitudinally into two portions by cutting the fixed and belt-shaped stretchable members 407. In this case, a cutting line continues to cross on the widthwise direction of the member between upper side edge and lower side edge alternatively with predetermined interval on the lengthwise direction of the member, resulting in a waveform (in FIG. 20, in the form of rectangular pulse). Thus divided portion defines a pair of waist stretchable members (belt-shaped divided members) 410, 410. Each waist stretchable member consists of a plurality of side edge portions 406, 406 . . . and a plurality of projections 409, 409 . . . . Here, the side edge portions 406, 406 . . . do not have any stretchable member. Then, the plurality of projections 409, 409 . . . have stretchable members 407, 407 . . . and are projected at the predetermined interval on the lengthwise direction with which the belt-shaped stretchable member 408 is cut. Then, the pair of waist stretchable members 410, 410 are supplied to the main line. When the belt-shaped stretchable member 408 is cut, phase shift is occurred between the projections 409, 409 . . . of one waist stretchable member and those of the other waist stretchable member. However, when the pair of waist stretchable members (belt-shaped divided members) 410, 410 are introduced into a slipping and cutting unit 304, the phase of one waist stretchable member is adjusted so that the phase of projections 409, 409 . . . of one belt-shaped divided member 410 and that of other belt-shaped divided member 410 agree with each other.

As stated above, the belt-shaped divided members 410, 410 are introduced into the slipping and cutting unit 304 (See FIG. 15). On the other hand, the under-waist stretchable member band 403 and buttock stretchable member band 404 are separately introduced into the slipping and cutting unit 304. Therefore, in this unit 304, one belt-shaped divided members 410 are arranged and fixed, as the waist stretchable members of front body, on the predetermined position of arranged under-waist stretchable member band 403 in their stretched state. At the same time, in the slipping and cutting unit 304, the other belt-shaped divided members 410 are arranged and fixed, as the waist stretchable members of back body, on the predetermined position of arranged under-waist stretchable member band 403 in their stretched state. As a result, all kinds of members, which are to be attached on the inner surface of the overall sheet, are arranged on the predetermined positions. Then, these members are introduced, as they are, into an overall sheet-attaching unit 305 successively.

Figure 21:
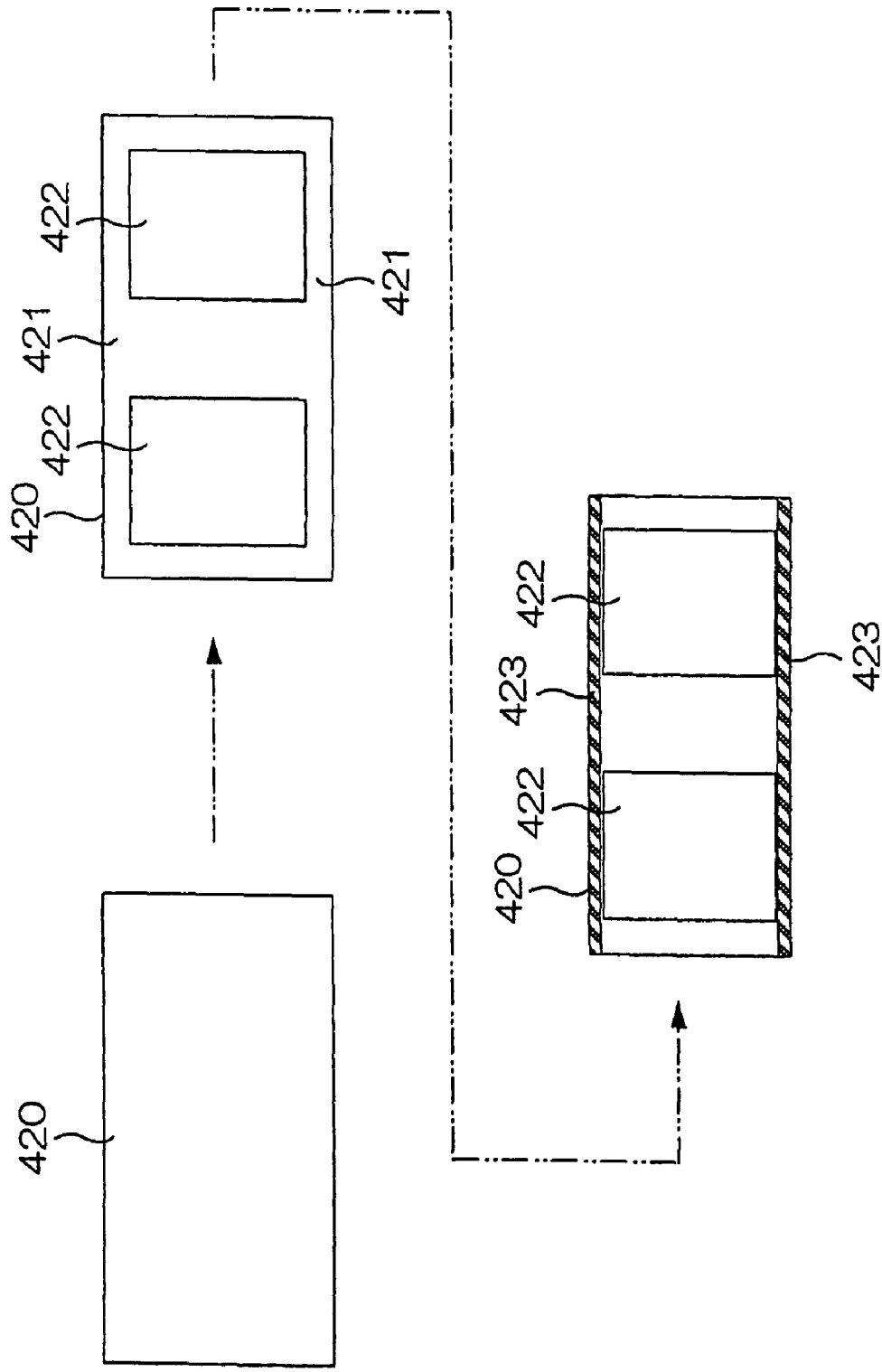
FIG. 21 is a plan view showing a step for producing an overall sheet in accordance with the second embodiment.

An overall sheet 420 is separately produced in an overall sheet-producing line 330 so as to be introduced into the overall sheet-attaching unit 305 (See FIG. 15). In this embodiment, previously, the overall sheet 420 is cut into the predetermined rectangle shaped sheet 420 in a slipping and cutting unit 331. The design sheet 422, 422 . . . , which are supplied successively from the slipping and cutting unit 331, are arranged and fixed side by side. In the embodiment shown in FIG. 21, each design sheet 422 made of opaque film is provided with visible design and arranged and fixed on the outer (upper) surface of overall sheet 420 so as to cover the predetermined portion for the absorbent main body. By arranging the overall sheet 420 in such way, the central portion of each range having the crosswise length corresponding to the width of girth stretchable member will be hidden later by the design sheet 422 resulting in neat appearance in the both of front body and back body.

In this diaper, the overall sheet 420 is previously, at the opposite side edges 421, 421, folded back upon itself so as to form double portions. Then, reinforcing members 423 such as color urethane film are adhesive-bonded in the opposite double portions. By doing so, the side edges can be flexible. Instead of reinforcing member, color hot melt adhesive-bonding is carried out so that the side edges 421, 421 become flexible or conspicuous.

Thus produced overall sheet 420 is supplied into a member-attaching unit 305 of main line 300. In this member-attaching unit 305, the overall sheet 420 is turned so that the direction of width of diaper is identical to the conveying direction of main line. Then, the under-waist stretchable member band 403, buttock stretchable member band 404, absorbent main body 10 and waist stretchable members 410, 410, all of which are separately introduced, are arranged and fixed on (not shown) the predetermined positions of overall sheet 420. Next, these stretchable members and absorbent main body are together with the overall sheet 420 are folded up, by an folding unit 306 (See FIG. 15) so that the opposite side edges 30, 30 of each back body B is put upon the opposite side edges 30, 30 of each front body B, respectively, which is understood by comparison of FIG. 16 with FIG. 17. Thus folded overall sheet 402 is introduced into a heat seal unit 307, where heat seal is carried out at the side edges 30, 30 . . . . After that, the overall sheet 420 is introduced into a slitter cutter 308. In this slitter cutter 308, first, margins 430 provided for conveying are cut away. Then, the overall sheet 420 is cut so as to have slit at each waist opening's edge. Additionally, the overall sheet 420 is cut away so as to separate each other at the side edges 30, 30. Further, thus separated individual piece is trimmed into a diaper PO having the predetermined size as a product. Finally, the diapers PO, PO . . . are introduced into a counting unit (not shown) successively.

Figure 22:
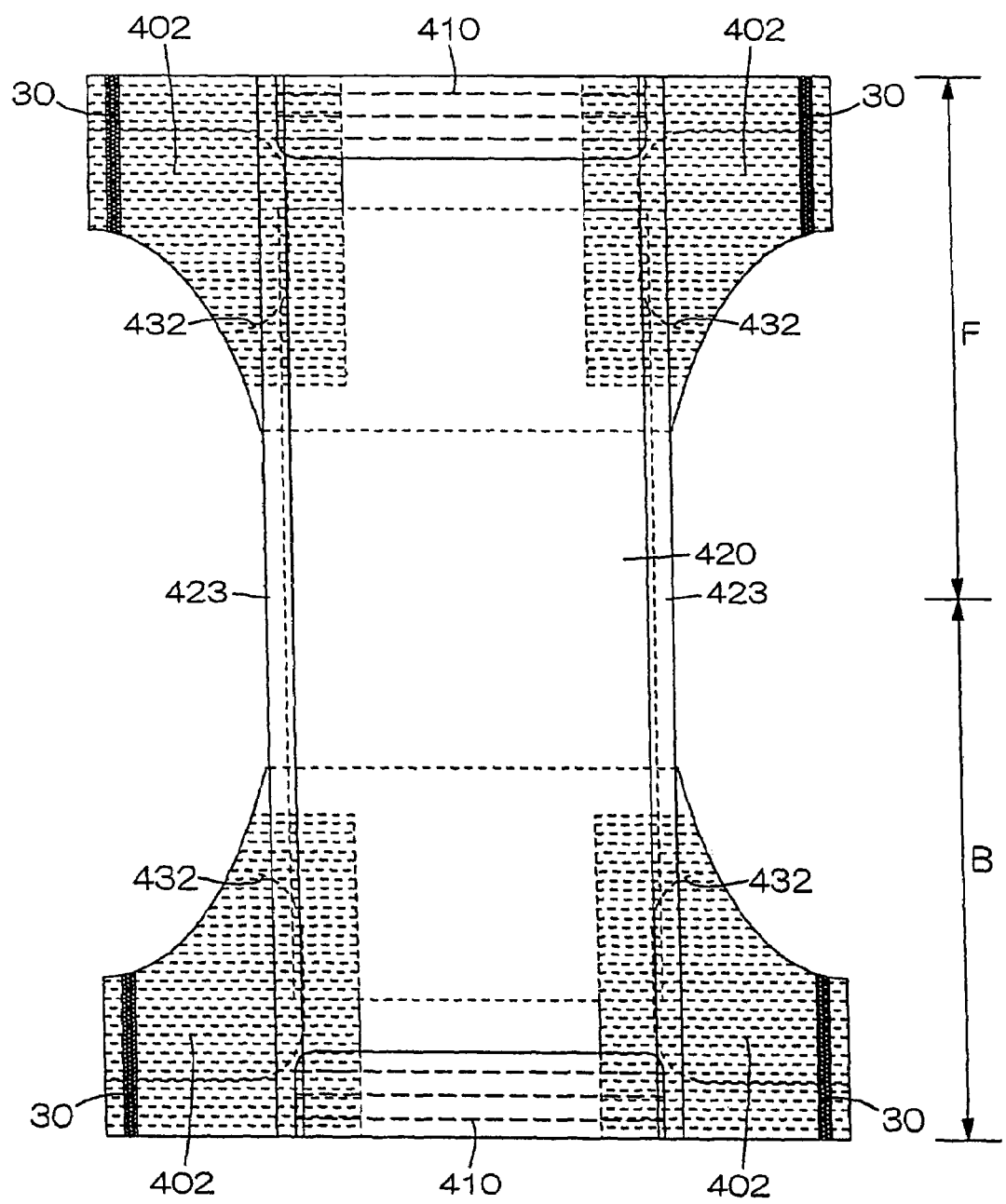
FIG. 22 is a plan view of disposable diaper of pants-type in accordance with the second embodiment when the diaper is in its flat-out state.

In a thus produced paper diaper PO, as shown in a diaper depicted in FIG. 22 while it is in flat-out state (inner-side), in the front body F, the under-waist stretchable sheet members 402, 402 are provided from the joint 30 of one side to the joint 30 of the other side, while they are discontinuous at the range having the central portion of crosswise length corresponding to the width of absorbent. Further, in the back body B, the buttock stretchable sheet members 402, 402 are provided from the joint 30 of one side to the joint 30 of the other side, while they are discontinuous at the range having the central portion of crosswise length corresponding to the width of absorbent. In this case, there are stretchable sheet members 402, 402, which are continuous to waist stretchable member extended in the front body. Then, these stretchable members are considered to be identical to the waist stretchable members extended in the back body functionally and conceptually. In the paper diaper produced in accordance with the method of the present invention, each under-waist stretchable sheet member 402 and each buttock stretchable sheet member 402 are attached together with U-frame shaped support sheets 432, 432 (Originally, they are conveying sheets 401, 401), on the under-waist stretchable member band 403, buttock stretchable member band 404, respectively.

Alternatively, the under-waist stretchable sheet members 402, 402 . . . and buttock stretchable sheet members 402, 402 . . . are discontinuous at the range having the whole of crosswise length corresponding to the absorbent.

In the present second embodiment, the following modified embodiments (a) to (c) can be included.

(a) In the foregoing embodiments, the waist stretchable member band-supplying line 320 is provided with the mechanism for attaching discontinuously the waist stretchable members. Then, in another embodiment, this mechanism can be used as the mechanism for attaching discontinuously the under-waist stretchable member in the under-waist stretchable member band-supplying line 310 and as the mechanism for attaching discontinuously the buttock stretchable member in the buttock stretchable member band-supplying line 310. Additionally in this other embodiment or in further another embodiment, the mechanism for attaching discontinuously the under-waist stretchable member in the under-waist stretchable member band-supplying line 310 and the mechanism for attaching discontinuously the buttock stretchable member in the buttock stretchable member band-supplying line 310 can be used as the mechanism for attaching discontinuously the waist stretchable member in the waist stretchable member band-supplying line 320 or a conventional stretchable member-attaching method can be used in one of these lines.

(b) Further another embodiment differs from the foregoing embodiments in only the buttock stretchable member band-supplying line 310. Precisely, the buttock stretchable member band-supplying line 310 supplies the buttock stretchable member band, which is provided with longitudinally continuous stretchable members. Concretely, continuous belt-shaped stretchable sheet member 402, shown in FIG. 18, is produced. Then, this member 402 is, as it is, supplied to the above stretchable member-arranging unit 302 of main line 300. Due to this configuration, in the resultant paper diaper, in the same manner as the paper diaper shown in FIG. 5, only the buttock stretchable members are arranged and fixed from the side edge of one side to the side edge of other side without any discontinuous part, while the under-waist stretchable members are arranged and fixed discontinuously.

Figure 23:
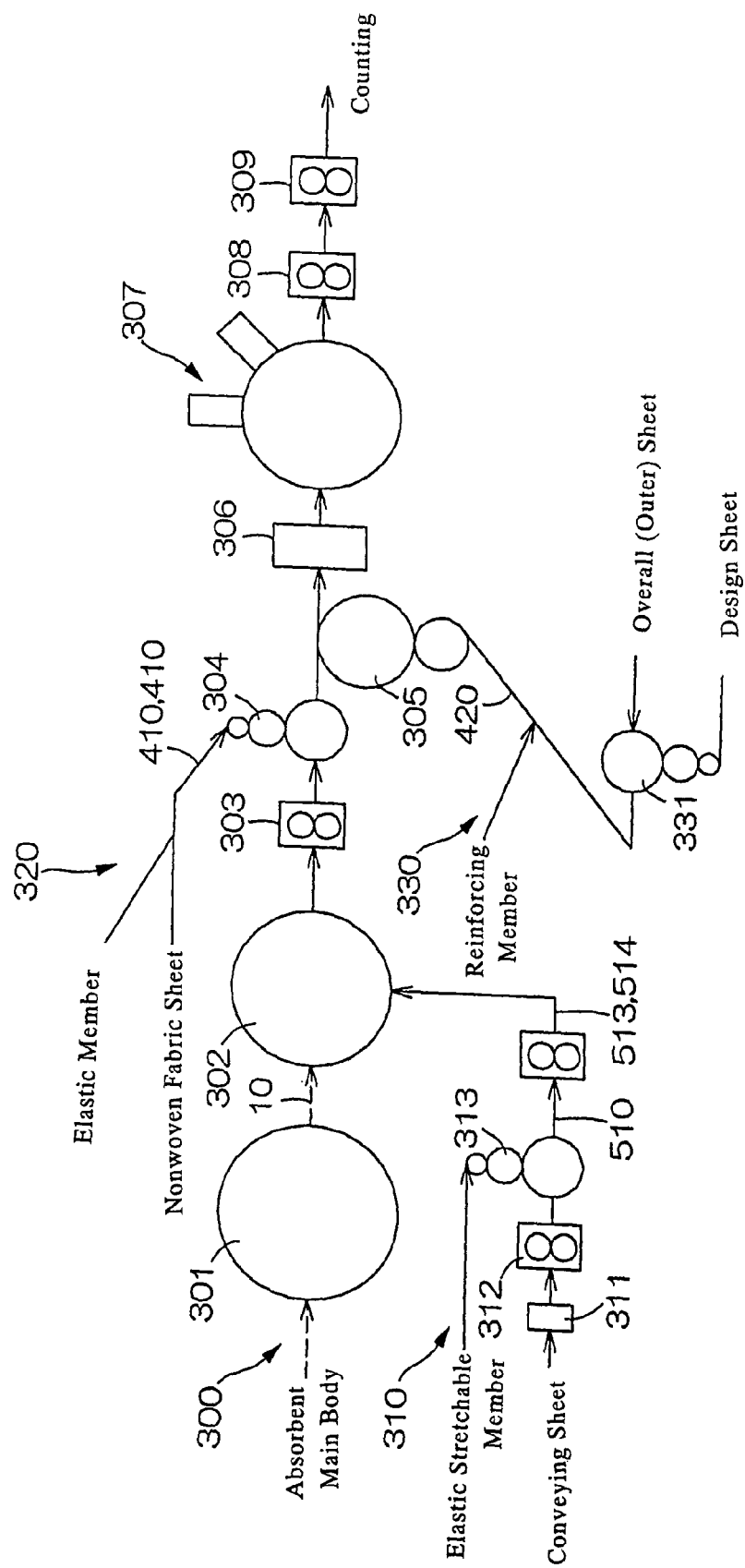
FIG. 23 is a flow diagram showing the producing line of the diaper in accordance with a modified embodiment of the second embodiment.

(c) In attaching method of foregoing embodiments, the under-waist stretchable member band-supplying line and the buttock stretchable member band-supplying line are provided separately. However, as shown in FIG. 23, the under-waist stretchable member band-supplying line and buttock stretchable member band-supplying line define one line. For this reason, a stretchable member band 510, which has the large width, is produced. Then, this band 510 is cut along the longitudinal centerline L on the crosswise direction into two bands, under-waist stretchable member band 513 and buttock stretchable member band 514, which are to be supplied to the above girth stretchable member-arranging unit 302. As a result, these bands can be arranged on the predetermined positions, respectively.

Third Embodiment

FIG. 25 shows an assembling draw of paper diaper of pants-type in accordance with the third embodiment. This draw comprises an absorbent main body-producing and supplying line 600, overall sheet-producing and supplying line 700 and final process line 800.

In the absorbent main body-producing and supplying line 600, at first, an absorbent core is supplied while its lengthwise direction is identical to its conveying direction. Next, a liquid pervious top sheet is covered and fixed on the absorbent core. Then, standing cuffs are arranged and fixed on the opposite sides of the liquid pervious top sheet. Additionally, the resultant absorbent core covered with the top sheet having the standing cuffs is arranged and fixed on a liquid impervious back sheet, which is separately supplied, so that the finished piece of absorbent main body 10 is obtained. In this embodiment, the liquid impervious back sheet 10 is previously, at the opposite side edges, folded back upon itself so as to form double portions. Then, reinforcing members such as urethane film are adhesive-bonded between the opposite double portions. By doing so, the side edges can be flexible (Instead of reinforcing member, color hot melt adhesive-bonding is carried out so that the side edges become flexible or conspicuous).

The resultant absorbent main body 10 is turned for 90 degrees on a plane by means of 90 degrees-turn unit 610 so that the lengthwise direction of the absorbent main body 10 is perpendicular to the conveying direction. Then, this absorbent main body 10 is conveyed to an overall sheet-attaching unit 801 of the final process line 800.

On the other hand, in the overall sheet-producing and supplying line 700, under-waist stretchable members and buttock stretchable members and waist stretchable members are attached to a belt-shaped overall sheet 701, which is continuous on the crosswise direction of the diaper.

Now, explanation is carried out particularly. First, the belt-shaped overall sheet 701 is introduced into a slipping and cutting unit 710. On the other hand, a design sheet 702, which is supplied separately, is slipped into the slipping and cutting unit 710 and cut one by one so as to form many predetermined shaped design sheets. Then, as shown in also FIG. 28, these predetermined shaped design sheets 702, 702 . . . are arranged and fixed, with e.g. hot melt adhesive, on the upper surface of belt-shaped overall sheet 701 at the central portion on the crosswise direction in the front body and at the central portion on the crosswise direction in the back body. As the design sheet, for example, an opaque film with patters such as design character can be used.

Next, the belt-shaped overall sheet 701, to which the design sheets 702, 702 . . . are attached, is supplied to a slipping and cutting unit 720 for attaching the girth stretchable member so that the under-waist stretchable members and buttock stretchable members are attached to the overall sheet 701 in the manner according to the present invention.

Figure 26:
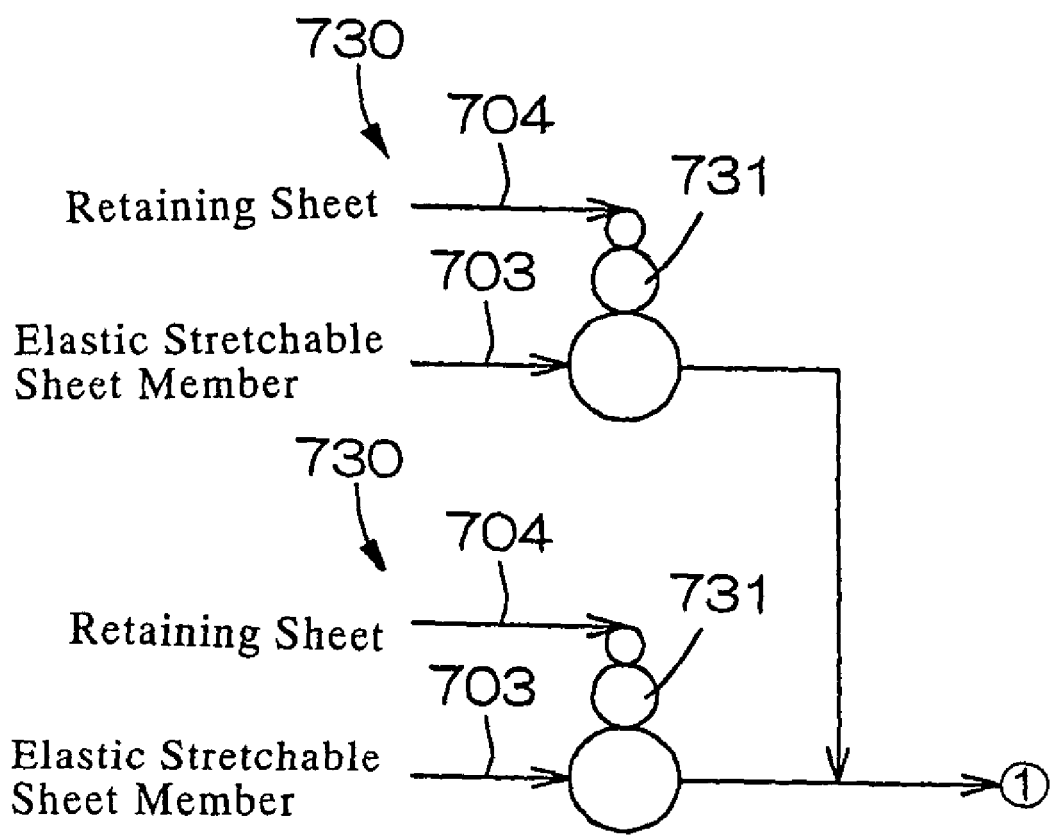
FIG. 26 is a flow diagrams showing line ① part of FIG. 25.
Figure 27:
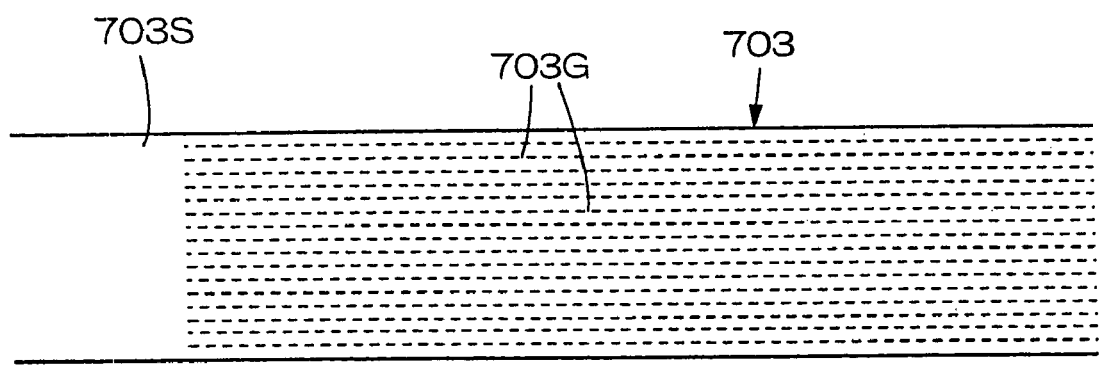
FIG. 27 is a plan view showing a step for producing an stretchable sheet member in accordance with the third embodiment.

Therefore, in this embodiment, as shown in FIG. 26, an under-waist stretchable member band-supplying line 730 and buttock stretchabale member band-supplying line 730 are provided separately. In each supplying line 730, as shown in FIG. 27, a plurality of continuous stretchable members 703G such as rubber threads are arranged and fixed on a belt-shaped support sheet 703S in their stretched state resulting in a continuous belt-shaped stretchable sheet member 703. This sheet member 703 is supplied into a slipping and cutting unit 731. In this way, these two continuous belt-shaped stretchable sheet members 703, 703 can be formed in two lines, respectively. However, one continuous belt-shaped stretchable sheet member is formed, and this member is cut along the lengthwise direction into a plurality of belt-shaped continuous stretchable sheet members.

Figure 30:
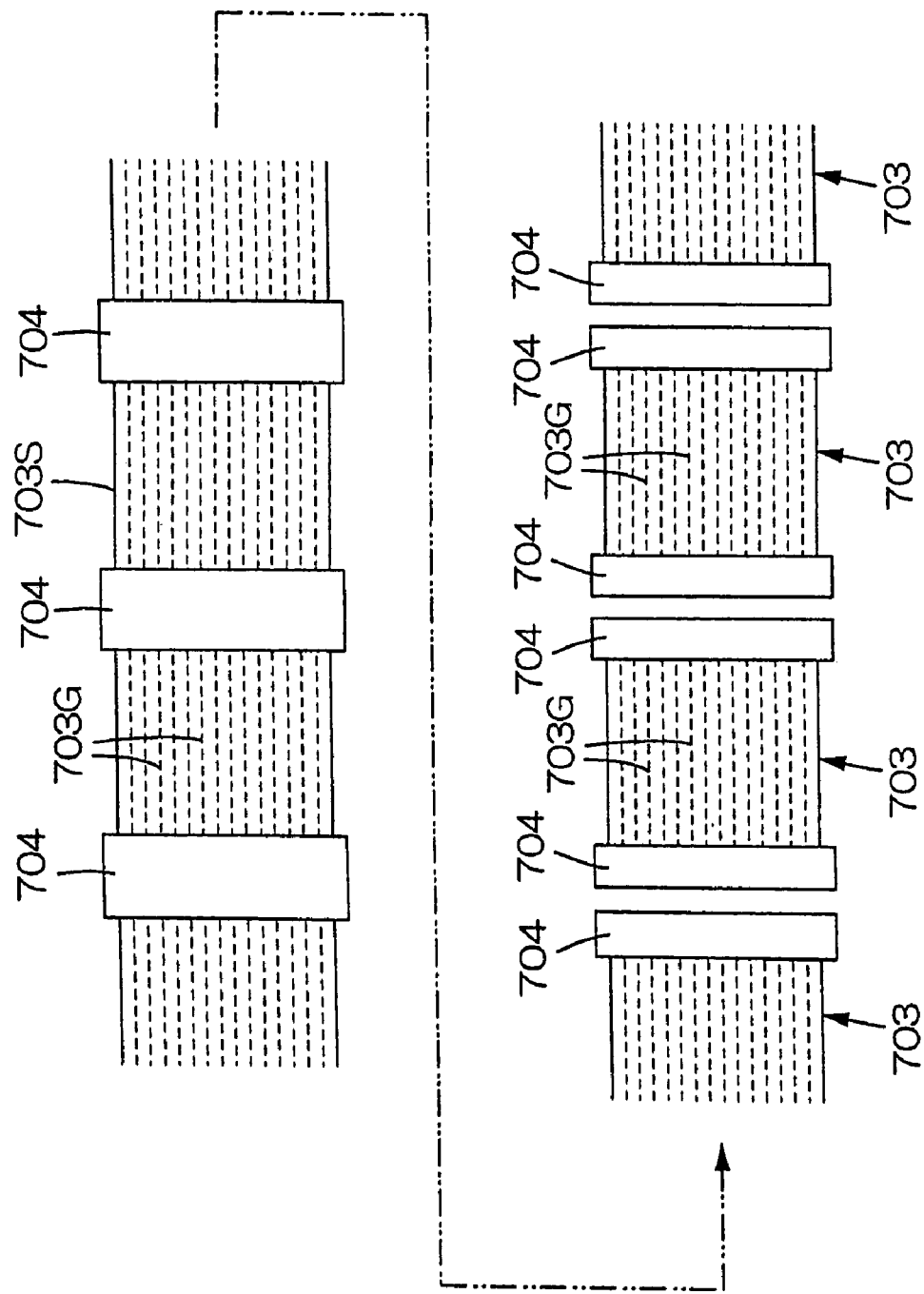
FIG. 30 is a plan view showing a step for attaching retaining sheets in accordance with the third embodiment.

On the other hand, in each supplying line 730, as shown in FIG. 26, a belt-shaped stretchable retaining sheet 704, which has larger width than that of continuous belt-shaped stretchable sheet member 703, is supplied separately to the slipping and cutting unit 731. In this unit 731, the belt-shaped stretchable retaining sheet 704 is cut one by one with predetermined length into many cut sheets 704, 704 . . . . As the retaining sheet 704, film or nonwoven fabrics can be used, which have high adhesiveness to the overall sheet and the stretchable member. Then, the cut retaining sheets 704, 704 . . . are, as shown in FIG. 30, arranged and fixed by e.g. hot melt adhesive on the upper surface of the belt-shaped stretchable sheet member 703 at the predetermined interval on the longitudinal direction.

Figure 28:
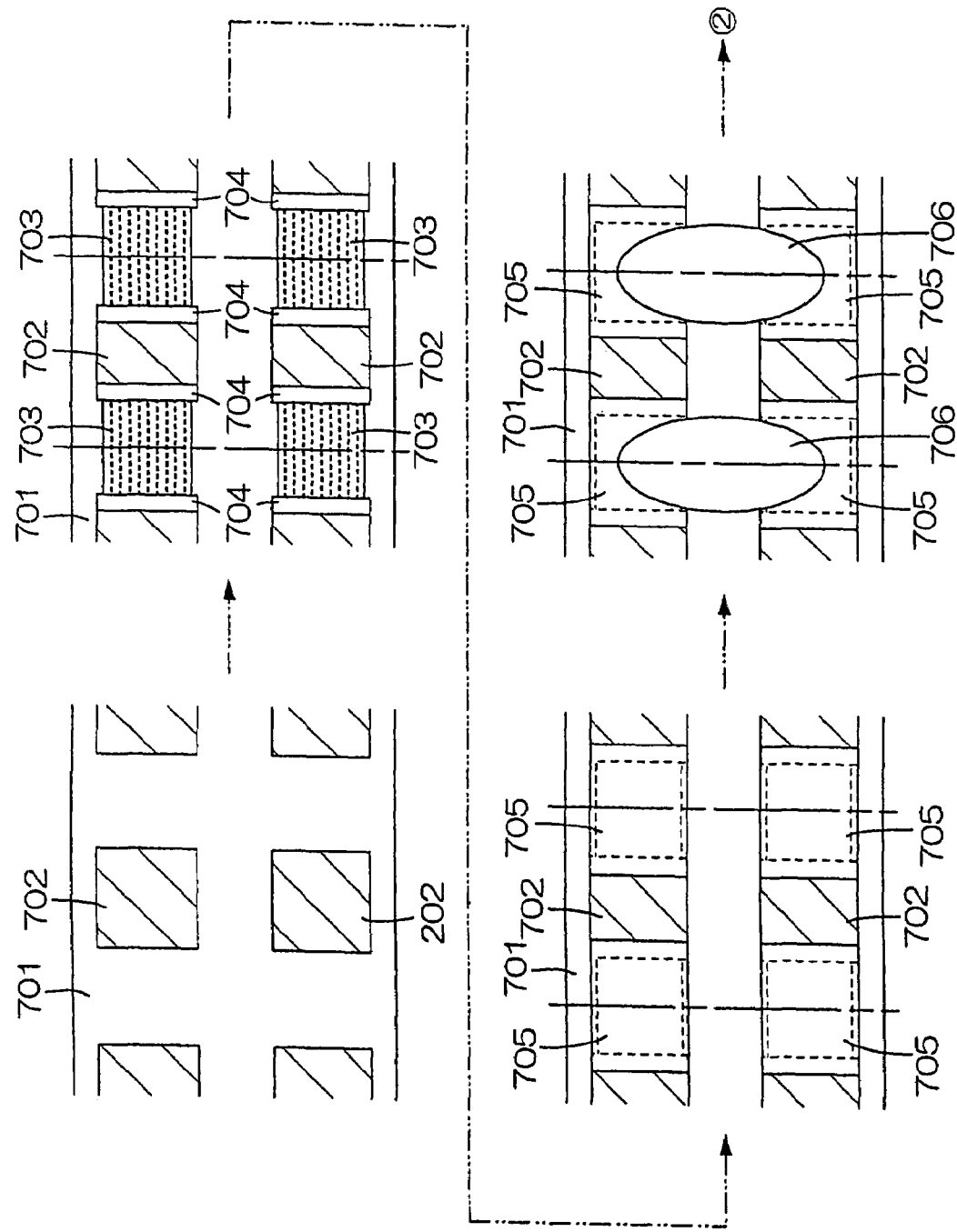
FIG. 28 is a plan view showing the producing step of a line for producing a girth stretchable member in accordance with the third embodiment.

Thus produced belt-shaped stretchable sheet member 703, to which the retaining sheets 704, 704 . . . are fixed, is introduced into the slipping and cutting unit 720 for attaching the girth stretchable members. In this slipping and cutting unit 720, belt-shaped stretchable sheet member 703, to which the retaining sheet is fixed, is slipped and cut one by one along the centerline between each pair of retaining sheets (this centerline goes along the crosswise direction of belt-shaped stretchable sheet member 703) into many cut sheet members 703, 703 . . . . Therefore, as shown in FIG. 28, the pairs of the retaining sheets 704, 704 . . . are fixed to these cut stretchable sheet members 703, 703 . . . at their both sides, respectively. Then, each pair of retaining sheets 704, 704 are independent each other and fixed to the both side edges of each stretchable sheet member 703 on the crosswise direction of diaper. In this situation, the pair of retaining sheets 704, 704 project upward and downward from the stretchable sheet member at its both side edges so as to form projected portions S, S . . . (See FIG. 31).

Figure 31:
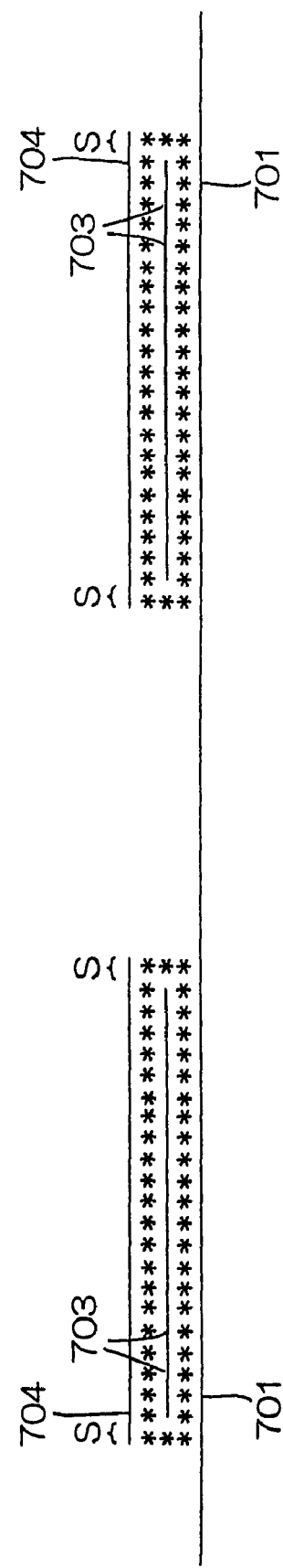
FIG. 31 is a longitudinal sectional view showing stretchable sheets provided with retaining sheets and attached to the diaper, in accordance with the third embodiment.
Figure 32:
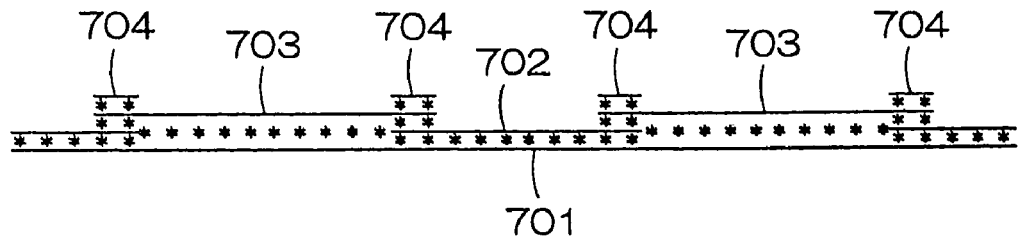
FIG. 32 is a longitudinal sectional view showing the stretchable sheets provided with the retaining sheets and attached to the diaper, taken in another direction in accordance with the third embodiment.

Precisely, the retaining sheets 704, 704 . . . are, as shown in FIG. 28, fixed to the stretchable sheet members 703, 703 . . . so as to stretch on the crosswise direction of diaper with elasticity. Further, the retaining sheets 704, 704 . . . are, as shown in FIG. 31, fixed one by one together with projected portions S, S . . . with adhesive to the upper surface of overall sheet 701, to which the design sheets 702, 702 . . . are attached and which is introduced successively. FIG. 32 is a sectional view taken in the line along the crosswise direction of diaper for showing this fixing.

Thus, each stretchable sheet member 703 is adhesive-bonded to the overall sheet 701 through the pair of retaining sheet S, S (704, 704), which are not stretchable. Additionally, the stretchable sheet member 703 per se can be fixed to the overall sheet 701 with larger adhesive-bonding area comparing other cases. Hence, each stretchable sheet member 703 can be adhesive-bonded to the overall sheet 701 in its stretched state against the constricting power of the stretchable sheet member 703. As a result, even if the stretchable sheet member 703 is attached discontinuously (intermittently) to the overall sheet 701, the stretchable sheet member 703 can keep stretching with elasticity due to such configuration.

Figure 33:
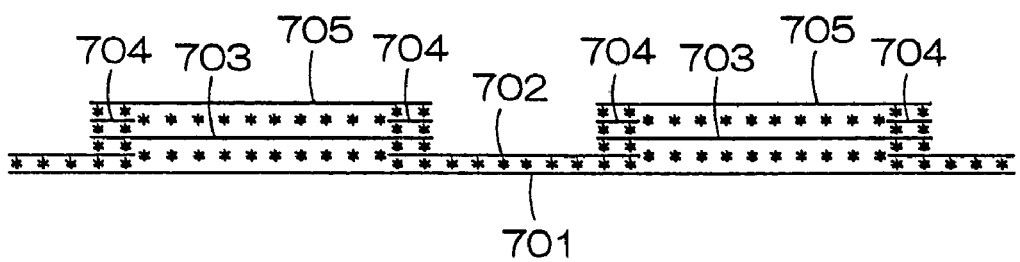
FIG. 33 is a longitudinal sectional view showing cover sheets attached to the diaper, in accordance with the third embodiment.

Next, the overall sheet 701, to which the stretchable sheet members 703, 703 . . . are attached, is introduced into a slipping and cutting unit 740 for attaching a cover sheet. A continuous belt-shaped cover sheet 705 is separately supplied into this unit 740, where the cover sheet 705 is slipped so as to be cut one by one into many sheets 705, 705 . . . having predetermined shape. On the other hand, the overall sheet 701 is also supplied into this slipping and cutting unit 740 and to this overall sheet 701, the stretchable sheet members 703, 703 . . . are attached. Additionally, to the stretchable sheet members 703, 703 . . . , the retaining sheets 704, 704 . . . are attached intermittently. Then, as shown in FIGS. 28 and 33, each cut cover sheet 705 covers the whole upper surface of each stretchable sheet member 703 so as to be adhesive-bonded there with e.g. hot melt adhesive.

Next, the resultant overall sheet 701 is introduced into a die cutter unit 750 (See FIG. 25) successively. In this unit 750, the overall sheet 701 is cut so as to make holes, each of which is corresponding to two leg openings of two adjacent diapers. In FIG. 28, this hole is designated by reference numeral 706.

Figure 29:
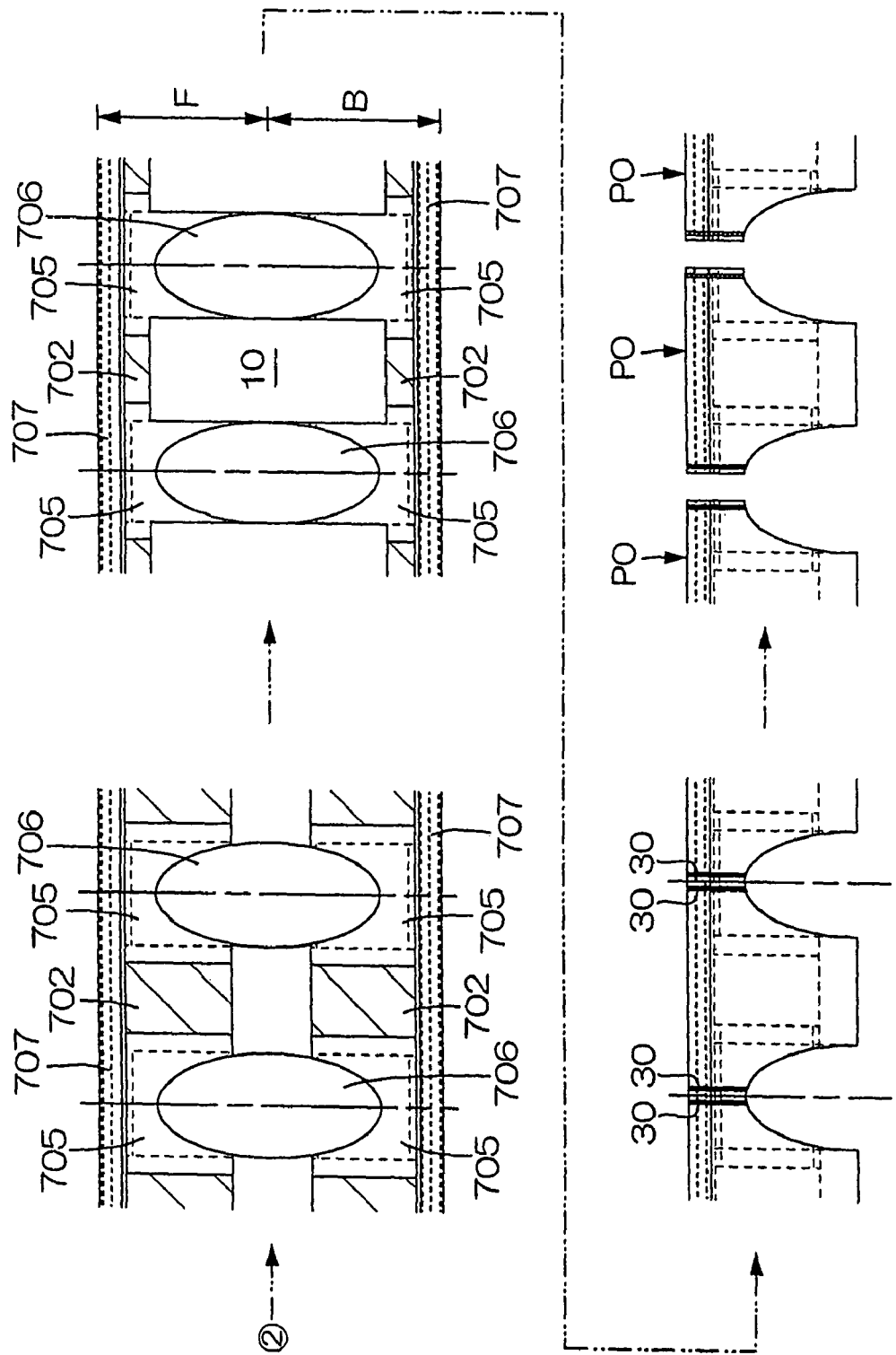
FIG. 29 is a plan view showing the change of sate in a final process line in accordance with the third embodiment.
Figure 34:
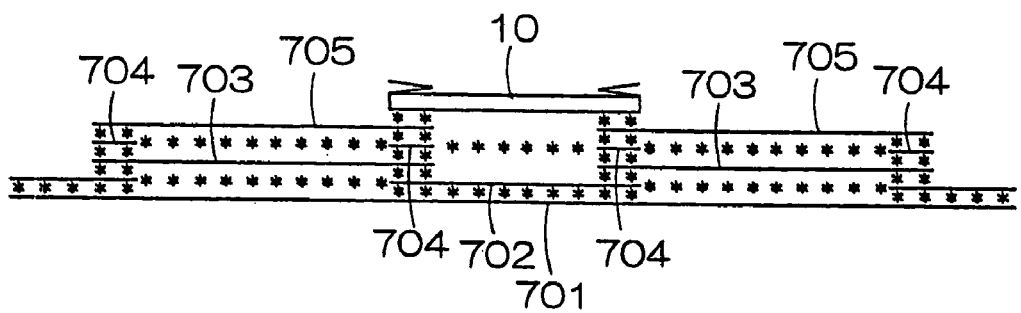
FIG. 34 is a longitudinal sectional view showing an absorbent main body attached to the diaper, in accordance with the third embodiment.

Thus treated overall sheet 701, to which the stretchable members are attached, is introduced into an overall sheet-attaching unit 810 of final line 800. In this unit 800, at first, as shown in FIG. 29, a plurality of continuous stretchable members 707, 707 . . . are supplied to the waist opening edge so as to be spaced and to be parallel each other and fixed there with hot melt adhesive. On the other hand, the absorbent main bodys 10, 10 . . . are separately introduced into the overall sheet-attaching unit 810. Then, as shown in FIGS. 29 and 34, each absorbent main body 10 is arranged and fixed by hot melt adhesive-bonding to the overall sheet 701 at the central portion of crosswise direction of the diaper.

Next, the overall sheet 701, which completes the attaching of stretchable members and adsorbent structure, is introduced into a folding unit 820. In this unit 820, as shown in FIG. 29, the overall sheet 701 is folded up so that the opposite side edges 30, 30 of each back body B is put upon the opposite side edges 30, 30 of each front body B, respectively. Then, thus folded overall sheet 201 is introduced into a heat seal unit 830, where heat seal is carried out at the side edges 30, 30 . . . . After that, the overall sheet 201 is introduced into a final cutter 840. In this final cutter 350, first, margins provided for conveying are cut away. Then, the overall sheet is cut so as to have slit at each waist opening's edge. Additionally, the overall sheet is cut away so as to separate each other at the side edges. Further, thus separated individual piece is trimmed into a diaper PO having the predetermined size as a product. After such cutting, visible design such as pattern of animation character, mark or the like are transferred to each diaper PO by means of transfer roll 850 if desired. Finally, the diapers PO, PO . . . are introduced into a counting unit (not shown) successively.

Figure 35:
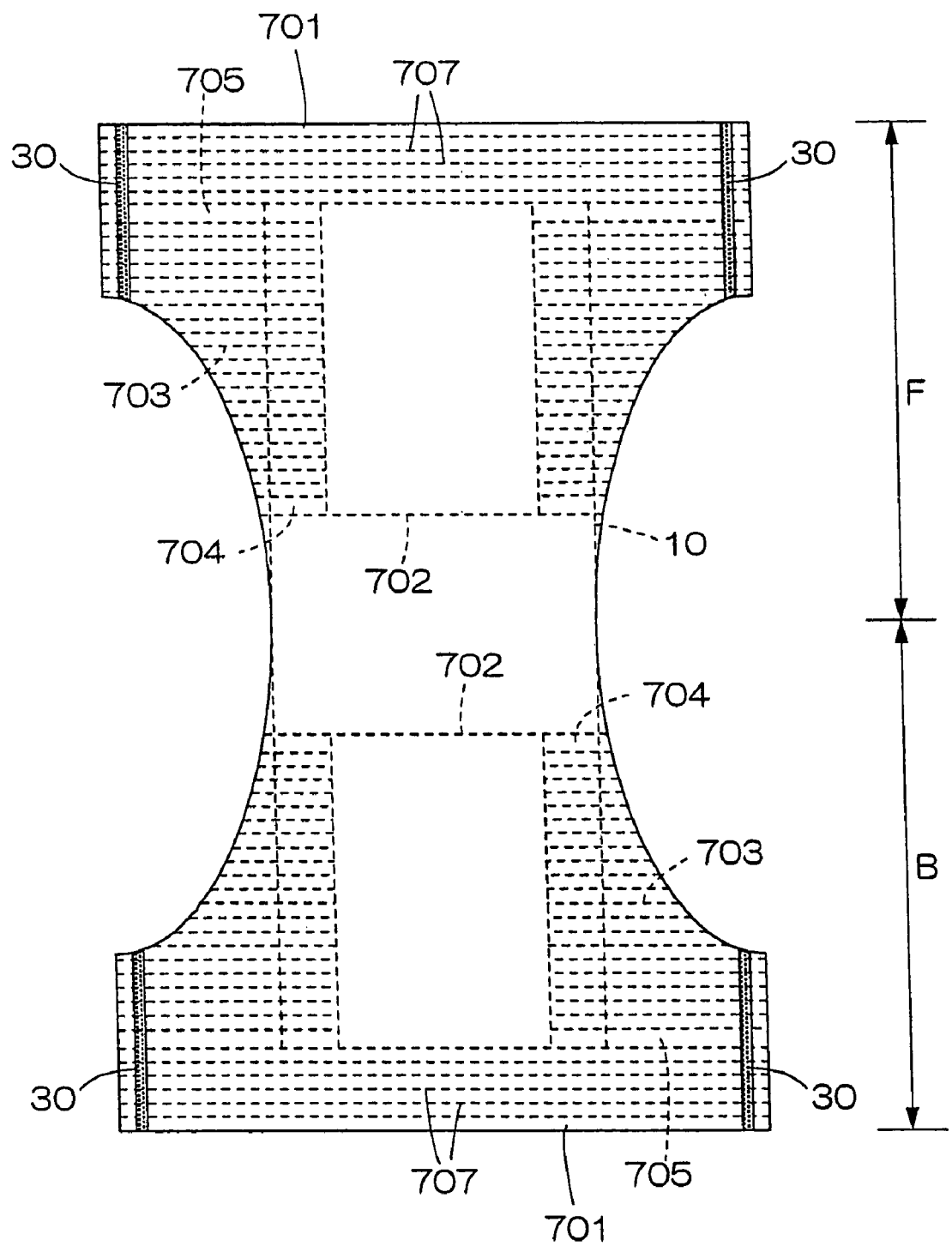
FIG. 35 is a plan view showing a disposable diaper (inner surface facing a wearer) produced by a method in accordance with the third embodiment when the diaper is in its flat-out state.

In a thus produced paper diaper PO, as shown in a diaper depicted in FIG. 35 while it is in flat-out state (inner-side), in the front body F, the under-waist stretchable members 703, 703 . . . are provided from the joint 30 of one side to the joint 30 of the other side, while they are discontinuous at the range having the central portion of crosswise length corresponding to the width of absorbent. Further, in the back body B, the buttock stretchable members 703, 703 . . . are provided from the joint 30 of one side to the joint 30 of the other side. However, they are discontinuous at the range having the central portion of crosswise length corresponding to the width of absorbent. Then, in the pair of opposite under-waist stretchable sheet members 703, 703 and in the pair of opposite buttock stretchable sheet members 703, 703 of each diaper, at their inboard side portions (absorbent side portions), there are pairs of retaining sheets 704, 704, which are laminated and fixed there. These pairs of retaining sheets are independent each other in the front body and in the back body, respectively. Although the inboard side portions of pair of under-waist stretchable sheet members 703, 703 and the inboard side portions of pair of buttock stretchable sheet members 703, 703 are superposed on the both side edges of the absorbent main body 10, respectively, the stretchable members located there are not visible, because they are hidden by the design sheet.

Alternatively, the under-waist stretchable sheet members 703, 703 . . . and buttock stretchable sheet members 703, 703 . . . are discontinuous at the range having the whole of crosswise length corresponding to the absorbent.

In the present third embodiment, the following modified embodiments (a) and (b) can be included.

Figure 36:
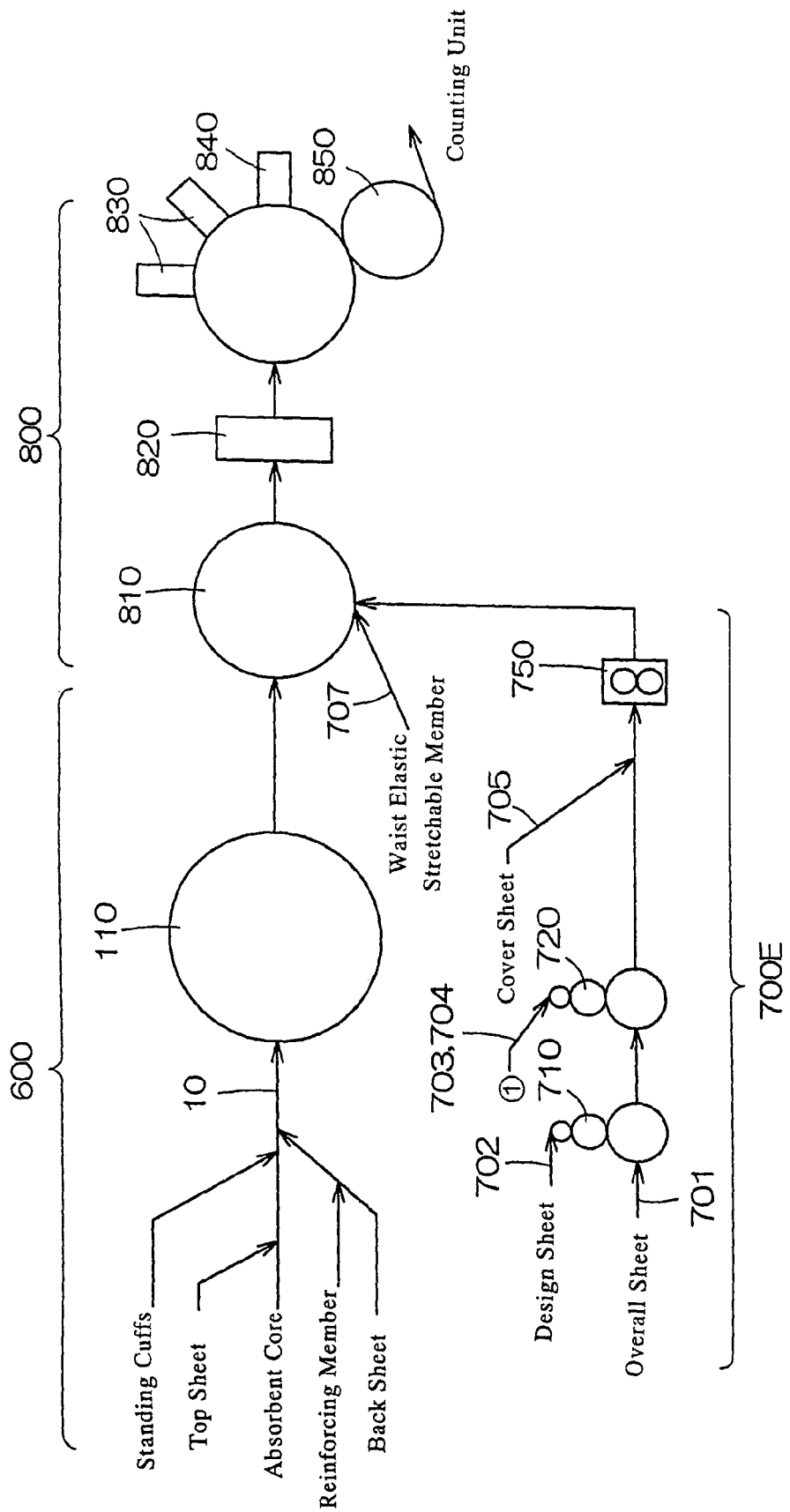
FIG. 36 is a flow diagram showing a modified embodiment of the third embodiment.
Figure 37:
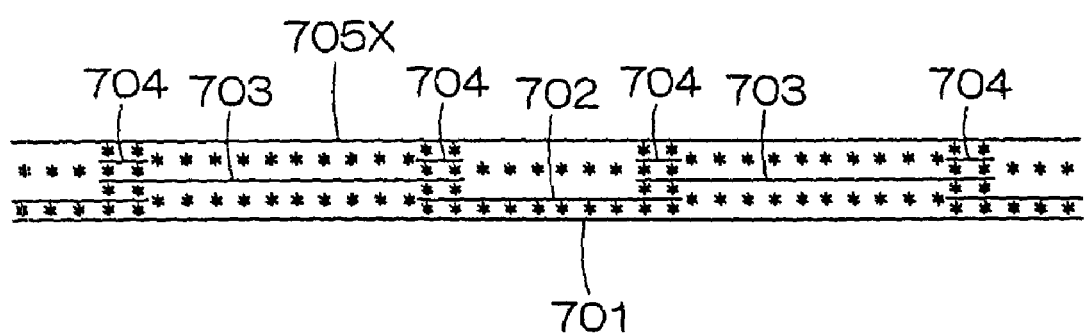
FIG. 37 is a longitudinal sectional view showing cover sheets attached to the diaper in accordance with a modified embodiment of the third embodiment.

(a) In the foregoing embodiments, the cover sheets are attached intermittently corresponding to the stretchable members, to which the retaining sheets are fixed. Accordingly, the slipping and cutting unit is required. However, the slipping and cutting unit can be omitted in an assembling draw, as shown in FIG. 36. In this case, as shown in FIG. 37, in each diaper, a continuous belt-shaped cover sheet 705X is, as it is, attached continuously along the portion of stretchable members, to which the retaining sheets are fixed.

(b) In another embodiment, the buttock stretchable member band-supplying line 230 shown in e.g. FIG. 7 can be omitted. In this case, in the same manner as conventional method, continuous stretchable members such as rubber threads are arranged along the crosswise direction of diaper in their stretched state and fixed there by e.g. hot melt adhesive. Due to this configuration, in the resultant paper diaper, only the buttock stretchable members are arranged and fixed from the side edge of one side to the side edge of other side without any discontinuous part, while the under-waist stretchable members are arranged and fixed discontinuously.

What is claimed is:

1. A disposable diaper having an absorbent, a waist opening and right and left leg openings that are formed when the diaper is in use, and a plurality of stretchable rubber threads that are provided along the peripheral direction of the diaper at least in a girth area having a lengthwise range extending from an edge of the waist opening to a beginning of the leg openings, the stretchable rubber threads being spaced at intervals in the lengthwise direction of the diaper, said disposable diaper comprising:

an overall bottom sheet that defines an outer surface of the diaper;

a liquid pervious top sheet;

an absorbent main body disposed between the overall bottom sheet and the liquid pervious top sheet, the absorbent main body comprising the absorbent and a liquid impervious back sheet, wherein the absorbent main body is fixed to said diaper so that there is a portion of the girth area where the absorbent main body is not located; and an elastic sheet-shaped member comprising a support sheet positioned between the overall bottom sheet and the liquid pervious top sheet, the stretchable rubber threads being fixed in an elastically stretched state on said support sheet, the support sheet being provided on the overall bottom sheet at least in a portion of the area where the absorbent main body is located;

wherein the support sheet is discontinuous in the area of the absorbent main body so that the support sheet does not overlap with at least a portion of the absorbent main body.

2. The disposable diaper of claim 1, wherein the stretchable rubber threads are continuous along the support sheet.

3. The disposable diaper of claim 1, comprising plural overall bottom sheets and wherein the support sheet is disposed between the plural overall bottom sheets.

4. The disposable diaper of claim 1, wherein the absorbent main body is disposed between the overall bottom sheet and the support sheet.

5. The disposable diaper of claim 1, wherein a visible design is provided on an outer surface of the diaper in an area that overlies the absorbent main body.

6. The disposable diaper of claim 1, wherein said support sheet is provided on the overall bottom sheet in a position that is 30 mm or less from the edge of the waist opening and 10 mm or less from the beginning of the leg openings.

* * * * *